(12) United States Patent
Desjarlais et al.

(10) Patent No.: US 7,553,930 B2
(45) Date of Patent: Jun. 30, 2009

(54) BAFF VARIANTS AND METHODS THEREOF

(75) Inventors: John R. Desjarlais, Pasadena, CA (US); Adam Read Thomason, San Francisco, CA (US); Eugene Alexander Zhukovsky, West Hollywood, CA (US)

(73) Assignee: Xencor, Inc., Monrovia, CA (US)

( * ) Notice: Subject to any disclaimer, the term of this patent is extended or adjusted under 35 U.S.C. 154(b) by 655 days.

(21) Appl. No.: 10/794,751

(22) Filed: Mar. 5, 2004

(65) Prior Publication Data

US 2005/0048626 A1    Mar. 3, 2005

Related U.S. Application Data

(63) Continuation-in-part of application No. 10/338,083, filed on Jan. 6, 2003.

(60) Provisional application No. 60/528,104, filed on Dec. 8, 2003, provisional application No. 60/523,880, filed on Nov. 20, 2003, provisional application No. 60/482,081, filed on Jun. 23, 2003, provisional application No. 60/452,707, filed on Mar. 7, 2003.

(51) Int. Cl.
*C07K 1/00* (2006.01)

(52) U.S. Cl. ............... 530/350; 930/120

(58) Field of Classification Search ............ None
See application file for complete search history.

(56) References Cited

U.S. PATENT DOCUMENTS

| | | |
|---|---|---|
| 4,179,337 A | 12/1979 | Davis |
| 4,280,953 A | 7/1981 | Guillemin |
| 4,301,144 A | 11/1981 | Iwashita |
| 4,496,689 A | 1/1985 | Mitra |
| 4,640,835 A | 2/1987 | Shimizu |
| 4,670,417 A | 6/1987 | Iwasaki |
| 4,791,192 A | 12/1988 | Nakagawa |
| 5,089,261 A | 2/1992 | Nitecki |
| 5,183,550 A | 2/1993 | Mattiessen |
| 5,264,209 A | 11/1993 | Mikayama |
| 5,383,657 A | 1/1995 | Rathmell |
| 5,446,090 A | 8/1995 | Harris |
| 5,506,107 A | 4/1996 | Cunningham |
| 5,605,793 A | 2/1997 | Stemmer |
| 5,672,662 A | 9/1997 | Harris |
| 5,766,883 A | 6/1998 | Ballance |
| 5,766,897 A | 6/1998 | Braxton |
| 5,811,238 A | 9/1998 | Stemmer |
| 5,830,721 A | 11/1998 | Stemmer |
| 5,833,948 A | 11/1998 | Tournier |
| 5,837,458 A | 11/1998 | Minshull |
| 5,876,969 A | 3/1999 | Fleer |
| 5,900,461 A | 5/1999 | Harris |
| 5,919,455 A | 7/1999 | Greenwald |
| 5,932,462 A | 8/1999 | Harris |
| 5,981,200 A | 11/1999 | Tsien |
| 5,985,236 A | 11/1999 | Khan |
| 5,986,068 A | 11/1999 | Chappel |
| 5,990,237 A | 11/1999 | Bentley |
| 6,113,906 A | 9/2000 | Greenwald |
| 6,153,265 A | 11/2000 | Tomaru |
| 6,188,965 B1 | 2/2001 | Mayo et al. |
| 6,214,966 B1 | 4/2001 | Harris |
| 6,258,351 B1 | 7/2001 | Harris |
| 6,269,312 B1 | 7/2001 | Mayo et al. |
| 6,403,312 B1 | 6/2002 | Dahiyat |
| 6,413,507 B1 | 7/2002 | Bentley |
| 6,437,025 B1 | 8/2002 | Harris |
| 6,448,369 B1 | 9/2002 | Bentley |
| 6,495,659 B2 | 12/2002 | Bentley |
| 6,686,196 B2 | 2/2004 | Lieber |
| 6,708,120 B1 | 3/2004 | Mayo |
| 6,792,356 B2 | 9/2004 | Mayo et al. |
| 6,801,861 B2 | 10/2004 | Mayo et al. |
| 6,804,611 B2 | 10/2004 | Mayo |
| 6,864,359 B1 | 3/2005 | Luo |
| 6,950,754 B2 | 9/2005 | Mayo |
| 7,037,503 B2 | 5/2006 | Collier |
| 7,056,695 B2 | 6/2006 | Dahiyat et al. |
| 2001/0039480 A1 | 11/2001 | Mayo |
| 2002/0037286 A1 | 3/2002 | Krause |

(Continued)

FOREIGN PATENT DOCUMENTS

EP    0 311 589    4/1989

(Continued)

OTHER PUBLICATIONS

Alexandrov, "SARFing the PDB" *Protein Eng* 9(9): 727-32. (1996).
Altschul, et al., "Basic Local Alignment Search Tool," *J. Mol. Biol.* 215(3): 403-10 (1990).
Altschul, et al., "Gapped Blast and PSI-Blast: a new generation of protein database search programs," *Nucleic Acids Res.* 25: 3389-402 (1997).

(Continued)

*Primary Examiner*—Patricia A Duffy
(74) *Attorney, Agent, or Firm*—Morgan Lewis & Bockius LLP; Robin M. Silva, Esq.; David C. Foster, Esq.

(57) ABSTRACT

The invention relates to novel proteins with BAFF dominant negative antagonist, receptor antagonist activity and agonist activity and nucleic acids encoding these proteins. The invention further relates to the use of the novel proteins in the treatment of BAFF or APRIL-related disorders.

11 Claims, 18 Drawing Sheets

U.S. PATENT DOCUMENTS

| | | | |
|---|---|---|---|
| 2002/0040132 | A1 | 4/2002 | Brennand |
| 2002/0048772 | A1 | 4/2002 | Dahiyat et al. |
| 2002/0061525 | A1 | 5/2002 | Yelin et al. |
| 2002/0110868 | A1 | 8/2002 | Dahiyat |
| 2003/0130827 | A1 | 7/2003 | Desjarlais |
| 2003/0138401 | A1 | 7/2003 | Dahiyat |
| 2003/0166559 | A1 | 9/2003 | Desjarlais |
| 2003/0219864 | A1 | 11/2003 | Desjarlais |
| 2004/0249576 | A1 | 12/2004 | Desjarlais |

FOREIGN PATENT DOCUMENTS

| | | |
|---|---|---|
| EP | 0 400 472 | 5/1990 |
| EP | 0 424 405 | 5/1991 |
| EP | 0786 257 | 7/1997 |
| EP | 0 902 085 | 3/1999 |
| EP | 1 064 951 | 1/2001 |
| EP | 1 098 257 A2 | 5/2001 |
| EP | 0 544 826 | 1/2002 |
| EP | 1 255 826 | 9/2005 |
| WO | WO 87/05330 | 9/1987 |
| WO | WO 99/12965 A | 3/1999 |
| WO | WO 99/45026 | 9/1999 |
| WO | WO 99/51632 | 10/1999 |
| WO | WO 00/43032 A | 7/2000 |
| WO | WO 00/67034 A | 11/2000 |
| WO | WO 01/25277 | 4/2001 |
| WO | WO 01/41812 A2 | 6/2001 |
| WO | WO 01/49830 | 7/2001 |
| WO | WO 01/51510 | 7/2001 |
| WO | WO 01/51629 | 7/2001 |
| WO | WO 01/58493 | 8/2001 |
| WO | WO 02/02597 | 1/2002 |
| WO | WO 02/18445 AS | 3/2002 |
| WO | WO 02/18620 | 3/2002 |
| WO | WO 02/18620 A2 | 3/2002 |
| WO | WO 02/22149 A1 | 3/2002 |
| WO | WO 02/36141 A2 | 5/2002 |
| WO | WO 03/006154 A2 | 1/2003 |
| WO | WO 03/029420 A2 | 4/2003 |
| WO | WO 03/035846 | 5/2003 |
| WO | WO 03/035846 A2 | 5/2003 |
| WO | WO 03/057856 | 7/2003 |
| WO | WO 03/057856 A2 | 7/2003 |
| WO | WO 03/059281 A2 | 7/2003 |
| WO | WO 2004/081043 | 9/2004 |
| WO | WO 2004/081043 A2 | 9/2004 |
| WO | WO 2004/089982 A2 | 10/2004 |
| WO | WO 2005/035570 A2 | 4/2005 |

OTHER PUBLICATIONS

Ameloot, P., et al. "Heterotrimers Formed by Tumor Necrosis Factors of Different Species or Muteins" *J. Biol. Chem.* vol. 276, No. 29 pp. 27098-103(2001).

Anderson, et al., "Human Gene Therapy," *Science* 256: 808-13 (1992).

Aplin and Wriston, "Preparation, Properties, and Applications of Carbohydrate Conjugates of Proteins and Lipids," *CRC Crit. Rev. Biochem.*, pp. 259-306 (1981).

Brower, V., "Naked DNA vaccines come of age" *Nature Biotechnology*, 16: 1304-05 (1998).

Burge and Karlin, "Prediction of Complete Gene Structures In Human Genomic DNA" *J Mol Biol* 268(1): 78-94. (1997).

Chen et al., et al., "Construction and function of two Cys146-mutants with high activity, derived from recombinant human soluble B lymphocyte stimulator." *J. of Biochem* 136(1):73-79 (2004).

Creighton, T.E., *Proteins: Structure and Molecular Properties*, W.H. Freeman & Co., San Francisco, pp. 79-86 (1983).

Dahiyat, et al., "Automated design of the surface positions of protein helices," *Protein Science* 6: 1333-37 (1997).

Do, R., and Chen-Kiang, "Mechanism of BlyS action in B cell immunity," *C. Cytokine & Growth Factor Reviews* 2002, 13: 19-25.

Dzau, et al., "Gene Therapy for Cardiovascular Disease" *Trends in Biotechnology* 11: 205-10 (1993).

Edge, et al., "Deglycosylation of Glycoproteins by Trifluoromethanesulfonic Acid," *Anal. Biochem.*, 118: 131-37 (1981).

Evan, et al., "Isolation of Monoclonal Antibodies Specific for Human c-*myc* Proto-Oncogene Product," *Molecular and Cellular Biology*, 5: 3610-16 (1985).

Field, et al., "Purification of a *RAS*-Responsive Adenylyl Cyclase Complex from *Saccharomyces cerevisiae* by Use of an Epitope Addition Method," *Mol. Cell. Biol.* 8: 2159-65 (1988).

Goldenberg, et al., "Circular and Circularly Permuted Forms of Bovine Pancreatic Trypsin Inhibitor," *J. Mol. Biol.* 165: 407-13 (1983).

Groom, J., et al., "Association of BAFF/BlyS overexpression and altered B cell differentiation with Sjögren's syndrome," *The Journal of Clinical Investigation* 2002, 109: 59-68.

Gross, J., et al., "TACI and BCMA are receptors for a TNF homologue implicated in B-cell autoimmune disease." *Nature* 2000, 404: 995-99.

Harris, M.E., Pace, N.R., "Analysis of the tertiary structure of bacterial Rnase P RNA" *Mol Biol Rep*. 1995-96; 22(2-3): 115-23.

Heinemann U., Hahn M., "Circular Permutation of Polypeptide Chains: Implications for Protein Folding and Stability," *Prog. Biophys. molec. Biol.* 64(2-3): 121-43 (1995).

Hennecke, et al., "Random Circular Permutation of DsbA Reveals Segments that are Essential for Protein Folding and Stability", *J. Mol. Biol.*, 286: 1197-215 (1999).

Holm, et al., "Touring protein fold space with Dali/FSSP," *Nucleic Acid Res*. 26(1): 316-19 (1998).

Hong, Xia et al., et al., [Reply of Liu, et al. under "Brief Communications"] *Nature*, 427: 413 (2004).

Hopp, et al., "A Short Polypeptide Marker Sequence Useful for Recombinant Protein Identification and Purification," *BioTechnology* 6: 1204-10 (1988).

Kanakaraj, P. et al, "BlyS Binds to B Cells with High Affinity and Induces Activation of the Transcription Factors NF-κB and ELF-1,". *Cytokine*, 13, 25-31 (2001).

Karpusas, M., et al., "Cyrstal Structure of Extracellular Human BAFF, a TNF Family member that Sitmulates B Lymphocytes," *J. Mol.Biol.*, 315, 1145-54 (2002).

Kawasaki, A., et al. "Analysis on the association of human BLYS (BAFF, TNFSF13B) polymorphisms with systemic lupus erythematosus and rheumatoid arthritis," *Genes and Immunity*, 3: 424-29 (2002).

Kayagaki, N., et al., "BAFF/Blys Receptor 3 Binds the B Cell Survival Factor BAFF Ligand through a Discrete Surface Loop and Promotes Processing of NF-κB2," *Immunity*, 10, 515-24 (2002).

Khare, S. and Hsu, H. "The role of TALL-1 and APRIL in immune regulation" *TRENDS in Immunology*, 22: 61 (2001).

Kim, H.M., et al., "Crystal structure of the Baff-Baff-R complex and its implications for receptor activation," *Nature Struct. Biol.*, 10, 342-48 (2003).

Kinstler, et al., "Mono-N-terminal poly(ethylene glycol)-protein conjugates," *Advanced Drug Deliveries Reviews*, 54: 477-85 (2002).

Liu, Y. et al., "Crystal Structure of sTALLl-1 Reveals a Virus-like Assembly of TNF Family Ligands," *Cell*, 108, 383-94 (2002).

Liu, Y., et al., "Ligand-receptor binding revealed by the TNF family member TALL-1," *Nature*, 423: 49-56 (2003).

Luger, et al., "Correct Folding of Circularly Permuted Variants of a βα Barrel Enzyme in Vivo," *Science*, 243: 206-10 (1989).

Lutz-Freyermuth, et al., "Quantitative determination that one of two potential RNA-binding domains of the A protein component of the U1 small nuclear ribonucleoprotein complex binds with high affinity to stem-loop II of U1 RNA," *Proc. Natl. Acad. Sci. U.S.A.* 87: 6393-97 (1990).

Mackay, F. and Browning, "BAFF: A Fundamental Survival Factor for B Cells," *J. Nature Reviews Immunology* 2002, 2: 465-75.

Mackay, F. and Kalled, S. , "TNF ligands and receptors in autoimmunity: an update," *Current Opinion in Immunology* 2002, 14: 783-90.

Mackay, F. and Mackay, "The role of BAFF in B-cell maturation, T-cell activation and autoimmunity," *C. Trends in Immunology* 2002, 23: 113-15.

Martin, et al., "GAP Domains Responsible for Ras p21-Dependent Inhibition of Muscarinic Atrial K+ Channel Currents," *Science* 255: 192-94 (1992).

Martin, et al., "The affinity-selection of a minibody polypeptide inhibitor of human interleukin-6," *EMBO J.* 13(22): 5303-09 (1994).

Menart, V., et al., "Early events in TNFa—p55 receptor interactions—experiments with TNF dimmers," *Eur J Physiol.*, 439, R113-15 (2000).

Miyazawa, et al., "Estimation of Effective Interresidue Contact Energies from Protein Crystal Structures: Quasi-Chemical Approximation," *Macromolecules* 18: 534-52 (1985).

Moore, P., et al., "BlyS: Member of the Tumor Necrosis Factor Family and B Lymphocyte Stimulator," *Science* 285: 260-63 (1999).

Myszka, et al., "Design and Characterization of an Intramolecular Antiparallel Coiled Coil Peptide," *Biochem.* 33: 2363-72 (1994).

Nardulli, A.M., Shapiro D.J., "DNA Bending by Nuclear Receptors," *Receptor*, 3: 247-55 (1993).

Oren, D.A., et al., "Structural basis of BlyS receptor recognition," *Nature Struct. Biol.*, 9: 288-92 (2002).

Orengo and Taylor, "SSAP: Sequential Structure Alignment Program for Protein Structure Comparison," *Methods Enzymol* 266: 617-35 (1996).

Orengo, et al., "CATH—a heirarchic classification of protein domain structure," *Structure* 5(8): 1093-108 (1997).

Paborsky, et al., "Mammalian cell transient expression of tissue factor for the production of antigen," Protein Engineering, 3(6): 547-53 (1990).

Pan, T., "Probing RNA Structure and Function by Circular Permutation," *Methods Enzymol.* 317: 313-30 (2000).

Pan, T., Uhlenbeck, O.C., "Circularly permuted DNA, RNA and proteins—a review," *Gene*, 125: 111-14 (1993).

Pearce, et al., "Growth Hormone Binding Affinity for Its Receptor Surpasses the Requirements for Cellular Activity," *Biochemistry* 38: 81-89 (1999).

Press Release Xencor Determines Structure of BAFF, A Key Autoimmune Disease Target, Jan. 28, 2004.

Roberts, M.J., et al., "Chemistry of peptide and protein PEGylation," *Advanced Drug Delivery Reviews*, 54: 459-76 (2002).

Roschke, V., et al., "Blys and April Form Biologically Active Heterotrimers that are Expressed in Patients with Systemic Immune-Based Rheumatic Diseases," *The Journal of Immunology*, 169: 4314-21 (2002).

Schneider, P., et al., "BAFF, a Novel Ligand of the Tumor Necrosis Factor Family, Stimulates B Cell Growth," *The Journal of Experimental Medicine*, 189: 1747-56 (1999).

Seshasayee, D., et al., "Loss of TACI Causes Fatal Lymphoproliferation and Autoimmunity, Establishing TACI as an Inhibitory BlyS receptor," *Immunity*, 18: 279-88 (2003).

Shindyalov and Bourne, "Protein structure alignment by incremental combinatorial extension (CE) of the optimal path," *Protein Eng* 11(9): 739-47 (1998).

Skinner, et al., "Use of the Glu-Glu-Phe C-terminal Epitope for Rapid Purification of the Catalytic Domain of Normal and Mutant *ras* GTPase-activating Proteins," *J. Biol. Chem.* 266: 15163-66 (1991).

Sojar, "A Chemical Method for the Deglycosylation of Proteins," et al., *Arch. Biochem. Biophys.*, 259(1): 52-57 (1987).

Thotakura, et al., "Enzymatic Deglycosylation of Glycoproteins," *Meth. Enzymol.*, 138(28): 350-59 (1987).

Vaux, D. J., "The buzz about BAFF," *Clin. Investigation*, 109: 17-18 (2002).

Veronese, F.M., "Peptide and protein PEGylation: a review of problems and solutions," *Biomaterials*, 22: 405-71 (2001).

Wagner, et al., "Transferrin-polycation conjugates as carriers for DNA uptake into cells," *Proc. Natl. Acad. Sci. U.S.A.* 87: 3410-14 (1990).

Wheeler, et al., "Database Resources of the National Center for Biotechnology Information," *Nucleic Acids Res* 28(1): 10-14 (2000).

Wilken, et al., *Curr. Opin. Biotechnol.* 9: 412-26 (1998).

Wu, J. and Filutowicz, M., "Hexahistidine ($His_6$)-tag dependent protein dimerization: A cautionary tale," *Acta Biochim Pol.* 46: 591-99 (1999).

Yan, M., et al., "Identification of a receptor for BlyS demonstrates a crucial role in humoral immunity," *Nature Immunology*, 1: 37-41 (2000).

Yu, G., et al., "April and Tall-1 and receptors BCMA and TACI: system for reglating humoral immunity," *Nature Immunology*, 1: 252-56 (2000).

Zamecnik, et al., "Inhibition of replication and expression of human T-cell lymphotropic virus type III in cultured cells by exogenous synthetic oligonucleotides complementary to viral RNA," *Proc. Natl. Acad. Sci. U.S.A.* 83: 4143-46 (1986).

Zhang, et al., "In vivo formation of allosteric aspartate transcarbamoylase containing circularly permuted catalytic polypeptide chains: Implications for protein folding and assembly," *Protein Sci* 5, 1290-300 (1996).

Zhang, J., et al., "Cutting Edge: A Role for B Lymphocyte Stimulator i Systemic Lupus Erythematosus," *The Journal of Immunology*, 166: 6-10 (2001).

Zhukovsky, E., et al., "Is TALL-1 a trimer or a virus-like cluster?," *Nature*, 427: 413-14 (2004).

Gordon, et al "BAFF/BLys receptor 3 commprises a minimal TNF receptor-like module that encodes a highly focused ligand-binding site" Biochem.,2003,5977-5983, vol. 42, No. 20.

Patel, et al, "Engineering an APRIL-speficit B cell maturation antigen" J. Biol. Chem., 2004, 16727-16735, vol. 279, No. 16.

Kim, H.M., et al., "Crystal structure of the Baff-Baff-R complex and its implications for receptor activation," Nature Struct. Biol., 10, 342-48 (2003).

Chen et al., et al., "Construction and function of two Cys146-mutants with high activity, derived from recombinant human soluble B lymphocyte stimulator." J. of Biochem 136(1).

Gordon, et al "BAFF/BLys receptor 3 commprises a minimal TNF receptor-like module that encodes a highly focused ligand-binding site" Biochem.,2003,5977-5983, vol. 42, No. 20.

Patel, et al, "Engineering an APRIL-speficit B cell maturation antigen" J. Biol. Chem., 2004, 16727-16735, vol. 279, No. 16.

Liu, Y. et al., "Crystal Structure of sTALLI-1 Reveals a Virus-like Assembly of TNF Family Ligands," Cell, 108, 383-94 (2002).

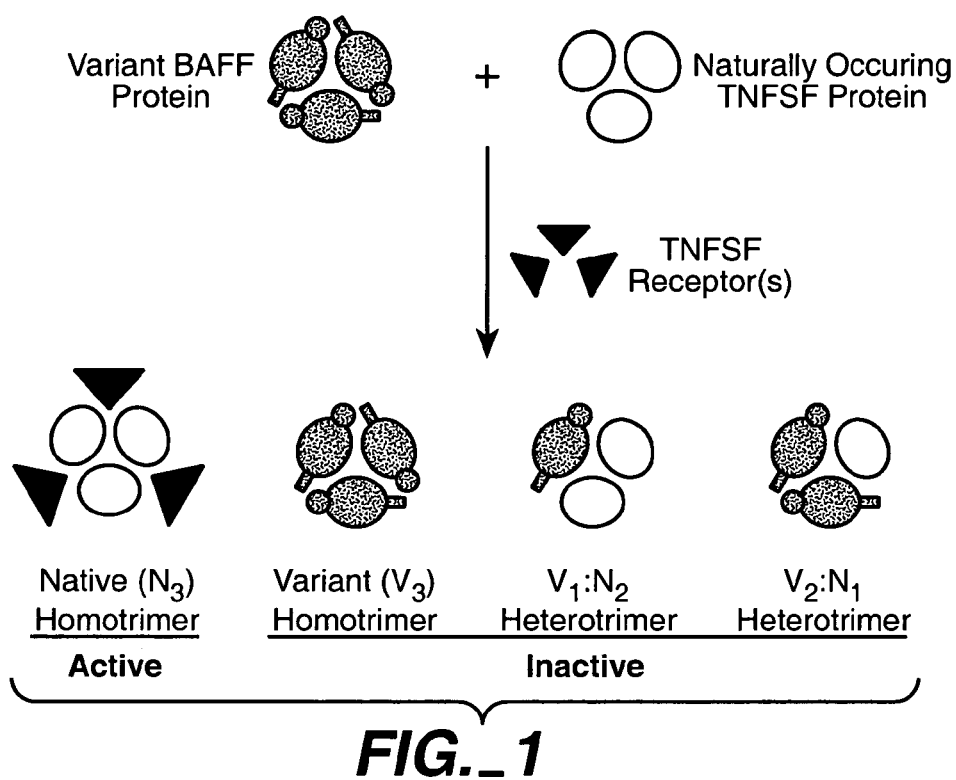
FIG._1

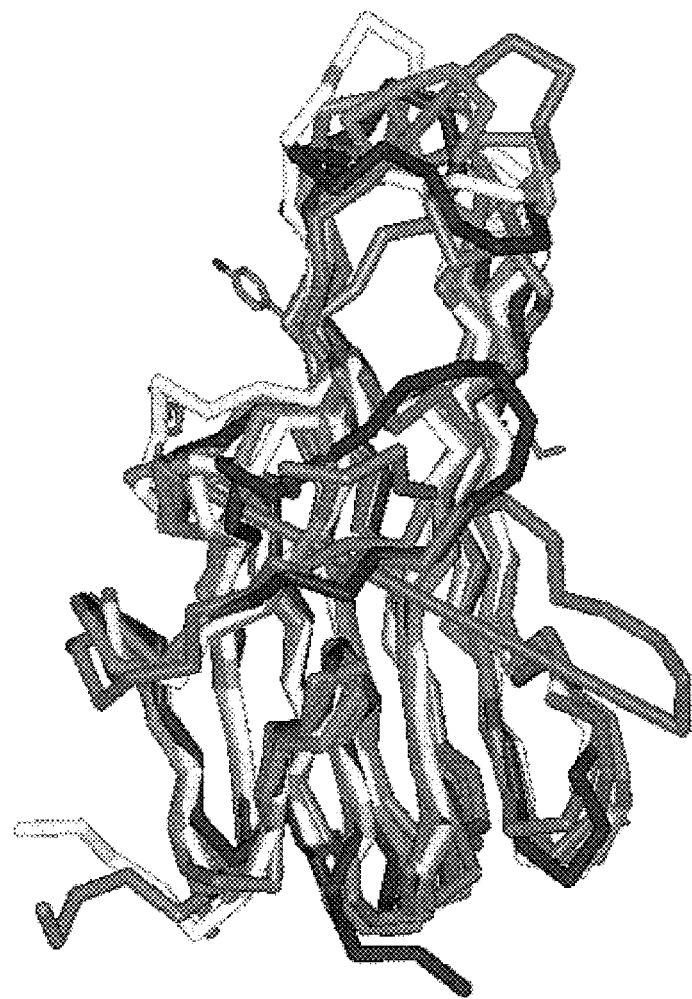
FIG._2

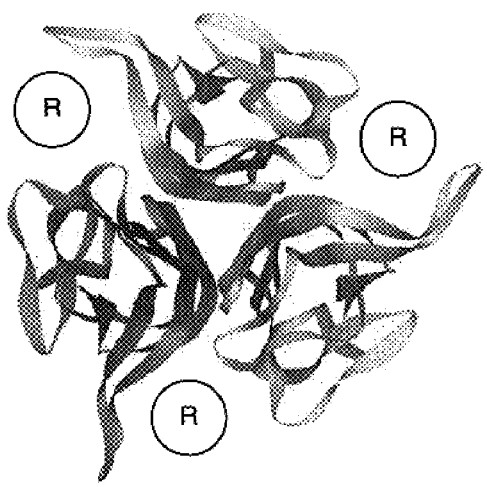 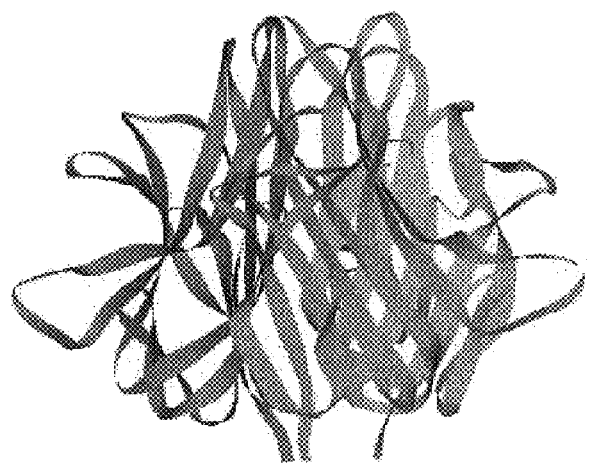
FIG._2A  FIG._2B

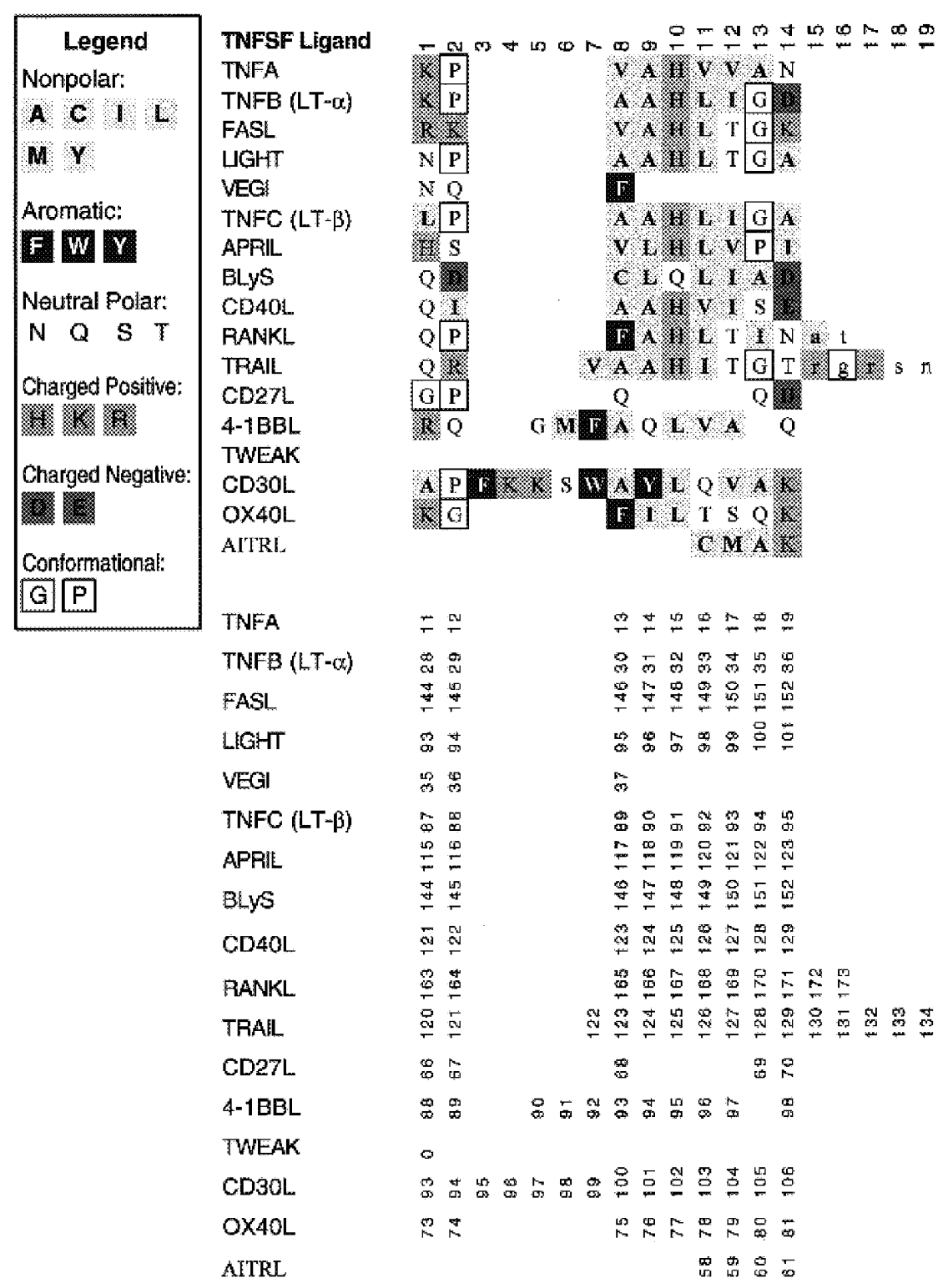

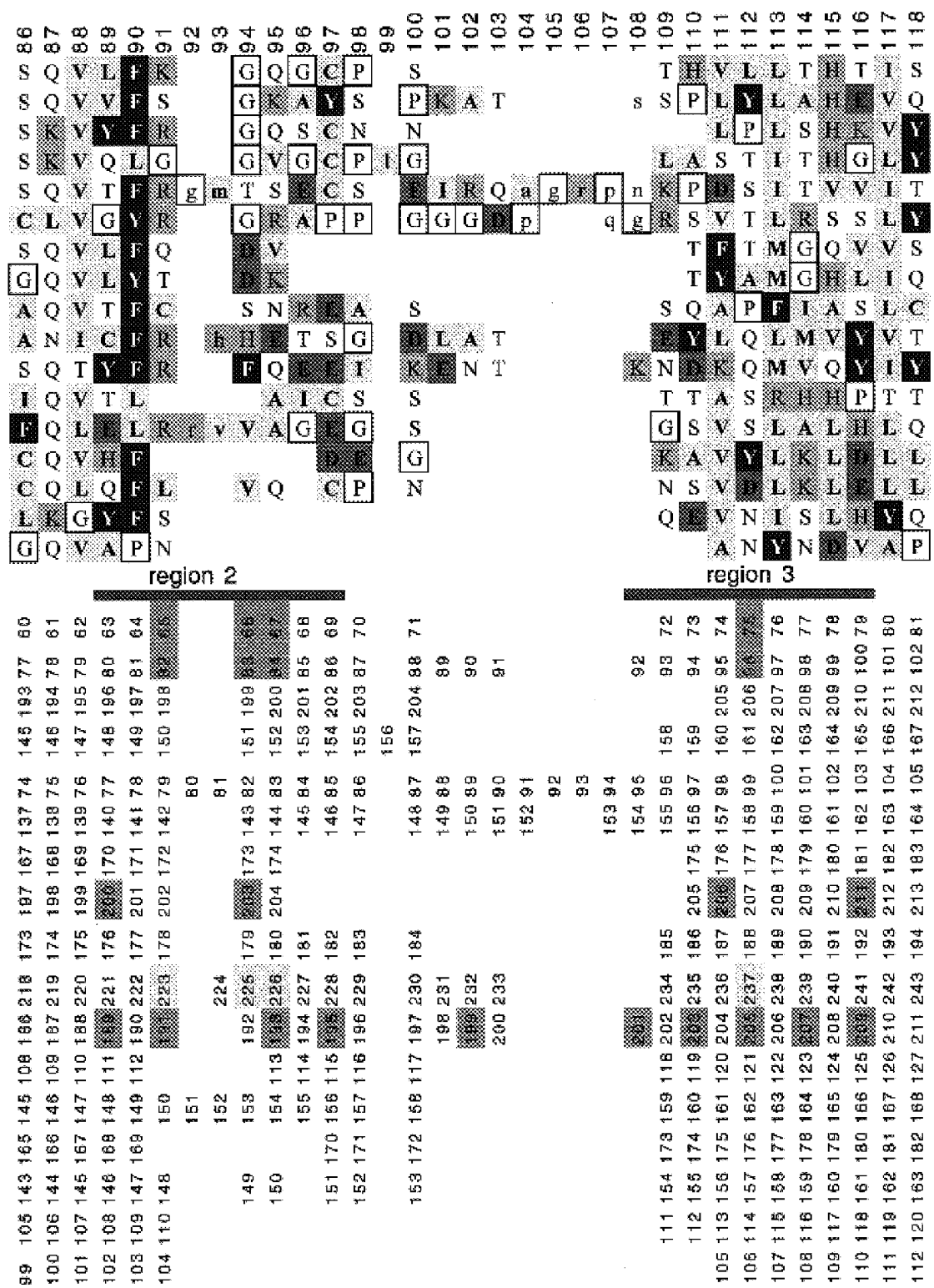
FIG._3D

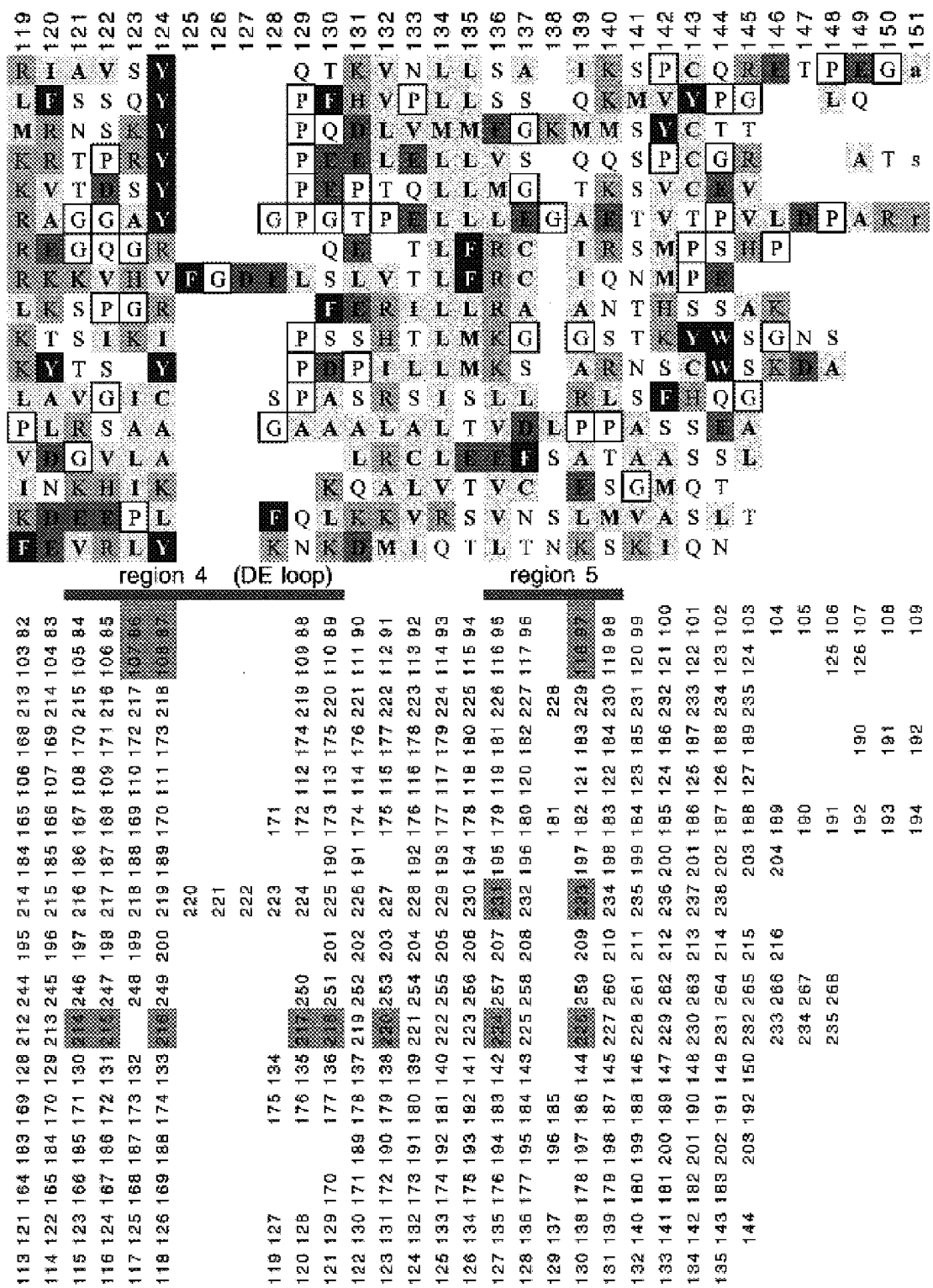
FIG._3E

FIG._3F

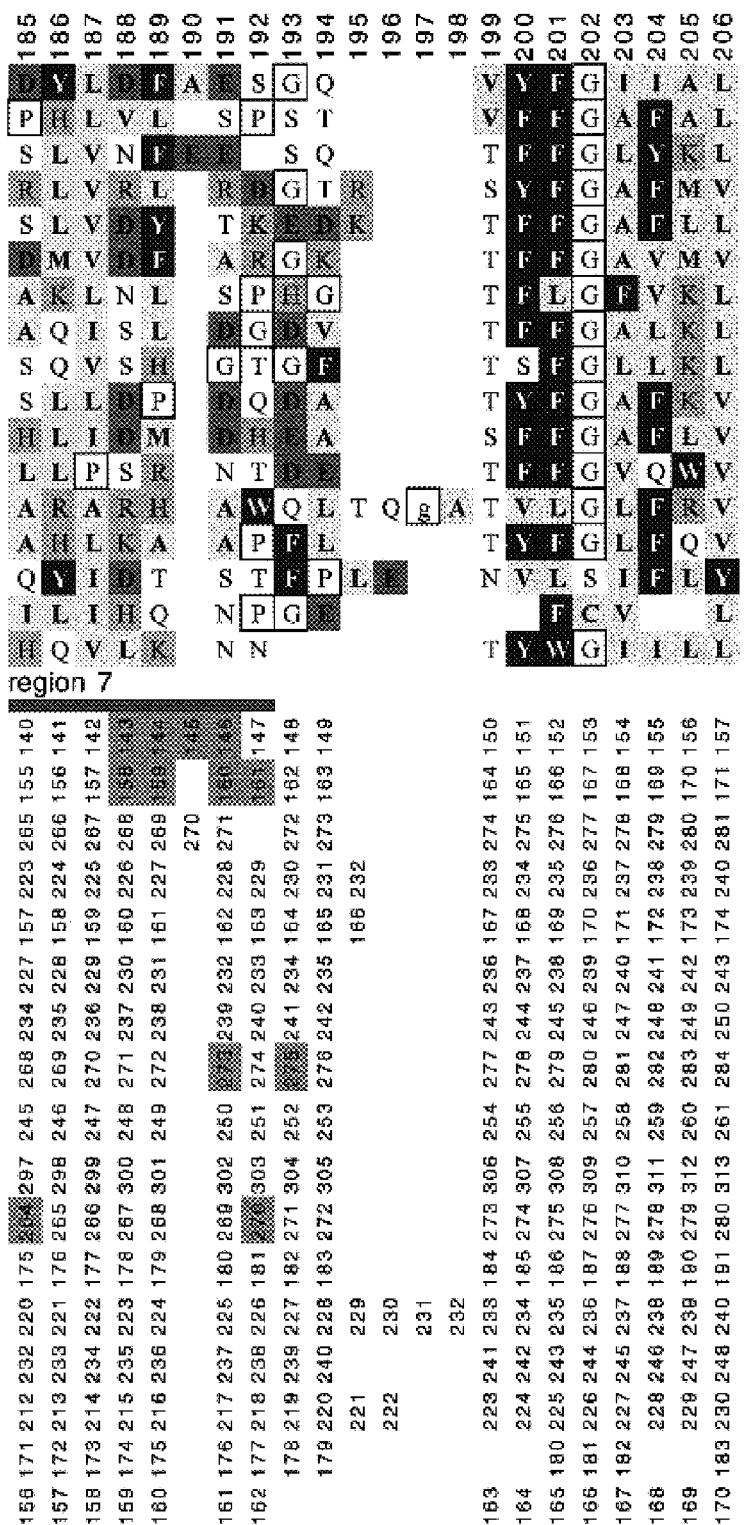
FIG._3G

| PDB Accession [Literature Reference] | N-Terminal Tag | Oligomerization State |
|---|---|---|
| 1KXG [3] | no tag | trimer |
| 1KD7 [2] | Myc-tag | trimer |
| 1JH5 [6] | His-tag | 60-mer |
| 1OQD / 1OQE [4] | His-tag | 60-mer |
| 1OTZ [5] | no tag | 60-mer* |
*Crystallized as 60-mer, but was purified as a BAFF trimer bound to three BAFF-R subunits.
*FIG._4*
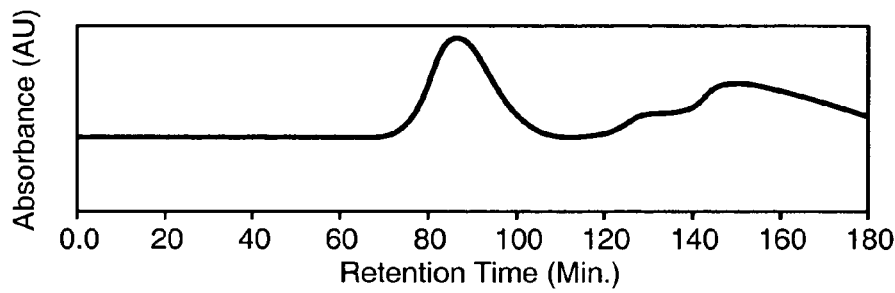
*FIG._5A*
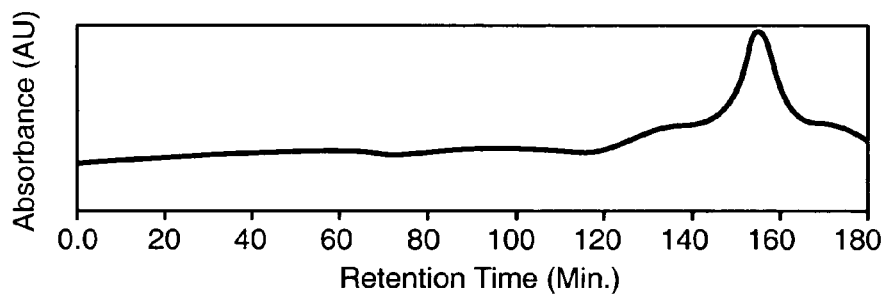
*FIG._5B*
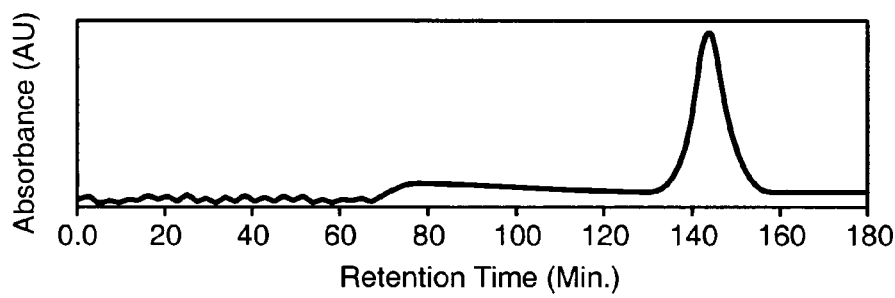
*FIG._5C*
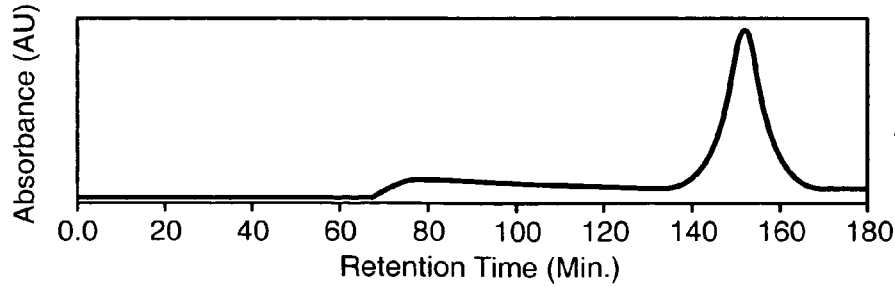
*FIG._5D*

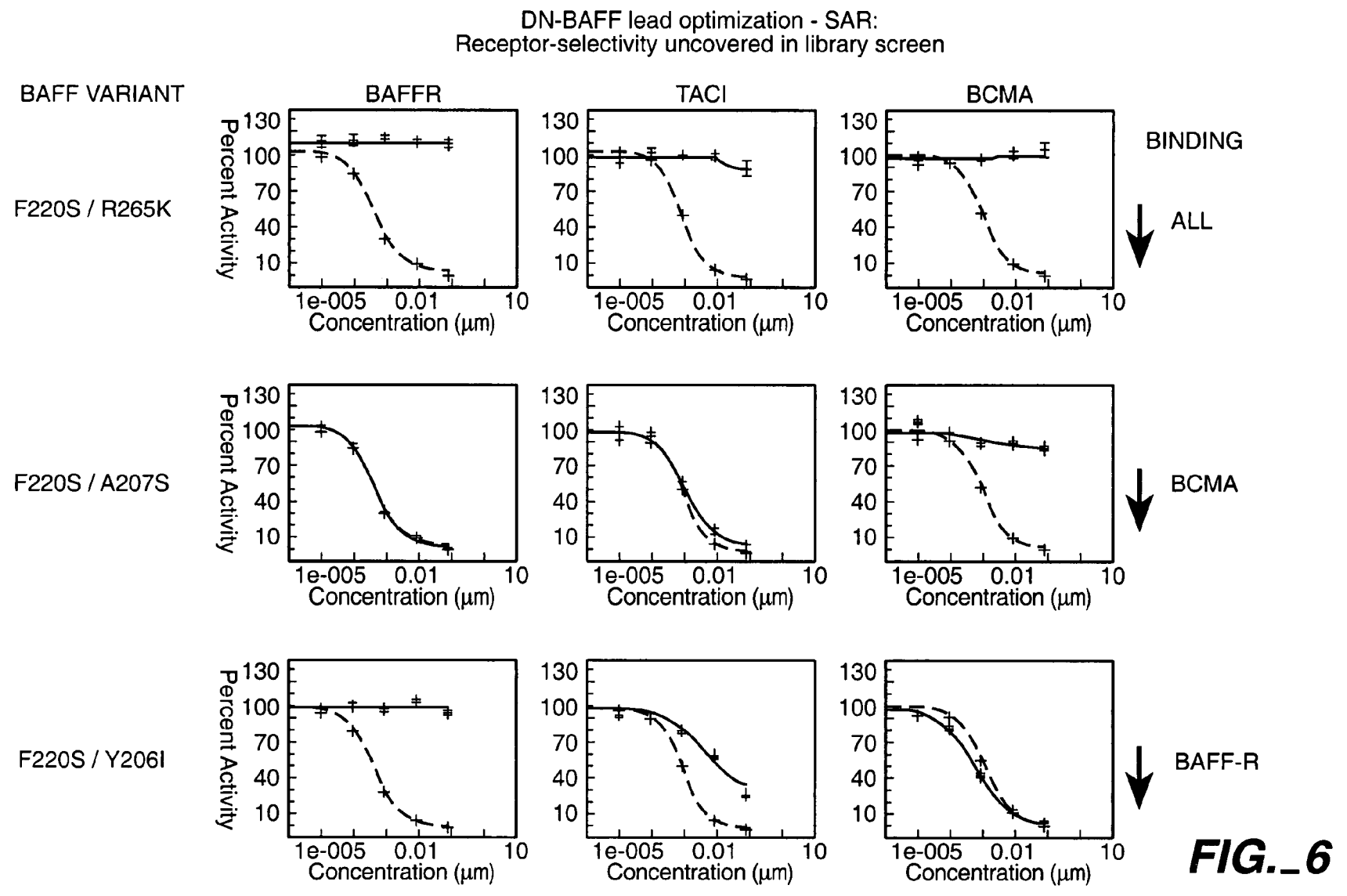

FIG._6

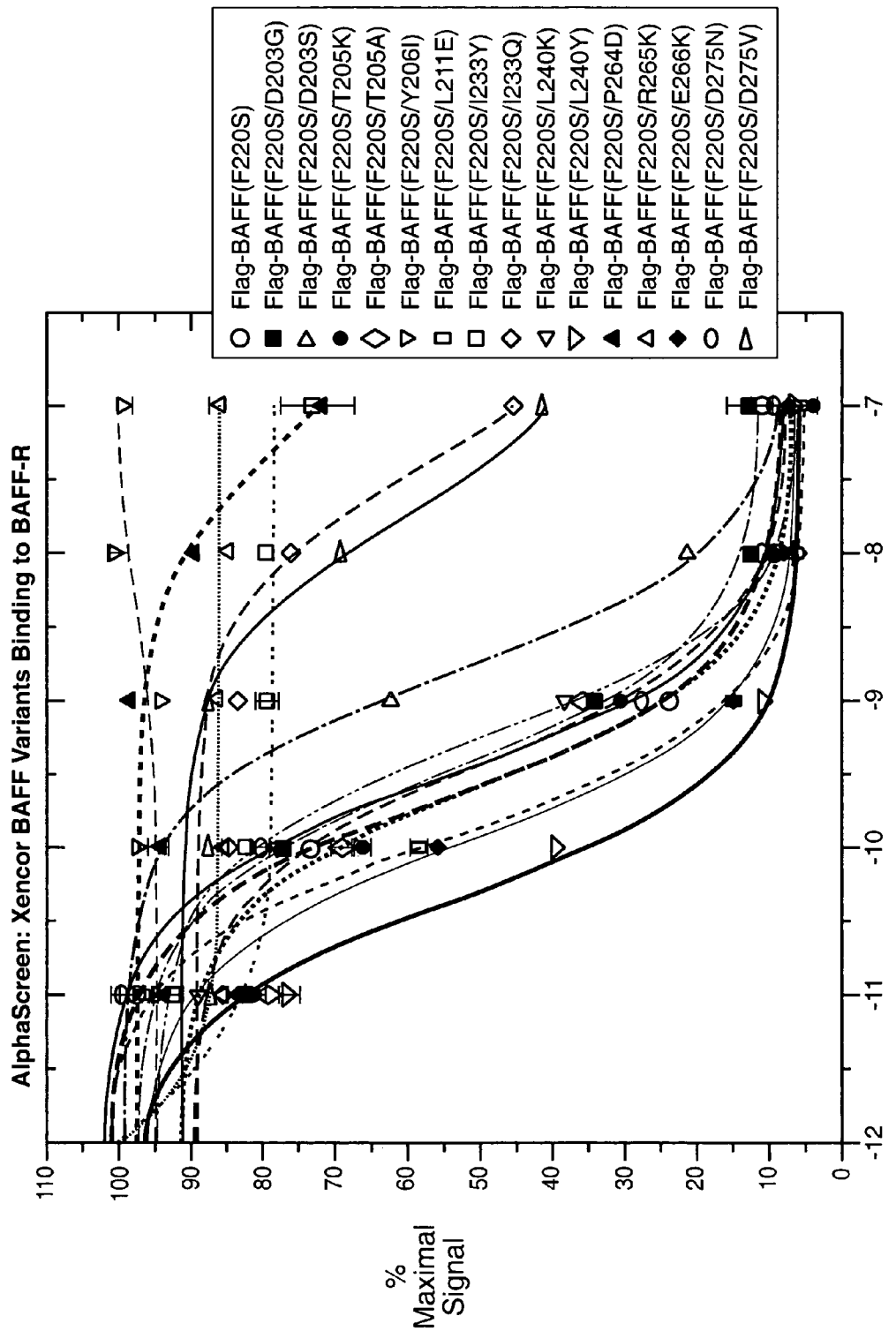
FIG._7

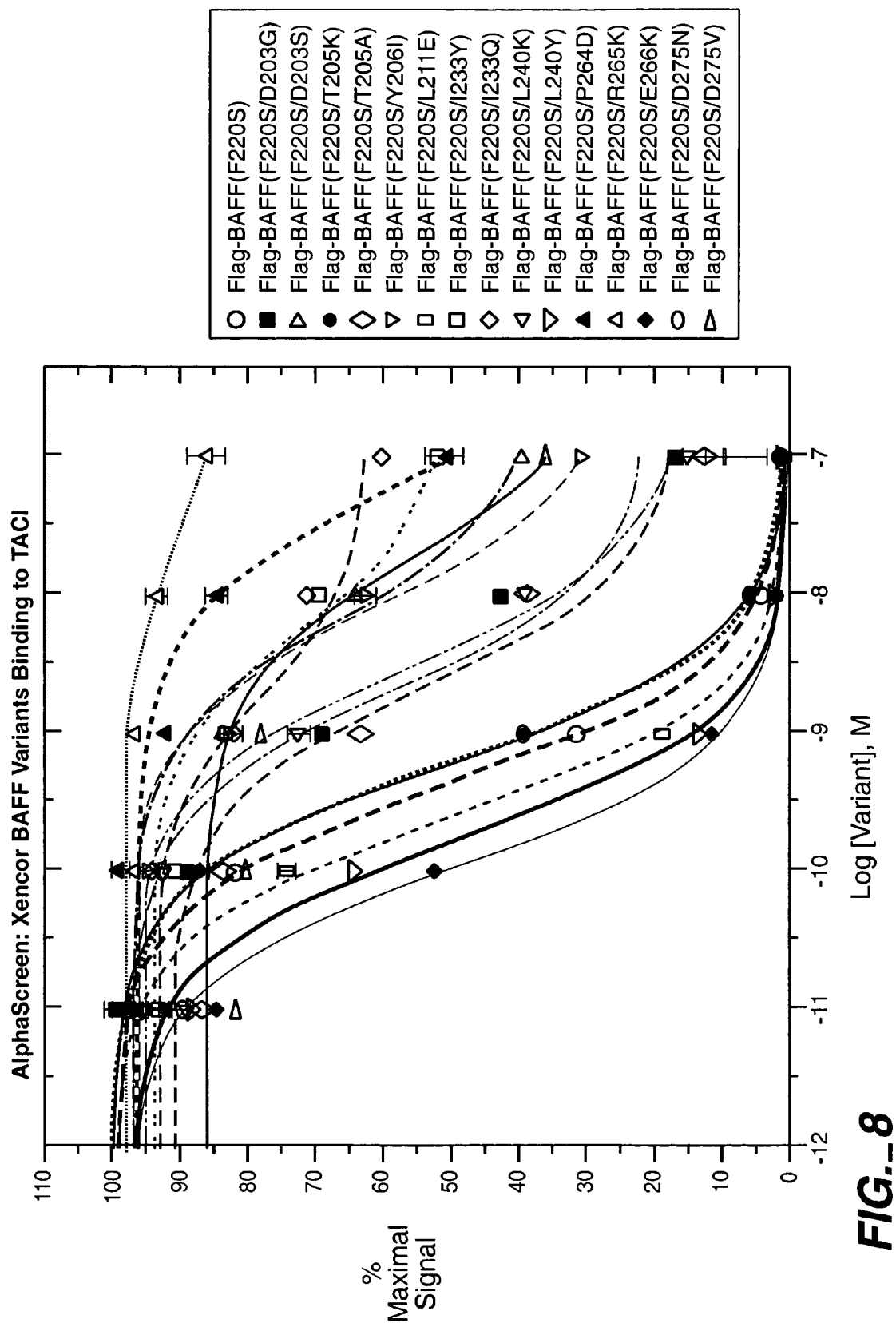
FIG._8

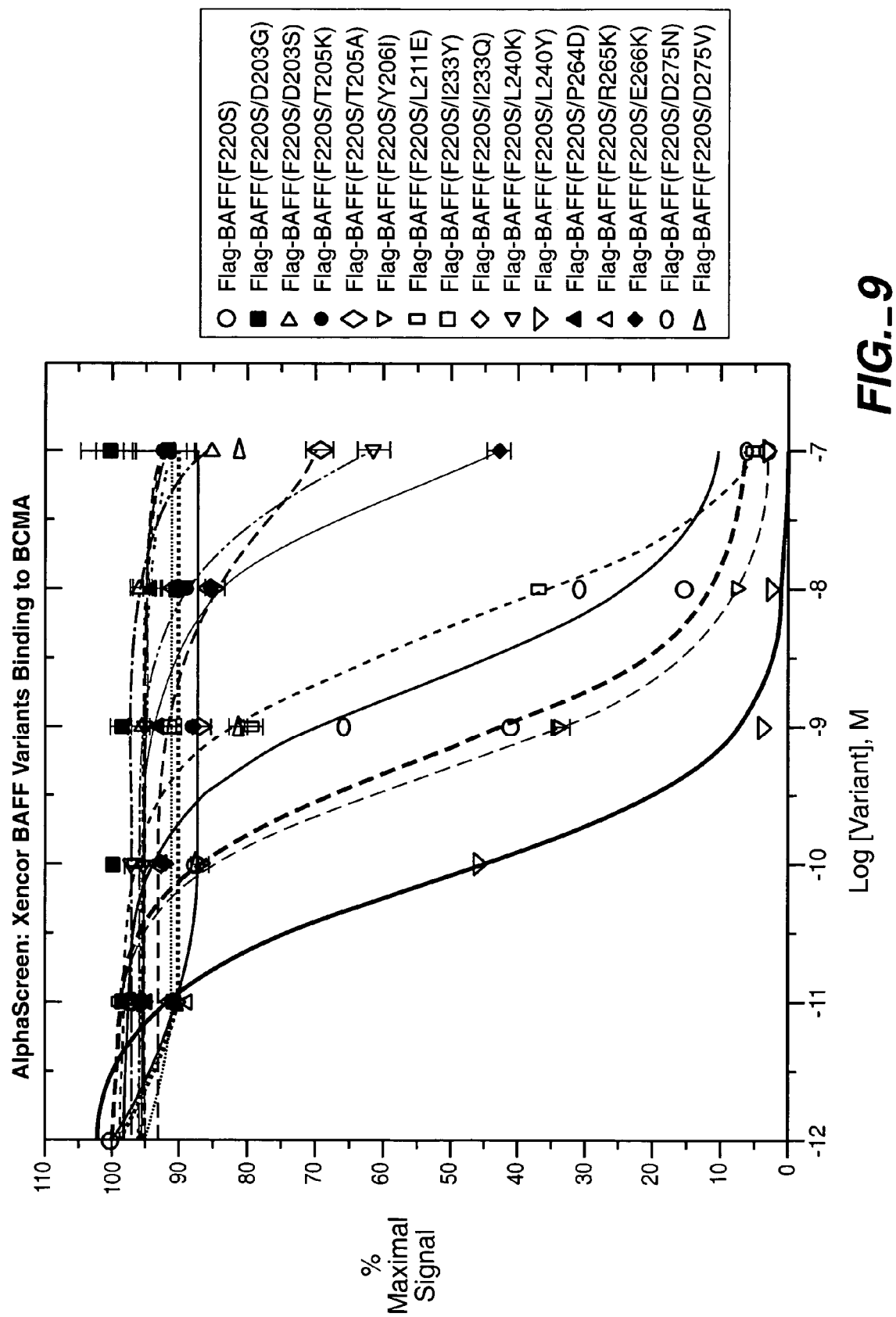
FIG._9

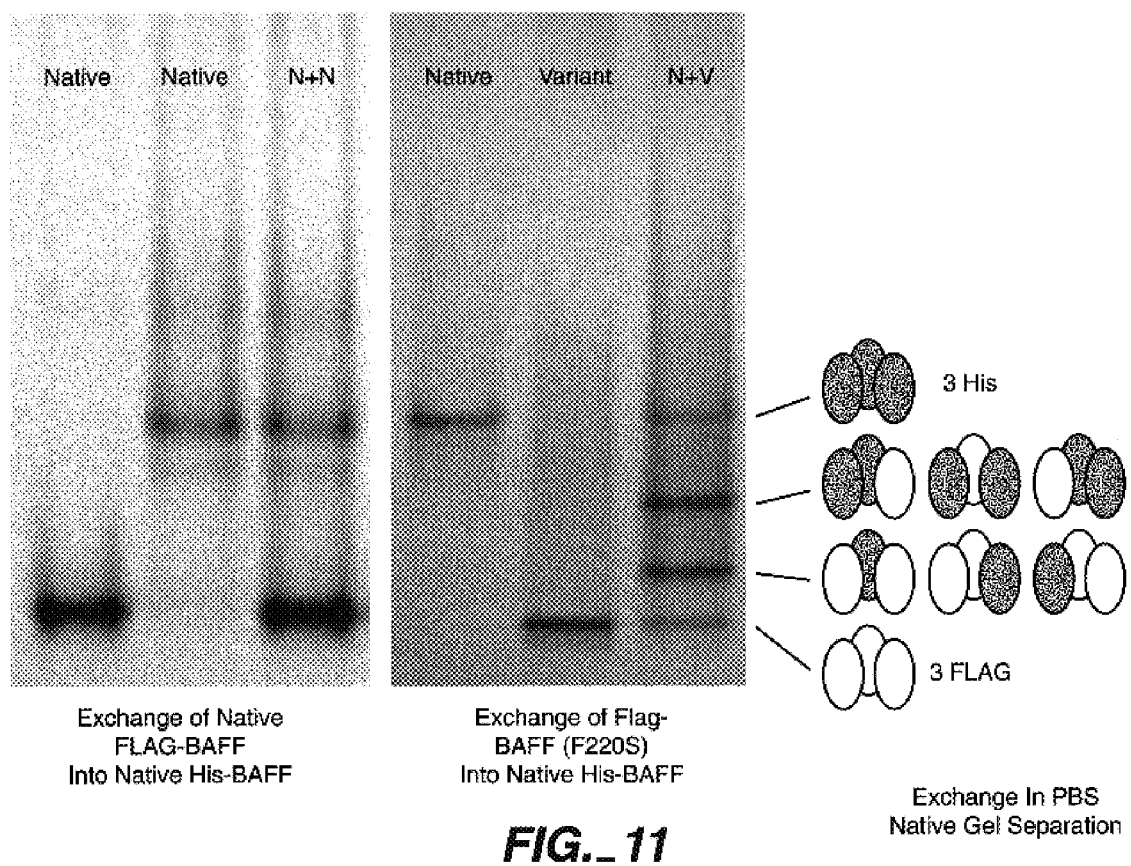
FIG._11

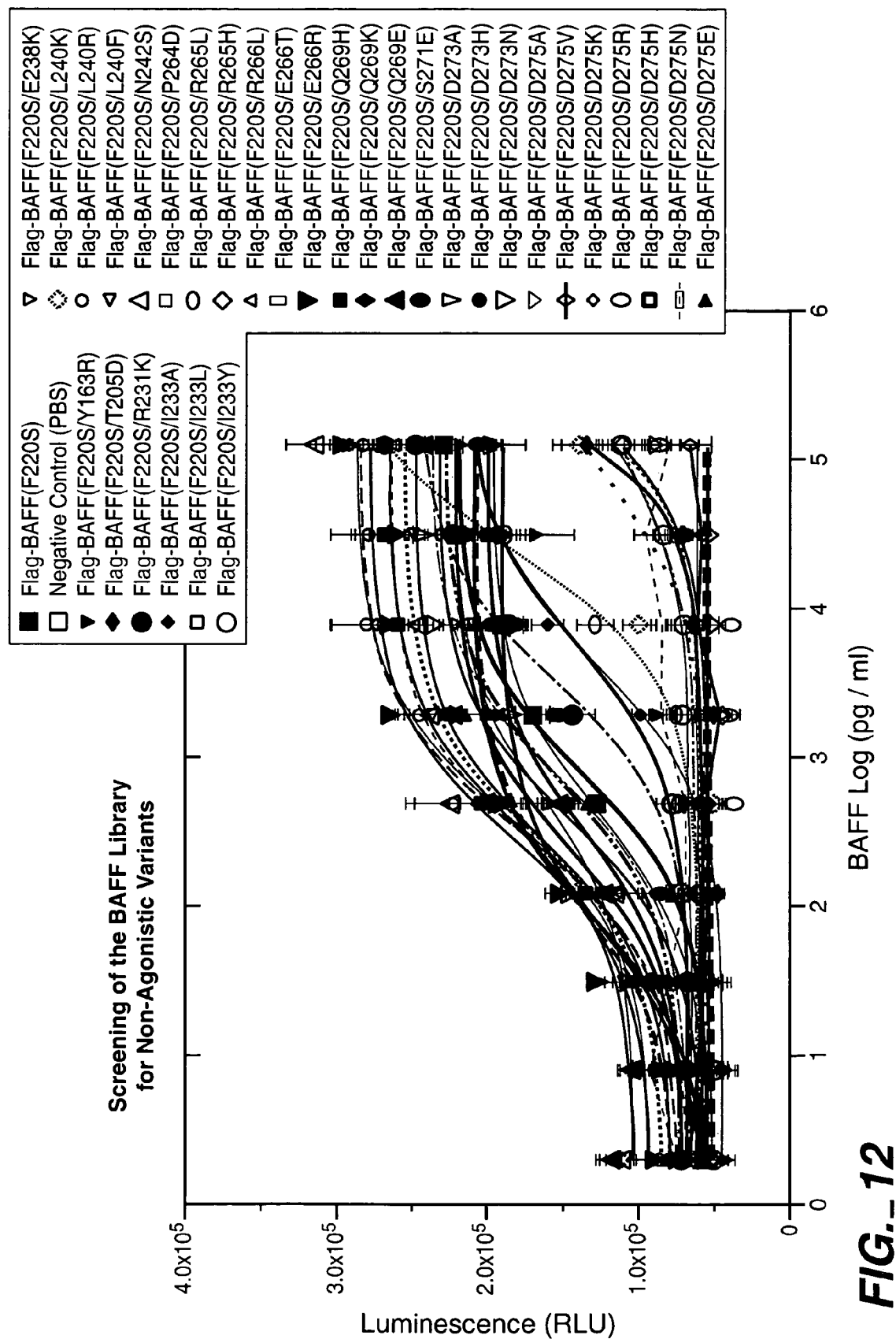
FIG._12

BAFF VARIANTS AND METHODS THEREOF

This application claims benefit under 35 U.S.C. §119(e) to U.S. Ser. Nos. 60/528,104, filed Dec. 8, 2003; 60/523,880, filed Nov. 20, 2003; 60/482,081, filed Jun. 23, 2003; 60/452,707, filed Mar. 7, 2003 and is a continuation-in-part of U.S. Ser. No. 10/338,083 filed on Jan. 6, 2003, all of which are expressly incorporated by reference in their entirety.

FIELD OF THE INVENTION

The invention relates to novel proteins of BAFF which modulate the signaling of naturally occurring BAFF and/or othe TNF super family (TNFSF) proteins with dominant negative antagonist activity, agonist activity, receptor antagonist activity (also known as competitive inhibition activity) and nucleic acids encoding these proteins. The invention further relates to the use of the novel proteins in the treatment of BAFF and/or TNFSF related disorders, such as pathologies of the immune system and oncological conditions.

BACKGROUND OF THE INVENTION

B-cell Activation Factor, BAFF (also known as BLyS, TALL-1, THANK, zTNF4 and TNFSF13B) and APRIL (also known as TRDL-1 alpha) are members of the TNF super family (TNFSF) of proteins. The prototype of the family, Tumor Necrosis Factor Alpha (TNFA), originally discovered for its in vivo effect causing tumors to regress, is a key mediator of inflammation. BAFF and APRIL proteins participate in a variety of cellular and intracellular signaling processes and are synthesized as a type 2 membrane proteins and fold into conserved β-pleated sheet structures. It is known that BAFF and APRIL form homotrimers typical of the TNFSF. In addition, BAFF and APRIL also form heterotrimers together.

The receptors for TNFSF members also represent a family of structurally related molecules, including at least 26 receptors and/or receptor decoy molecules. The extracellular domains of members of this family are composed of multiple repeats of a cysteine-rich domain (CRD), a small protein domain containing six conserved cysteines that form three disulfide bonds. The intracellular domains of these receptors are more diverse, although many members of the family contain a death domain that mediates apoptosis and other receptor signaling events. These members are all capable of inducing apoptosis via interaction with one or more intracellular adaptor molecules that also contain death domains. Other signaling receptors of this family signal via interactions with a family of adaptor molecules called TRAFs (TNF receptor associated factors). Signaling through BAFF receptors (for example, BAFFR, TACI and BMCA) is triggered by binding of an oligomeric (and for the most part, trimeric) BAFF ligand.

Recent reports have presented contradictory hypotheses regarding the functionally relevant oligomerization state of BAFF. As a member of the TNFSF of ligands, which are usually active as homotrimers, BAFF is hypothesized to function as a trimer and several reports support this hypothesis (See Kanakaraj, P. et al. *Cytokine,* 12, 25-31 (2001); Karpusas, M. et al. *J. Mol.Biol.,* 315, 1145-1154 (2002); Oren, D. A. et al. *Nature Struct. Biol.,* 9, 288-292 (2002); and Zhukovsky, E. et al., *Nature,* 427, 413 (2004)). However, X-ray crystallography and size exclusion chromatography (SEC) results recently reported (Liu, Y, et al. *Nature,* 423, 49-56, (2003); Liu, Y, et al., *Nature,* 427, 413 (2004) and Kim, H. M. et al. *Nature Struct. Biol.,* 10, 342-348 (2003)) indicate that BAFF forms 60-mer structures resembling the viral capsid of Satellite Tobacco Necrosis Virus (Liu, Y. et al. *Cell,* 108, 383-394 (2002)). A strong pH dependence of oligomerization state was observed: at pH 6.0 BAFF was 100% trimeric and at pH 7.4 100% 60-mer. It has been proposed that the higher order species represented the active form of BAFF and that the unusually long D-E loop facilitates formation of oligomers. These higher order species would represent novel cytokine architecture. Comparison of BAFF protein constructs reported in the literature reveals that various affinity tags have been used. Previous reports showed that fusion tags may affect oligomerization state of host proteins (Wu, J. and Filutowicz, M. *Acta Biochim Pol.* 46, 591-599 (1999).) All references cited herein are expressly incorporated in their entirety.

The three-dimensional structures of BAFF and APRIL are made up of a sandwich of two anti-parallel beta-sheets with the "jelly roll" or Greek key topology and it assembles into a trimeric complex. The cognate receptors of BAFF and APRIL are part of the related TNFSF of receptors. Furthermore, there appears to be significant conservation of the mode of receptor binding. In general, each receptor monomer binds within the cleft formed between two of the ligand monomers. The overall similarity in tertiary and quaternary structures of both the ligands and their complexes with receptors indicates that well-proven strategies for inhibition or agonism of one ligand-receptor system may be transferable to the other proteins in the family. Thus the present invention provides methods for the creation of variants of BAFF that are modulators of BAFF, APRIL and/or TNFSF signaling pathways.

Lymphocyte populations are regulated by replication and death. B-cell maturation relies on signals through both BCR (B-cell receptor) and survival co-stimulation by BAFF. Therefore, BAFF is important for survival of B-cells and humoral immune response. Normally, only a small number of B-cells mature due to a vigorous selection directed at selecting of a population of B-cells that are not auto reactive. Overexpression of BAFF in transgenic (Tg) animals results in the state of immune hyperreactivity, which is manifested in an increase of peripheral B-cell lymphocyte counts, breakdown of B-cell tolerance (inappropriate survival of autoreactive lymphocytes), and enlarged lymphoid organs and spleen. All this is accompanied by the appearance of anti-DNA antibodies, an increase in antibody secretion (e.g., IgM, IgG and IgA), and Ig-deposition in the kidneys resulting in glomerulonephritis that leads to autoimmune-like syndromes similar to systemic lupus erythematosus (SLE), Sjogren syndrome (SS), and the like. It has also been observed that SLE, RA, and SS patients showed a correlation of high BAFF concentration with elevated levels of anti-dsDNA Ab, a biochemical marker of these diseases. It has been shown that in RA patients, concentration of BAFF in synovial fluids is much higher than in blood.

BAFF also stimulates T-cells to a much lesser degree and increases the population of activated effector T-cells. There are three known receptors of BAFF: BAFF-R, TACI, and BCMA. The first one is exclusively specific to BAFF and the latter two are shared with APRIL, another member of TNFSF and the closest homologue of BAFF. Phenotypes of BAFF knockout mice (KO) and BAFF-R mutation strain of mice (ANVySnJ) suggest that BAFF-R is the main receptor for BAFF and is responsible for control of B-cell maturation. TACI controls B-cell homeostasis and T-cell Independent immune response and appears to act as an inhibitory BAFF receptor. The role of BCMA is unclear thus far.

The therapeutic interest in BAFF as a drug target lies in its strict specificity so that attenuation of the function of this cytokine may result in no widespread side effects. Animal studies have shown that administration of BAFF-blocking reagents in BAFF Tg mice reduced diseases incidence and its severity pointing to this cytokine as a crucial mediator of theses autoimmune diseases. For example, TACI-Fc inhibited the development of proteinuria and prolonged survival of NZB/WF1 mice (the main SLE model in mice).

APRIL is expressed in the same type of cells as BAFF, that is peripheral blood lymphocytes (PBL) and monocytes/macrophages. Similar to BAFF, APRIL also co-stimulates (together with BCR) B-cell proliferation and IgM production. APRIL KO mice die in utero suggesting that it may play an important role in development. BCMA preferentially binds to APRIL over BAFF.

APRIL stimulates colon cancer cells that express no TACI or BCMA (i.e. neither of the known APRIL receptors). In a similar assay, BAFF has no effect on tumor cells. Also, s-BCMA, which can bind and block APRIL, inhibited cancer cell growth. All these facts taken together suggest the existence of a specific APRIL-R that has not been identified yet.

A need still exists for proteins that can interfere with intracellular signaling processes. Thus, it is an object of the present invention to provide proteins comprising BAFF variants with BAFF receptor-interaction domains that are modified such that each domain has significantly reduced affinity and/or signaling capacity for the one or more cognate receptor(s). Such modified domains preferably retain association with individual monomer domains of naturally occurring BAFF or APRIL, but exhibit a dominant-negative phenotype, antagonizing the action of related naturally occurring domains via their sequestration into inactive oligomeric complexes. In another embodiment, BAFF homotrimers or homodimers may bind to one or more cognate receptors, including but not limited to BAFF-R, BCMA and TACI, and inactivate or reduce one or more intracellular signaling processes. In a further embodiment, BAFF variant homo-oligomers may act as agonists or superantagonists of one or more cognate receptors.

SUMMARY OF THE INVENTION

In accordance with the objects outlined above, the present invention provides variants of extracellular domains of BAFF proteins that modulate the signaling of naturally occurring BAFF and/or APRIL proteins.

The present invention provides variant BAFF proteins comprising an amino acid sequence that have at least one modification as compared to the naturally occurring BAFF protein sequence. In a preferred embodiment, variant BAFF proteins will physically interact with a naturally occurring BAFF or APRIL protein to form mixed oligomers substantially incapable of activating receptor signaling.

In another embodiment, variant BAFF proteins of the invention are in at least monomeric form and comprise amino acid sequences that have at least one modification as compared to a naturally occurring BAFF protein sequence, wherein said variant BAFF proteins will interact with a receptor interface at at least one receptor binding site to render said receptor substantially incapable of activating receptor signaling.

Preferably, a variant BAFF protein of the present invention has at least one receptor contact domain that has reduced affinity for a desired receptor as compared to its corresponding wild-type BAFF protein and retains the ability to interact with other receptor interaction domains.

More specifically, variant BAFF proteins of the present invention physically interact with a naturally occurring BAFF or APRIL protein to reduce the ability of the naturally occurring protein to activate at least one receptor. Variant BAFF proteins of the present invention may interact with other members of the TNFSF.

More specifically, variant BAFF proteins comprise at least one modified receptor-contact domain that has reduced affinity and/or signaling capacity for a desired receptor wherein said protein cannot substantially activate the desired receptor, but retains the ability to interact with other BAFF or APRIL proteins.

In a preferred embodiment, variant BAFF proteins have reduced affinity and/or signaling capacity for one or more receptors while maintaining or increasing signaling through one or more alternative receptors. For example, variant BAFF proteins that have reduced signaling thorugh BAFF-R and BCMA while maintaining signaling through TACI are expected to be potent antagonists of BAFF-mediated biology.

The present invention relates to the use of variants of BAFF for the inhibition or treatment of a variety of diseases. The variants are specifically engineered to modulate their biological signaling capacity, while retaining their ability to function as oligomeric species, either in complex with themselves or with naturally occurring members of the SF.

In a preferred embodiment, variant BAFF proteins are engineered to yield significantly reduced signaling through BAFF receptors compared to wild-type BAFF proteins while maintaining affinity for other BAFF or APRIL proteins to allow formation of mixed oligomers, most preferably trimers. Such variant BAFF proteins are referred to as "dominant negative BAFF variants" or"DN-BAFF". The dominant negative BAFF variants act by sequestering one or more naturally occurring BAFF or APRIL proteins in heterotrimers that are incapable of appreciably activating biological signaling through one or more cognate receptors. Consequently, DN-BAFF proteins act to antagonize the action of naturally occurring BAFF and/or APRIL.

In another embodiment, variant BAFF proteins are engineered to act as agonists. These agonist variants may find use in treating a variety of immune deficiency syndromes, including but not limited to common variable immunodeficiency (CVID) and immunoglobulin-A (IgA) deficiency. Additionally, conditions or diseases requiring elevated immune response or an increased number of B-cells, elevated concentrations of immunoglobulins would benefit from BAFF agonism (e.g. AIDS, cancer, infections, etc.). In a preferred embodiment, the variant BAFF proteins having modulated agonist activity may have modifications made either individually or in combination, with any combination being possible at amino acid residues at positions 159, 162, 163, 203, 204, 205, 206, 207, 211, 228, 231, 233, 238, 240, 242, 264, 265, 266, 267, 269, 271, 273 and 275.

It is a further embodiment to provide BAFF variants that provide a reduction in agonism comprising the following more preferred positions: Q159, Y163, D203, K204, T205, Y206, A207, L211, T228, R231, I233, P264, R265, E266, N267, S271, and D275, and more preferably, D203, T205, Y206, I233, P264, R265, and D275. In a further embodiment, the following substitutions are preferred: Q159E, Q159D, Y163E, Y163K, Y163R, D203S, D203N, D203E, K204E, K204Q, T205A, T205K, T205N, T205S, T205D, T205L, Y206A, Y206E, Y206K, Y206Q, Y206S, Y206I, A207S, L211K, L211D, T228N, T228V, R231K, I233A, I233E, I233T, I233Q, I233Y, 264N, 264D, 264A, R265A, R265K, R265L, R265H, E266Q, E266D, N267S, S271R, D275A, D275V, D275K, D275R, D275H, and D275N, and more preferably: D203N, T205D, Y206A, Y206E, Y206K, Y206Q, Y206S, Y206I, I233E, I233Q, I233Y, P264D, R265A, R265K, R265H, D275A, D275V, D275K, D275R, D275H, and D275N.

It is a further embodiment to provide BAFF variants that provide an increase in agonism, or a superagonist, comprising at least one of the following positions: T205, Y206, A207, L211, I233, E238, L240, N242, E266, N267, Q269, and D273. In another embodiment, at least one of the following BAFF variants provides superagonistic activity: Q159K, Q159R, S162N, S162L, S162D, Y163A, Y163H, Y163T, Y163F, Y163L, Y163I, T205I, Y206F, A207T, L211V, L211E, I233V, E238Q, E238K, L240N, L240R, L240Y, L240F, N242Y, E266T, E266K, E266I, N267R, Q269H, Q269K, D273A, and D273E.

In a further embodiment, variant BAFF proteins, in monomer or dimer form, are engineered to bind to a receptor but to reduce or eliminate signaling of the BAFF receptor.

In yet another embodiment, the BAFF variants of the present invention may be used as an experimental tool to identify molecules that interact with it in the signal transduction pathway associated with BAFF.

The present invention provides non-naturally occurring variant BAFF proteins (e.g. proteins not found in nature) comprising amino acid sequences with at least one modification compared to the wild-type BAFF proteins.

Preferred embodiments utilize variant BAFF proteins that interact with one or more wild-type TNFSF members to form mixed oligomers incapable of substantially activating receptor signaling. Preferably, variant BAFF proteins with at least one amino acid change are used as compared to a wild-type BAFF protein.

In another preferred embodiment, modifications may be made either individually or in combination, with any combination being possible. Preferred embodiments utilize at least one, and preferably more, positions in each variant BAFF protein. For example, amino acid substitutions may be combined to form double variants or triple point variants.

In a further embodiment, a BAFF molecule may be chemically modified, for example by PEGylation, phosphorylation or glycosylation.

In another aspect, portions of the N— or C— termini may be deleted. In a further embodiment, a BAFF molecule may be circularly permuted.

In an additional aspect, the two or more extracellular domains of the variant BAFF proteins are covalently linked by a linker peptide or by other means. Preferably, the linker peptide is a sequence of at least one and not more than about 30 amino acid residues and comprises one or more of the following amino acid residues: Gly, Ser, Ala, or Thr.

In a further aspect, the invention provides recombinant nucleic acids encoding the non-naturally occurring variant BAFF proteins, expression vectors, and host cells.

In an additional aspect, the invention provides methods of producing a non-naturally occurring variant BAFF protein comprising culturing the host cell of the invention under conditions suitable for expression of the nucleic acid.

In a further aspect, the invention provides pharmaceutical compositions comprising a variant BAFF protein of the invention and a pharmaceutical carrier.

In a further aspect, the invention provides methods for treating a BAFF related disorder comprising administering a variant BAFF protein of the invention to a patient.

In a further aspect, the invention provides methods to select and test fusion tags (e.g., His, Flag, 3×Flag, Myc, HA-tag, HSV, V5, KT3, GST, MBP, CBD, VSV-G, GFT, CAT, tubulin peptide, T7 gene 10 protein peptide, thioredoxin, beta-gal, luciferase, etc.) for each protein system to ensure that the tags do not perturb the physical chemical properties of the host protein.

It is an object of the present invention to provide non-naturally occurring variants of BAFF that have reduced BAFF-R binding. In a further object, the variants comprise at least one of the following positions: Q159, Y163, D203, T205, Y206, A207, L211, R231, I233, P264, R265, and D275, more preferably D203, T205, Y206, I233, R265, and D275. More particularly, the variants comprise at least one of the following substitutions: Y206A, Y206E, Y206K, Y206I, I233E, I233Y, R265K, Y206S, R265A, R265H, T205D, D275R, Y206Q, D203N, D275K, I233Q, D275H, T205N, D275V, P264N, D275A, P264D, P264A, R265L, D275N, D203E, L211K, L211D, D203S, I233T, Q159D, R231K, Y163R, T205S, A207S, T205A, and I233A, and more preferably, at least one of the following substitutions: D203N, T205D, Y206A, Y206E, Y206K, Y206Q, Y206S, Y206I, I233E, I233Q, I233Y, R265A, R265K, R265H, D275K, D275R, and D275H.

It is an object of the present invention to provide non-naturally occurring variants of BAFF that have increased BAFF-R binding. In a further object, the variants comprise at least one of the following positions: Q159, S162, Y163, D293, L211, I233, E238, L240, N242, E266, and Q269. More preferably, at least one of the following substitutions comprises the non-naturally occurring BAFF: Q159R, S162N, S162D, Y163T, Y163F, Y163L, Y163I, D203K, L211V, L211E, I233L, I233V, E238Q, E238K, L240N, L240R, L240Y, L240F, N242A, 266A, E266L, E266T, E266I, Q269K, and Q269E It is an object of the present invention to provide non-naturally occurring variants of BAFF that have decreased TACI binding. In a further object, the variants comprise at least one of the following positions: Q159, Y163, D203, K204, T205, Y206, A207, L211, R231, I233, L240, P264, R265, and D275 and more preferably, D203, Y206, I233, P264, R265, and D275. More preferably, at least one of the following substitutions comprises the BAFF variant: Q159D, Y1 63H, Y163R, D203S, D203N, D203E, D203G, K204E, K204Q, T205A, T205K, T205N, T205S, T205D, Y206A, Y206E, Y206K, Y206Q, Y206S, Y206I, A207S, L211K, L211D, R231K, I233A, I233E, I233T, I233Q, I233Y, L240K, P264N, P264D, P264A, R265A, R265K, R265L, R265H, D275A, D275V, D275K, D275R, D275H, and D275N and more preferably, D203N, Y206A, Y206E, Y206K, Y206Q, Y206S, I233E, I233Y, P264D, R265A, R265K, R265H, and D275V.

It is an object of the present invention to provide non-naturally occurring variants of BAFF that have increased TACI binding. In a further object, the variants comprise at least one of the following positions: Q159, S162, Y163, D203, A207, L211, I233, E238, L240, N242, and E266. More preferably, the variants comprise at least one of the following substitutions: Q159R, S162N, S162D, Y163K, Y163T, Y163F, Y163L, Y163I, D203K, A207T, L211V, L211E, I233V, E238Q, E238K, L240R, L240Y, L240F, N242A, 266A, E266T, E266K and E266R.

It is an object of the present invention to provide non-naturally occurring variants of BAFF that have decreased BCMA binding. In a further object, the variants comprise at least one of the following positions: Q159, Y163, D203, K204, T205, Y206, A207, L211, T228, R231, I233, L240, N242, P264, R265, E266, S271, and D275; and more preferably, D203, T205, Y206, A207, I233, L240, P264, R265, and D275. More preferably, the variants comprise at least one of the following substitutions: Q159E, Y163A, Y163H, Y163R, D203S, 203N, D203E, D203G, K204E, K204Q, P264N, P264D, P264A, R265A, R265K, R265L, R265H, E266A, E266L, E266Q, E266T, E266K, E266R, E266D, E266I, S271E, D275A, D275V, D275K, D275R, D275H, D275N, and D275E, and more preferably, D203S, D203N, D203G, T205A, T205K, T205D, Y206A, Y206E, Y206K, Y206Q, Y206S, A207S, I233A, I233E, I233T, I233Q, I233Y, L240K, P264D, P264A, R265A, R265K, R265H, D275A, D275V, D275K, D275R, D275H, D275N, D275E.

It is an object of the present invention to provide non-naturally occurring variants of BAFF that have increased BCMA binding. In a further object, the variants comprise at least one of the following positions: Q159, S162, Y163, D203, Y206, L211, T228, I233, E238, L240, N242, and D273. Preferably, the following substitutions may be used to enhance BCMA binding: Q159R, S162D, Y163D, Y163T, Y163F, Y163L, Y163I, D203K, Y206F, Y206I, L211V, T228N, I233V, E238Q, E238K, L240Y, L240F, N242A, N242Y, D273A, D273R, D273H, and D273N.

It is another object of the present invention to provide non-naturally occurring variants of BAFF that are specific for particular receptors. More specifically, it is an object to provide BAFF variants that provide decreased binding to BCMA, while binding to TACI and BAFF-R is either maintained or not significantly decreased. The preferred variants for this specificity include: T205K, D203S, D203G, T205A, A207S, I233A, I233T, L240K, P264A, and D275E. More specifically, it is an object ot provide BAFF variants that provide reduced binding to BAFF-R, increased binding to BCMA, and binding to TACI is maintained or not reduced significantly: The preferred variant for this specificity include: Y206I.

It is a further object of the present invention to provide BAFF variants having receptor antagonist or competitive inhibitor activity. More specifically, the variants comprise at least one of the following positions where binding to BAFF-R is moderately reduced, however agonistic activity is significantly reduced: D275V, D275A, P264D, and D275N.

BRIEF DESCRIPTION OF THE DRAWINGS

FIG. 1 illustrates a general mechanism by which a dominant negative BAFF protein may antagonize the action of a naturally occurring BAFF, APRIL or other TNFSF protein. Ovals represent a BAFF protein monomer and triangles represent receptor molecules. Naturally occurring BAFF proteins typically signal by organizing receptors into an active complex. Variant BAFF proteins are modified (bumps and sticks) within their receptor contact domains such that receptor binding and/or signaling is reduced. When variant BAFF trimers are incubated with naturally occurring TNFSF protein trimers, they equilibrate to form four different trimer species, three of which are inactive. At sufficient concentrations of dominant-negative variant BAFF, essentially all of the naturally occurring TNFSF protein will be sequestered into inactive heterotrimeric complexes. Through this and related mechanisms of inactivating TNFSF proteins, the dominant-negative BAFF variants will exert their therapeutic effects.

FIG. 2 depicts the experimentally determined structure of BAFF. FIGS 2a and 2b depict alternate views.

FIG. 3 shows a Multiple Sequence Alignment (MSA) of human TNFSF members (SEQ ID NOS:1 -17). FIG. 3 also shows position numberings of each individual sequence. For TNF-α(TNFA) (SEQ ID NO:1) and TNFB (LT-α) (SEQ ID NO:2), the numbering is based on current convention. For BAFF, the numbering is based on the full-length precursor sequence of the protein. For sequences in which a structure of the ligand-receptor complex has been determined experimentally, residues that lie at the ligand-receptor interface are highlighted in gray. These interfaces, highlighted in black, used to define 7 general receptor contact regions of the TNF SF ligands. A generic numbering system, beginning with position number 1, is also included above the MSA for reference.

FIG. 4 show non agonistic BAFF variants.

FIGS. 5 A-D show receptor selectivity of various BAFF variants.

FIG. 6 shows differential binding of various BAFF variants to its receptors.

FIG. 7 shows binding activity of BAFF variants to BAFF-R.

FIG. 8 shows binding activity of BAFF variants to TACI.

FIG. 9 shows binding activity of BAFF variants to BCMA.

FIG. 11 shows the Native PAGE at completion of the exchange reaction, visualized by UV light and CCD.

FIG. 12 depicts the differential biding of BAFF variants to BAFFR, TACI, and BCMA.

FIG. 12 depicts the screening of some BAFF variants for non-agonist variants.

DETAILED DESCRIPTION OF THE INVENTION

Figure 10:
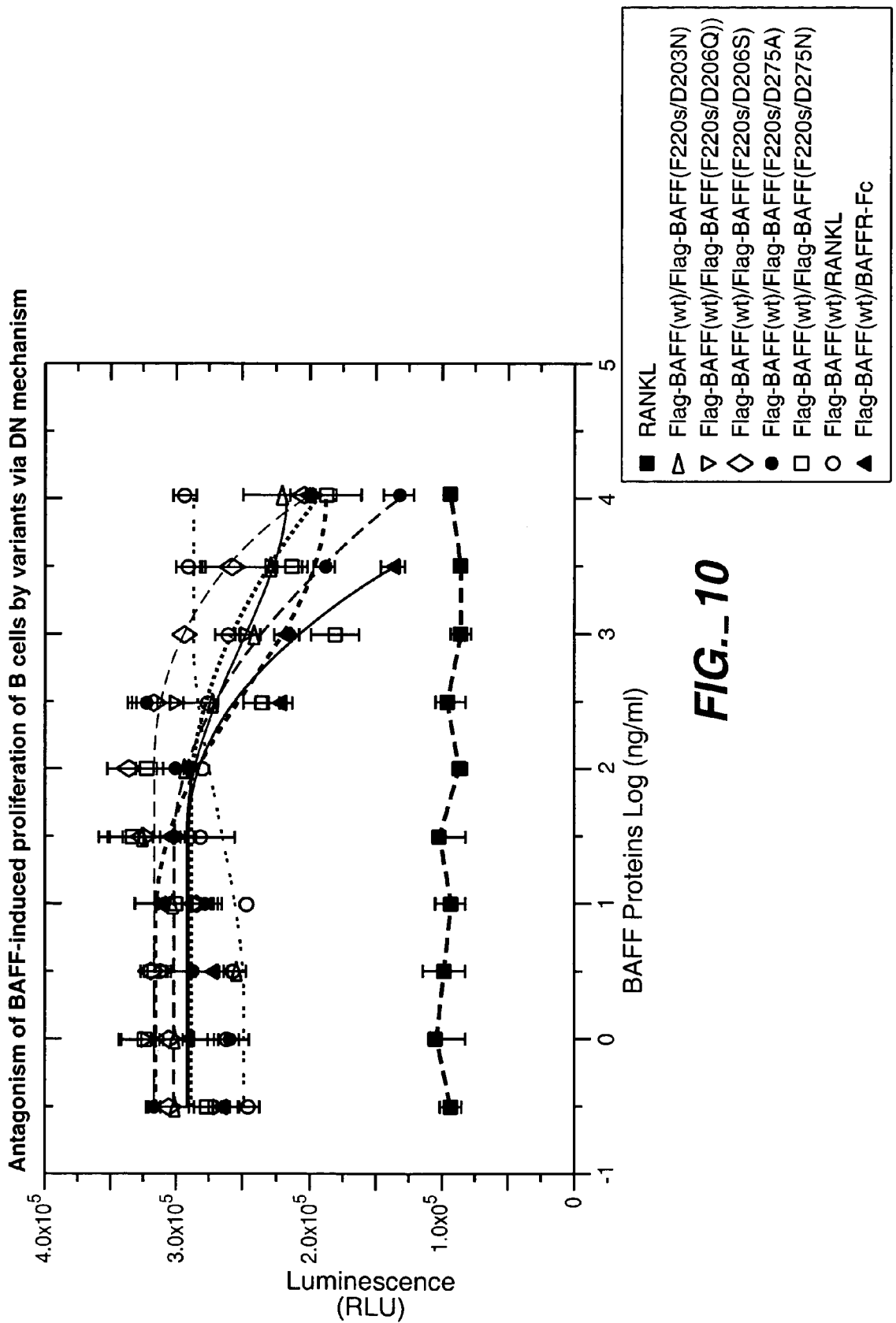
FIG. 10 shows antagonism of BAFF-induced differentiation of B cells by variants via DN.

The present invention is directed to novel proteins that modulate the biological activity of BAFF, APRIL or other TNFSF proteins.

The present invention is directed to novel proteins that exhibit a dominant negative phenotype or mechanism of action. The dominant-negative therapeutic strategy is based on the design of novel BAFF variants that have reduced receptor binding and/or activation properties as compared to naturally occurring BAFF proteins, and the ability to oligo-merize with naturally occurring BAFF or APRIL proteins (FIG. 1). In other words, BAFF variants that do not substantially activate at least one BAFF receptor (as compared to a naturally occurring BAFF protein) will exchange with at least one naturally occurring BAFF or APRIL protein and sequester it into inactive hetero-oligomers or partially inactive hetero-oligomers, inhibiting at least one biological activity. However, other mechanisms of action are also possible. Thus BAFF variants of the present invention have at least one altered BAFF biological activity, which can alteration of agaonist activity, antagonist activity, receptor binding, and specificity of receptor binding.

The BAFF variant proteins of the present invention may be designed by modifying BAFF proteins at key receptor contact points in order to modify the ability of the ligand bind to and/or to activate receptor. In preferred embodiments, the exchange and physical interaction of these oligomeric BAFF variants with naturally occurring BAFF or APRIL proteins results in the complete or partial deactivation of the naturally occurring proteins. To help accomplish this goal more effectively, the BAFF variants can also be designed to facilitate hetero-oligomerization with naturally occurring BAFF or APRIL proteins.

Accordingly, the present invention is directed to variant BAFF proteins (sometimes referred to herein as "non-naturally occurring BAFF rotein") that have at least one biological property of a naturally occurring BAFF protein that is altered or modulated. "Altered" or "modulated" in this context includes both increases and decreases in activity. "GAFF biological activity" or grammatical equivalents thereof include, but are not limited ot, modulation (either increases or decreased) of either agonist or antagonist activity, altered receptor binding (including, but not limited to, binding to BAFF receptor (BAFF-R), TACI, or BCMA), or altered receptor specificity binding (e.g. decreased binding to CBMA and no significant change in binding (e.g. binding to BCMA and no significant change in binding to BAFF-R and/or TACI; reduced binding to BAFF-R increased binding to BCMA, and no significant change in binding to TACI; etc.).

In a preferred embodiment, agonist activity of BAFF is altered. By "agonist" or "agonism" or other grammatical equivalents, as used herein (unless otherwise described) is meant an increase in activity as compared to the wild type BAFF, in particular as it relates to proliferation, maturation, or survival of B cells. Also disclosed herein are "superagonists" which also encompasses the proliferation, maturation, or survival of B cells. As an alternative example, to the general use of the term "agonist", it is known that TACI is an inhibitor of BAFF agonism.

In a preferred embodiment, the variant BAFF proteins of the invention are antagonists of naturally occurring BAFF or APRIL proteins. By "antagonists of naturally occurring BAFF or APRIL" herein is meant that the variant BAFF protein inhibits or significantly decreases the biological activity, particularly the activation of receptor signaling by a naturally occurring member of the BAFF or APRIL protein. In the context of the invention, a "significant decrease" or a "significant increase" in activity comprises at least a 10% change, with changes of 20%-50% and up to 90-100% being included.

In a preferred embodiment, the variant BAFF protein physically interacts with its naturally occurring BAFF protein such that the complex comprising the variant BAFF and wild-type BAFF is incapable of activating one or more BAFF receptors, or causes a significant decrease in activation. Preferably, the variant BAFF protein preferentially interacts with a wild-type BAFF to form mixed trimers with the wild-type proteins such that receptor binding does not occur and/or BAFF signaling through at least one receptor is not initiated, or, again, either is significantly decreased (FIG. 1).

In an alternative embodiment, the variant BAFF protein physically interacts with a naturally occurring APRIL protein. Because BAFF is known to form heterotrimers with APRIL, dominant-negative variant BAFF protein may be used to inhibit naturally occurring APRIL or BAFF proteins.

By "extracellular domain" or "ECD" as used herein is meant the segment of protein existing predominantly outside the cell. For transmembrane proteins, this segment can be tethered to the cell through a transmembrane domain or released from the cell through proteolytic digestion. Alternatively, the extracellular domain could comprise the whole protein or amino acid segments thereof when secreted from the cell. In general, BAFF is expressed as type II transmembrane proteins (extracellular C terminus). The unprocessed protein generally contains an atypical signal anchor/intracellular domain of about 10 to 80 amino acids. The extracellular region may be about 140-220 amino acids in length. Soluble forms of BAFF proteins may result from proteolytic cleavage of the signal propeptide by a furin family protease or directly by recombinant methods.

Unless otherwise disclosed, the variant BAFF proteins of the present invention are composed of the extracellular domain or functional equivalents thereof. That is, the variants of the present invention do not comprise transmembrane domains unless specifically noted. In certain embodiments of the present invention, the variant BAFF proteins would antagonize the membrane bound naturally occurring form of a BAFF or APRIL protein and in other embodiments, the variant BAFF proteins would antagonize the soluble form of a naturally occurring BAFF or APRIL protein.

By "nonconservative" modification herein is meant a modification in which the wild type residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are nonconservative modifications. In a preferred embodiment, the variant BAFF proteins of the present invention have at least one nonconservative modification of a natural, non-natural or synthetic amino acid.

Modifications of the present invention may include those to surface, boundary and core areas of a BAFF protein. See, for example, U.S. Pat. Nos. 6,188,965 and 6,269,312, hereby incorporated by reference. In another preferred embodiment, modifications may be made to surface residues.

The variant proteins may be generated, for example, by using a system previously described in U.S. Pat. Nos. 6,188, 965; 6,296,312; 6,403,312; U.S. Ser. Nos. 09/419,351, 09/782,004, 09/927,790, 09/877,695, and 09/877,695; alanine scanning (see U.S. Pat. No. 5,506,107), gene shuffling ((WO 01/25277), site saturation mutagenesis, mean field, sequence homology, or other methods known to those skilled in the art that guide the selection of point mutation sites and types.

In a preferred embodiment, sequence and/or structural alignments may be used to generate the variant BAFF proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise. There are also a wide variety of structural alignment programs known. See for example VAST from the NCBI (ncbi.nlm.nih.gov:80/StructureNAST/vast. shtml); SSAP (Orengo and Taylor, Methods Enzymol 266(617-635 (1996)) SARF2 (Alexandrov, Protein Eng 9(9):727-732. (1996)) CE (Shindyalov and Bourne, Protein Eng 11(9): 739-747. (1998)); (Orengo et al., Structure 5(8): 1093-108 (1997); Dali (Holm et al., Nucleic Acid Res. 26(1): 316-9 (1998), all of which are incorporated by reference).

The methods of the present invention can be applied to any naturally occurring BAFF protein or related system in which individual domains oligomerize to form an active complex. These domains may be modified in a number of ways to remove or reduce receptor binding and/or activation. In addition, each modified domain may be covalently coupled to at least one additional modified domain to generate dominant negative proteins with enhanced antagonistic activity.

As illustrated in FIG. 1, a variant BAFF protein is preferably modified such that interactions with at least one receptor molecule are altered. Preferably, these modifications would not substantially affect the ability of the variant domain to interact with and sequester naturally occurring BAFF or APRIL proteins. In a preferred embodiment, these modifications may be combined with additional modifications that enhance the ability of variant BAFF proteins to hetero-oligomerize with one or more naturally occurring TNFSF proteins, including but not limited to BAFF and APRIL. Most preferably, modifications that affect receptor activation and oligomerization are also combined with chemical modifications (e.g., glycosylation, phosphorylation, PEGylation, fusions, etc.) that improve pharmacokinetic properties. More preferably, the present invention is also directed to novel proteins and nucleic acids possessing BAFF antagonist activity.

The variant BAFF proteins and nucleic acids of the invention are distinguishable from naturally occurring or wild-type BAFF. By "naturally occurring", "wild-type", "native", or grammatical equivalents, herein is meant an amino acid sequence or a nucleotide sequence that is found in nature and includes allelic variations; that is, an amino acid sequence or a nucleotide sequence that usually has not been intetionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. Representative amino acid sequences of naturally occurring human TNFSF members (SEQ ID NOS:1-17) are shown in FIG. 3. It should be noted, that unless otherwise stated, all positional numbering of variant BAFF proteins and variant BAFF nucleic acids is based on these sequences. That is, as will be appreciated by those in the art, an alignment of TNFSF proteins may be done using standard programs, as is outlined below, with the identification of "equivalent" positions between proteins within the alignment. Thus, the variant BAFF proteins and nucleic acids of the invention are non-naturally occurring; that is, they do not exist in nature.

By "dominant negative" phenotype or "mechanism of action" herein is meant a protein comprising at least one BAFF domain or monomer that has reduced affinity and/or altered signaling for a desired receptor or receptors such that the protein cannot substantially interact and/or signal with the desired receptor or receptors, but retains the ability to oligomerize with other receptor interaction domains (see FIG. 1). In some embodiments, the oligomeric proteins also retain the ability to interact with and/or signal through other receptors. Depending on the composition of the oligomeric ligand complex, i.e., 2 variants:1 native or 1 variant:2 native heterotrimers, the degree to which ligand mediated receptor activation is inhibited will vary (see FIG. 1). In other words, receptor activation may be completely inhibited in a complex comprising 2variant:1native, whereas activation may be reduced in complexes comprising other ratios of variant:native. See also Menart, V., et al., (2000) *Eur J Physiol.*, 439, R113-R115; U.S. patent Pub. Nos. 2002/0039588, 2002/0040132, 2002/0037286, 2002/0037280; all of which are incorporated herein by reference. Monte carlo simulations of heterotrimer assembly, as a function of the relative concentration of variant BAFF to naturally occurring BAFF, show that, in general, greater than 99% of the naturally occurring BAFF monomers will be sequestered when a 10-fold excess of variant BAFF monomer is added.

As will be appreciated by those of skill in the art, two general approaches for creating the dominant negative variants of the present invention include: (1) modifying individual receptor interaction domains to reduce or eliminate receptor binding and/or signaling; and, (2) covalently coupling modified receptor interaction domains to enhance inhibition of receptor activation.

In a preferred embodiment, individual BAFF proteins are modified within their receptor contact domains to reduce or eliminate receptor binding and/or signaling. For example, amino acid substitutions can be generated as modifications in the receptor contact domains that reduce or eliminate receptor binding. See U.S. Pat. No. 5,506,107; U.S. Ser. Nos. 09/798,789; 09/981,289; 10/262,630; 60/374,035; U.S. Ser. No. 10/338,785 and PCT/US03/00393, filed on Jan. 6, 2003 and U.S. Ser. No. 10/338083 and PCT/US03/00394, filed Jan. 6, 2003, all of which are hereby incorporated by reference.

Preferable modifications (e.g. substitutions, insertions, deletions, etc.) that affect receptor binding or signaling may be identified using a variety of techniques, including structural alignment methods, sequence alignment methods, etc., as described above. In many cases, the amino acids in the BAFF ligand that interact with the receptor can be identified directly from a three-dimensional structure or model of the BAFF ligand-receptor complex or computer modeling.

As is known in the art, there are a number of sequence alignment methodologies that may be used. For example, sequence homology based alignment methods may be used to create sequence alignments of TNFSF members (Altschul et al., J. Mol. Biol. 215(3): 403-410 (1990); Altschul et al., Nucleic Acids Res. 25:3389-3402 (1997), both incorporated by reference). These sequence alignments are then examined to determine the observed sequence variations. These sequence variations may be tabulated to define a set of variant BAFF proteins.

Sequence based alignments may be used in a variety of ways. For example, a number of related proteins may be aligned, as is known in the art, and the "variable" and "conserved" residues defined; that is, the residues that vary or remain identical between the family members can be defined. The extent of variability at positions within the alignment can also be used to identify positions in the protein where mutation is permissive regarding preservation of structural features of the protein. These results may be used to guide the design of variant protein libraries whose properties can be probed experimentally. For example, the positions of high variability between family members (i.e. low conservation) may be randomized, either using all or a subset of amino acids. Alternatively, the sequence variations may be tabulated and appropriate substitutions defined from them. Alternatively, the allowed sequence variations may be used to define the amino acids considered at each position during a computational modeling and/or screening process. Another variation is to bias the score for amino acids that occur in the sequence alignment, thereby increasing the likelihood that they are found during computational screening but still allowing consideration of other amino acids. This bias would result in a focused library of variant BAFF proteins but would not eliminate from consideration amino acids not found in the alignment.

In a preferred embodiment, as highlighted in FIG. 3, the amino acid sequences of TNFSF proteins may be aligned into a multiple sequence alignment (MSA). The alignment shown in FIG. 3 was derived originally from the Pfam database, and then further manipulated according to structural alignment (using CE) of the crystal structures of TNFA, TNFB and BAFF. The MSA may also be used to extend the known structural information for additional recognized TNFSF members and other structural homologues and families. Due to the high extent of structural homology between BAFF and other TNFSF members, the MSA may be used as a reliable predictor of the effects of modifications at various positions within the alignment. For this, the TNFA sequence and numbering shown in FIG. 3 can be used as an MSA reference point for any other TNFSF protein sequence, such as BAFF. As used herein, referral to "BAFF protein positions corresponding to TNFA amino acid X", represents referral to a collection of equivalent positions in BAFF and structural homologues and families. For example, BAFF protein positions corresponding to TNFA amino acid L75 corresponds to BAFF: A207. It also corresponds to APRIL:T177.

For example, analysis of a structure of the complex of TNFB with the p55 (R1) receptor indicates that the amino acid Y108 in TNFB directly contacts the receptor. The analogous residue Y216 from TRAIL also directly contacts the DR5 receptor. The MSA thus predicts that the analogous residue I97 from TNFA also contacts a receptor. Consistent with this prediction, mutation of TNFA-I97 to R or T results in a significant loss of receptor-binding affinity and biological signaling activity. The analysis for this contact position can be extended to BAFF, predicting that BAFF:I233 is important for receptor interactions. This kind of analysis can be performed for all receptor contact regions of the ligands.

FIG. 3 highlights 7 canonical receptor contact regions based on analysis of known structures and mutational data. In preferred embodiments of the invention, each of the 7 regions highlighted in FIG. 3 as a receptor-contact region is used to define modification sites for the creation of variants of BAFF. In additional preferred embodiments, such modifications alter receptor affinity and/or signaling capacity. In additional preferred embodiments, these modifications also preserve the ability of each protein to oligomerize with naturally occurring BAFF or APRIL proteins.

Using the alignment system depicted in FIG. 3 or other alignment programs discussed above, one can use as a reference point, the numbering system of any alignment program and may correlate the relevant positions of the TNFA protein with equivalent positions in BAFF or structural homologues and families.

For purposes of the present invention, the areas of BAFF proteins to be modified are selected from the group consisting of the Large Domain, Small Domain, the DE loop, and the trimer interface. The Large Domain and the Small Domain are two separate receptor contact domains, each made up of several non-contiguous linear segments of the protein. Hence, substitution of amino acids at these positions is expected to alter the ability of BAFF proteins to interact and/or signal with one or more BAFF receptors. The trimer interface mediates interactions between individual BAFF protein monomers and between BAFF and APRIL monomers. Trimerization positions can be identified either directly from the crystal structure of the BAFF protein, or by analogy to another TNFSF protein. In a preferred embodiment, positions from one BAFF protein monomer containing atoms that are within 5 angstroms distance from a neighboring monomer are designated as trimer interface positions. The DE loop has been demonstrated through structural analysis to mediate interactions between individual BAFF trimers. Hence, substitution of amino acids at DE loop positions is expected to alter the ability of BAFF proteins to form higher order structures. Modifications may be made solely in one of these areas or in any combination of these and other areas.

In a preferred embodiment, inspection of the MSA and the three-dimensional structure of BAFF indicate that the Large Domain preferred positions to be modified in BAFF include but are not limited to TNFA corresponding positions 28-34, 63-69, 112-115, and 137-147 that is, positions 150, 169-172, 200-204, 239-242, and 271-275. For the Small Domain, the preferred positions to be modified include but are not limited to TNFA corresponding positions 72-79 and 95-98, that is positions 205-211 and 231-233. For the DE Loop, the preferred positions to be modified include but are not limited to TNFA corresponding positions 84-89, that is, positions 216-225. Analysis of the three-dimensional structure of BAFF reveals that the preferred trimer interface positions to be modified include but are not limited to TNFA corresponding positions 11, 13, 15, 34, 36, 53-55, 57, 59, 61, 63, 72, 73, 75, 77, 119, 87, 91-99, 102-104, 109, 112-125, 147-149, 151, and 155-157, that is positions 143, 144, 146, 148, 172, 174, 192, 194, 196, 198, 200, 206, 207, 228, 230, 237, 240-250, 271, 273, 275, 276, 278, 282, 284 and 285. Especially preferred trimer interface positions to be modified are TNFA corresponding positions 57, 34, and 91, that is positions 172, 174, 192, 192, 194, 250 and 285. For example, amino acids interacting at a trimer interface may be replaced simultaneously by similarly charged amino acids to generate electrostatic repulsion at the variant monomer-monomer interfaces while not perturbing the stability of variant-native interfaces.

In a preferred embodiment, amino acid substitutions, deletions, or insertions that influence the kinetics of exchange between variant and wild-type monomers are made either individually or in combination. These substitutions can also be combined with additional substitutions that affect receptor interaction or other properties. Substitutions that have an effect on exchange properties may include substitutions at positions T205, Y206, F220, E223, V227, T228, I233, L240, D273 and D275, among others.

In a preferred embodiment, the choice of modification site and type is made by referring to other sequences in the alignment. Thus, in a preferred embodiment, the original amino acid X from sequence A is mutated to amino acid Y from sequence B, such that Y is a nonconservative substitution relative to amino acid X. For example, the amino acid Y87 from TNFA aligns with the non-conservative R189 from APRIL. Indeed, as previous studies have shown, the Y87R substitution in TNFA leads to a significant decrease in receptor binding and signaling by TNFA. In additional embodiments, more conservative mutations can also be utilized. In additional embodiments, the wild-type residue is mutated to alanine.

In a preferred embodiment, useful modifications at receptor contact and/or trimerization interfaces are selected using protein design or modeling algorithms such as PROTEIN DESIGN AUTOMATION® (PDA®) technology (see, U.S. Pat. No. 6,188,965; 6,269,312; 6,403,312; U.S. Ser. Nos. 09/714,357; 09/812,034; 09/827,960; 09/837,886; 09/782,004 and 10/218,102, all hereby incorporated by reference). As is known in the art, algorithms in this class generally use atomic-level or amino acid level scoring functions to evaluate the compatibility of amino acid sequences with the overall tertiary and quaternary structure of a protein. Thus, algorithms of this class can be used to select receptor-binding disruptions that do not substantially perturb the ability of variant BAFF proteins to properly fold and oligomerize with themselves or their naturally occurring targets. These technologies typically use high-resolution structural information of the target protein as input. In a preferred embodiment, an experimentally determined strucure of the BAFF protein is used as input. For BAFF, high-resolution structures have been determined. In additional preferred embodiments, experimentally determined crystal structures of BAFF/receptor complexes may be used as structural scaffolds to guide the design of variant BAFF ligands that possess reduced receptor binding and/or signaling and/or dominant-negative activity. In additional embodiments, comparative analysis of various BAFF/receptor complexes may guide the design of variants that have selective binding and/or signaling through BAFF receptors.

Simulations and visual inspection of multiple crystal structures were combined to define a set of mutations that might disrupt the DE loop interface formed between BAFF trimers (the "DE loop handshake"). The "DE loop handshake" exists between different BAFF trimers, thus potentiating the formation of higher order structures, including specific oligomers and non-specific aggregates. Substitution of amino acids at these positions is expected to modify the ability of BAFF to form these higher order structures. This analysis led to the design of the following exemplary substitutions F220S, E223K, and F220S/E223Q, which were designed to disrupt the DE loop handshake and prevent aggregate formation.

In alternative embodiments, protein design algorithms may be used to generate mutations in individual receptor interaction domains that create steric repulsion between the receptor interaction domain and the receptor. Other mutations that may be generated include, but are not limited to, mutations that create electrostatic repulsion, and mutations that create unfavorable desolvation of amino acids.

Similarly, molecular dynamics calculations may be used to computationally screen sequences by individually calculating mutant sequence scores and compiling a list.

In a preferred embodiment, residue pair potentials may be used to score sequences (Miyazawa et al, Macromolecules 183): 534-552 (1985), expressly incorporated by reference) during computational screening.

In a preferred embodiment, substitutions, insertions, deletions or other modifications at multiple receptor interaction and/or trimerization domains may be combined. Such combinations are frequently advantageous in that they have additive or synergistic effects on activity. Examples include, but are not limited to, simultaneous substitution of amino acids at the large and small domains (BAFF positions 202 and 233), large domain and DE loop (BAFFpositions 242 and 220), large domain and trimerization domain (e.g. BAFF positions 273 and 194), or multiple substitutions within a single domain. Additional examples include any and all combinations of substitutions.

In preferred embodiments, the defined receptor contact regions constitute sites for insertion, deletion, or substitution of amino acid residues, or sites for the introduction of chemical modification sites. In a preferred embodiment, deletions or insertions are made in accordance with the MSA.

In additional embodiments, the variants described above can be combined with other modifications to the BAFF protein. These include, but are not limited to, additional amino acid substitutions, insertions, or deletions, and/or chemical (e.g. PEGylation) or posttranslational modifications such as phosphorylation or glycosylation (see WO 99/45026; WO 01/49830; WO 01/49830; WO 02/02597; WO 01/58493; WO 01/51510, U.S. Pat. Nos. 4,002,531; 5,183,550; 5,089,261; 6,153,265; 5,264,209; 5,383,657; 5,766,897; 5,986,068; 4,280,953; 5,089,261; 5,990,237; 6,461,802; 6,495,659; 6,448,369; 6,437,025; 5,900,461; 6,413,507; 5,446,090; 5,672,662; 5,919,455; 6,113,906; 5,985,236; 6,214,966; 6,258,351; 5,932,462; EP 0786 257; EP 0 902 085; EP 1 064 951; EP 0 544 826; EP 0 424 405; EP 0 400 472; EP 0 311 589; Veronese, F.M. (2001) Biomaterials, 22: 405-471; all of which are incorporated herein by reference).

In a preferred embodiment, additional amino acid substitutions are made to optimize hetero-oligomer interactions between variant BAFF and its endogenous counterpart and/or to destabilize the oligomeric state of the variant alone. For example, an L57F mutation in TNFA has been designed in order to promote the formation of variant:native heterotrimers while disfavoring the formation of variant homotrimers. Such modifications are useful for promoting the exchange of variant monomers with native monomers in order to promote a dominant-negative mechanism of action. Because BAFF contains an F at this position naturallyl, the mutation F194L might be expected to affect trimerization with BAFF, APRIL, or both.

As will be understood by those in the art, variant BAFF proteins which have altered signaling capacity can be discovered by a large variety of methods, including, but not limited to, directed evolution (e.g. error prone PCR, DNA shuffling, etc.), single-site saturation mutagenesis, and alanine-scanning mutagenesis. Furthermore, it is possible that use of these or other methods will allow the discovery of substitutions, insertions, or deletions—which alter receptor binding and/or signaling activity—that lie outside of the 7 canonical contact regions described herein.

In another embodiment, coiled-coil motifs are used to assist dimer assembly (see Dahiyat et al., Protein Science 6:1333-7 (1997) and U.S. Ser. No. 09/502,984; both of which are incorporated herein by reference in their entirety). Coiled coil motifs comprise, but is not limited to one of the following sequences: RMEKLEQKVKELLRKNERLEEEVERLKQLVGER(SEO ID NO:18), based on the structure of GCN4; AALESEVSALESEVASLESEVAAL(SEO ID NO: 19), and LAAVKSKLSAVKSKLASVKSKLAA(SEQ ID NO:20), coiled-coil leucine zipper regions defined previously (see Martin et al., EMBO J. 13(22): 5303-5309 (1994), incorporated by reference). Other coiled coil sequences from e.g. leucine zipper containing proteins are known in the art and are used in this invention. See, for example, Myszka et al., Biochem. 33:2362-2373 (1994), hereby incorporated by reference).

As will be appreciated by those in the art, additional BAFF proteins may be identified and added to the MSA highlighted in FIG. 3. The source of the sequences may vary widely, and include taking sequences from one or more of the known databases, including, but not limited to, GenBank (.ncbi.nlm.nih.gov/).

In addition, sequences from these databases may be subjected to contiguous analysis or gene prediction; see Wheeler, et al., Nucleic Acids Res 28(1):10-14. (2000) and Burge and Karlin, J Mol Biol 268(1):78-94. (1997).

As used herein variant BAFF or BAFF proteins include BAFF monomers or dimers.

The BAFF proteins may be from any number of organisms, with BAFF proteins from mammals being particularly preferred. Suitable mammals include, but are not limited to, rodents (rats, mice, hamsters, guinea pigs, etc.), primates, farm animals (including sheep, goats, pigs, cows, horses, etc); and in the most preferred embodiment, from humans. As will be appreciated by those in the art, BAFF proteins based on BAFF proteins from mammals other than humans may find use in animal models of human disease.

By "heterotrimers (or mixed trimers)" herein is meant that monomers of native and variant BAFF proteins interact to form trimeric BAFF. Heterotrimers or mixed trimers may comprise 1 variant BAFF protein: 2 native BAFF proteins, 2 variant BAFF proteins:1 native BAFF protein. In some embodiments, heterotrimers or mixed trimers may be formed comprising only variant BAFF proteins. In alternative embodiments, for example, heterotrimers or mixed trimers may comprise 1 variant BAFF protein, 1 native BAFF protein, and 1 APRIL protein; or 2 BAFF proteins: 1 native APRIL protein; and any other possible combinations thereof.

In a preferred embodiment, the variant BAFF antagonist proteins of the invention are highly specific antagonists for the corresponding wild-type BAFF protein. However, in alternative embodiments, the variant BAFF antagonistic proteins of the invention are highly specific for more than one wild-type TNFSF protein. For example, variant BAFF proteins may be specific antagonist of wild-type APRIL only, wild-type APRIL and BAFF, or wild-type BAFF only. Additional characteristics of the variant BAFF antagonist proteins include improved stability, pharmacokinetics, and high affinity for native BAFF. Variants with higher affinity toward native BAFF may be generated from variants exhibiting BAFF antagonism as outlined above.

In a preferred embodiment, variant BAFF proteins exhibit decreased biological activity as compared to native BAFF, including but not limited to, decreased binding to the one or more receptors, decreased activation or otherwise undesired activities that can lead to deleterious side effects. Variant BAFF proteins that exhibit less than 50% biological activity as compared to native are preferred. More preferred are variant BAFF proteins that exhibit less than 25%, even more preferred are variant proteins that exhibit less than 15%, and most preferred are variant BAFF proteins that exhibit less than 10% of a biological activity of a naturally occurring BAFF. Suitable assays include, but are not limited to, BAFF receptor binding assays; transcription assays (using reporter constructs; see Stavridi, supra); size exclusion chromatography assays and radiolabeling/immuno-precipitation; see Corcoran et al., supra); and stability assays (including the use of circular dichroism (CD) assays and equilibrium studies; see Mateu, supra); all of which are expressly incorporated by reference.

In one embodiment, at least one property critical for binding affinity of the variant BAFF proteins is altered when compared to the same property of native BAFF and in particular, variant BAFF proteins with altered receptor affinity for at least one receptor are preferred. Also preferred are variant BAFF with altered affinity toward oligomerization to native BAFF and/or APRIL.

Thus, the invention provides variant BAFF proteins with altered binding affinities such that the variant BAFF proteins will preferentially oligomerize with wild-type BAFF, but do not substantially agonize one or more BAFF receptors. "Preferentially" in this case means that given equal amounts of variant BAFF monomers and wild-type BAFF monomers, at least 10% and more preferably at least 25% of the resulting trimers are mixed trimers of variant and wild-type BAFF, with at least about 50% being preferred, and at least about 80-90% being particularly preferred. In other words, it is preferable that the variant BAFF proteins of the invention have greater affinity for wild-type BAFF protein as compared to other wild-type BAFF proteins. By "do not substantially interact with TNF receptors" herein is meant that the variant BAFF proteins will not be able to associate with BAFF receptors to substantially activate the receptors and/or initiate the BAFF signaling pathway(s). In a preferred embodiment, at least a 10% decrease in receptor activation is seen, with greater than 20%, 50%, 76%, 80-90% being preferred. By "agonize BAFF receptors" herein is meant that a variant BAFF protein enhances the survival co-stimulatory activation of survival, maturation, receptor, etc. signaling.

Non-naturally occurring variants of BAFF that have modulated receptor binding is one aspect of the present invention.

Variants with a decrease in BAFF-R binding include but are not limited to at least one of the following positions: Q159, Y163, D203, T205, Y206, A207, L211, R231, I233, P264, R265, and D275, more preferably D203, T205, Y206, I233, R265, and D275. More particularly, the variants comprise at least one of the following substitutions: Y206A, Y206E, Y206K, Y206I, I233E, I233Y, R265K, Y206S, R265A, R265H, T205D, D275R, Y206Q, D203N, D275K, I233Q, D275H, T205N, D275V, P264N, D275A, P264D, P264A, R265L, D275N, D203E, L211K, L211D, D203S, I233T, Q159D, R231K, Y163R, T205S, A207S, T205A, and I233A, and more preferably, at least one of the following substitutions: D203N, T205D, Y206A, Y206E, Y206K, Y206Q, Y206S, Y206I, I233E, I233Q, I233Y, R265A, R265K, R265H, D275K, D275R, and D275H.

Variants of wt BAFF that have increased BAFF-R binding include but are not limited to at least one of the following positions: Q159, S162, Y163, D293, L211, I 233, E238, L240, N242, E266, and Q269. More preferably, at least one of the following substitutions comprises the non-naturally occurring BAFF: Q159R, S162N, S162D, Y163T, Y163F, Y163L, Y163I, D203K, L211V, L211E, I233L, I233V, E238Q, E238K, L240N, L240R, L240Y, L240F, N242A, 266A, E266L, E266T, E266I, Q269K, and Q269E.

Variants of BAFF that have decreased TACI binding include but are not limited to at least one of the following positions: Q159, Y163, D203, K204, T205, Y206, A207, L211, R231, I233, L240, P264, R265, and D275 and more preferably, D203, Y206, I233, P264, R265, and D275. More preferably, at least one of the following substitutions comprises the BAFF variant: Q159D, Y163H, Y163R, D203S, D203N, D203E, D203G, K204E, K204Q, T205A, T205K, T205N, T205S, T205D, Y206A, Y206E, Y206K, Y206Q, Y206S, Y206I, A207S, L211K, L211D, R231K, I233A, I233E, I233T, I233Q, I233Y, L240K, P264N, P264D, P264A, R265A, R265K, R265L, R265H, D275A, D275V, D275K, D275R, D275H, and D275N and more preferably, D203N, Y206A, Y206E, Y206K, Y206Q, Y206S, I233E, I233Y, P264D, R265A, R265K, R265H, and D275V.

IVariants of BAFF that have increased TACI binding include but are not limited to at least one of the following positions: Q159, S162, Y163, D203, A207, L211, I233, E238, L240, N242, and E266. More preferably, the variants comprise at least one of the following substitutions: Q159R, S162N, S162D, Y163K, Y163T, Y163F, Y163L, Y163I, D203K, A207T, L211V, L211E, I233V, E238Q, E238K, L240R, L240Y, L240F, N242A, 266A, E266T, E266K and E266R.

Variants of BAFF that have decreased BCMA binding, include but are not limited to least one of the following positions: Q159, Y163, D203, K204, T205, Y206, A207, L211, T228, R231, I233, L240, N242, P264, R265, E266, S271, and D275; and more preferably, D203, T205, Y206, A207, I233, L240, P264, R265, and D275. More preferably, the variants comprise at least one of the following substitutions: Q159E, Y163A, Y163H, Y163R, D203S, 203N, D203E, D203G, K204E, K204Q, T205A, T205K, T205S, T205D, Y206A, Y206E, Y206K, Y206Q, Y206S, A207S, L211D, L211E, T228V, R231K, I233A, I233E, I233T, I233Q, I233Y, L240A, L240K, L240N, L240R, N242S, P264N, P264D, P264A, R265A, R265K, R265L, R265H, E266A, E266L, E266Q, E266T, E266K, E266R, E266D, E266I, S271E, D275A, D275V, D275K, D275R, D275H, D275N, and D275E, and more preferably, D203S, D203N, D203G, T205A, T205K, T205D, Y206A, Y206E, Y206K, Y206Q, Y206S, A207S, I233A, I233E, I233T, I233Q, I233Y, L240K, P264D, P264A, R265A, R265K, R265H, D275A, D275V, D275K, D275R, D275H, D275N, and D275E.

Variants of BAFF that have increased BCMA binding, include but are not limited to at least one of the following positions: Q159, S162, Y163, D203, Y206, L211, T228, I233, E238, L240, N242, and D273. Preferably, the following substitutions may be used to enhance BCMA binding: Q159R, S162D, Y163D, Y163T, Y163F, Y163L, Y163I, D203K, Y206F, Y206I, L211V, T228N, I233V, E238Q, E238K, L240Y, L240F, N242A, N242Y, D273A, D273R, D273H, and D273N.

In addition to modulation of receptor activity, the present invention has identified variants that achieve receptor specificity. For example, BAFF variants that provide decreased binding to BCMA, while binding to TACI and BAFF-R is either maintained or not significantly decreased. The preferred variants for this specificity include but are not limited to: T205K, D203S, D203G, T205A, A207S, I233A, I233T, L240K, P264A, and D275E.

Further, BAFF variants that provide reduced binding to BAFF-R, increased binding to BCMA, and binding to TACI is maintained or not reduced significantly have been identified. The preferred variant for this specificity includes Y206I.

Variant BAFF proteins may be experimentally tested and validated using in vivo and in vitro assays. Suitable assays include, but are not limited to, activity assays and binding assays. Screens that may be utilized in identifying BAFF variants that are antagonists of BAFF proteins include, but are not limited to, NF-kB nuclear translocation (Wei et al., Endocrinology 142, 1290-1295, (2001)) or c-Jun (Srivastava et al., JBC 276, 8836-8840 (2001)) transcription factor activation assays, B-cell proliferation assays and IgE secretion assays.

In a preferred embodiment, binding affinities for the following interactions are determined and compared: 1) variant BAFF oligomer formation, 2) wild-type BAFF oligomer formation, 3) variant BAFF binding to cognate receptors (e.g., BAFF-R, BCMA and TACI), 4) wild-type BAFF binding to cognate receptors, 5) variant BAFF binding to decoy receptors, and 6) wild-type BAFF binding to decoy receptors. Similar tests can be utilized to determine whether BAFF variants are capable of forming mixed trimers with wild-type or variant APRIL proteins. Suitable assays include, but are not limited to, quantitative comparisons comparing kinetic and equilibrium binding constants. The kinetic association rate (Kon) and dissociation rate (Koff), and the equilibrium binding constants (Kd) may be determined using surface plasmon resonance on a BlAcore instrument following the standard procedure in the literature [Pearce et al., Biochemistry 38:81-89 (1999)]. Several alternative methods can also be used to determine binding affinity and kinetics, including but not limited to proximity assays such as AlphaScreen™ (Packard BioScience®) or microcalorimetry (Isothermal Titration Calorimetry, Differential Scanning Calorimetry).

BAFF variants may also be tested to determine whether they are capable of forming mixed oligomers including but not limited to mixed trimers. In a preferred embodiment, this is accomplished by labeling native BAFF and variant BAFF with distinguishable tags, combining native and variant BAFF, and screening for oligomers that contain both tag types. For example, FLAG-tagged native BAFF and myc-tagged variant BAFF can be combined, and sandwich ELISAs can be performed to identify trimers that contain both FLAG and myc-tag. Another alternative is to run native gels with FLAG-tagged native BAFF and His-tagged variant BAFF to separate the mixture into separate species and detect using coomassie staining or Western blots using both anti-FLAG and anti-His tag antibodies. This method relies on the fact that FLAG and His tags significantly perturb protein migration in native gels. As will be appreciated by those in the art, many alternate protocols could also be used to measure the formation of mixed trimers. Similar tests can be utilized to determine whether BAFF variants are capable of forming mixed trimers with wild-type or variant APRIL proteins.

In a preferred embodiment, using SEC, untagged, N-terminally tagged BAFF species (Flag-and His-tagged) may be analyzed and the state of oligomerization determined. Untagged and Flag-BAFF form trimers, whereas His-BAFF forms 60-mers in the range of pH of about 6.5-8. In a preferred embodiment, these higher order oligomers become trimeric upon removal of the His-tag by protease cleavage. Under physiological conditions BAFF species are trimeric, whereas an N-terminal His-tag promotes formation of higher order oligomers.

In a preferred embodiment, variant BAFF proteins have reduced binding and/or signaling through all BAFF receptors. Such variant BAFF proteins preferably retain the ability to exchange and physically interact with wild-type BAFF or APRIL proteins, such that they are inactivated upon complex formation.

In a preferred embodiment, variant BAFF proteins may only form heterotrimeric complexes with other BAFF proteins. In an alternative embodiment, variant BAFF proteins may only form heterotrimeric complexes with APRIL proteins. As an alternative embodiment, variant BAFF proteins may form heterotrimeric complexes with BAFF and APRIL proteins. As a further embodiment, variant BAFF proteins may form heterotrimeric complexes with at least one TNFSF protein other than BAFF and APRIL.

In a preferred embodiment, variant BAFF proteins of the invention have reduced binding and/or signaling through one or more BAFF receptors while retaining binding and signaling through other BAFF receptors. For example, because TACI has recently been implicated as an inhibitory BAFF receptor, preferred BAFF variants retain the ability to signal through TACI. In a preferred embodiment, BAFF variants have increased binding and/or signaling through TACI. In alternative preferred embodiments, BAFF variants have increased signaling through TACI but decreased signaling through BAFF-R and BCMA.

Variant BAFF proteins with altered receptor signaling properties can act either as homotrimers, heterotrimers, or both. For example, a variant BAFF homotrimer with maintained or increased TACI signaling and decreased BAFF-R and/or BCMA signaling may exert its biological activities as a homotrimer that specifically stimulates the inhibitory BAFF receptor activity of TACI. Alternatively, a variant BAFF protein homotrimer with maintained or increased TACI signaling and decreased BAFF-R and/or BCMA signaling may exert its biological activities by exchanging and physically interacting with naturally occurring BAFF and/or APRIL proteins to create complexes that stimulate TACI but are incapable of stimulating BAFF-R and/or BCMA.

In a preferred embodiment, variant BAFF proteins can interact with—but not induce signaling through—one or more BAFF receptors. These variant BAFF proteins can be used as competitive inhibitors or receptor antagonists, either alone, or as complexes with naturally occurring BAFF or APRIL proteins.

BAFF variants having receptor antagonist or competitive inhibitor activity include but are not limited to D275V, D275A, P264D, and D275N. More specifically, this activity is achieved at positions where binding to BAFF-R is moderately reduced, however agonistic activity is significantly reduced:

In an alternative preferred embodiment, variant BAFF proteins have increased signaling through one or more BAFF receptors and increased or maintained signaling through other BAFF receptors. Such variants may find use in research or therapeutic strategies in which stimulation of BAFF signaling pathways is desirable. Examples include, but are not limited to B cell proliferation for research purposes, or B cell proliferation for treatment of immune deficiency syndromes or oncological diseases.

In a preferred embodiment, variant BAFF proteins have increased or maintained signaling through BAFF-R and BCMA and reduced signaling through TACI, such that stimulation of the BAFF pathway is maximized.

Any combinations of the variants disclosed above may be employed to achieve a particular therapeutic result. For example, some combinations include, but are not limited to, at least one variant that increases TACI binding and decreases binding to BAFF-R; increases binding to TACI and decreases binding to BCMA; superagonist activity with TACI (TACI being an inhibitor of BAFF agonism) and minimal binding change for BAFF-R; decreases binding to BAFF-R and decreases binding to BCMA; decreases binding to TACI and increases bidning to BAFFR—optionally an increase in binding to BCMA may also be added. For example, variant BAFF proteins that have reduced signaling thorugh BAFF-R and BCMA while maintaining or increasing signaling through TACI are expected to be potent antagonists of BAFF-mediated biology.

As outlined above, the invention provides variant BAFF nucleic acids encoding variant BAFF polypeptides. The variant BAFF polypeptide preferably has at least one altered property as compared to the same property of the corresponding naturally occurring BAFF polypeptide. The property of the variant BAFF polypeptide is the result of the present invention.

The term "altered property" or grammatical equivalents thereof in the context of a polypeptide, as used herein, further refers to any characteristic or attribute of a polypeptide that can be selected or detected and compared to the corresponding property of a naturally occurring protein. As noted above, preferred altered properties are those of BAFF biological activity, as defined herein, including receptor binding (both agonist and antagonist activities), and receptor specificity. In addition, other types of properties include, but are not limited to, proliferation activity (again, a biological property); oxidative stability, substrate specificity, substrate binding or catalytic activity, thermal stability, cytoxic activity, alkaline stability, pH activity profile, resistance to proteolytic degradation, kinetic association (Kon) and dissociation (Koff) rate, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and the ability to treat disease.

Unless otherwise specified, a substantial change in any of the above-listed properties, when comparing the property of a variant BAFF polypeptide to the property of a naturally occurring BAFF protein is preferably at least a 20%, more preferably, 50%, more preferably at least a 2-fold increase or decrease. A change in proliferation activity is evidenced by at least a 75% or greater decrease in cell proliferation initiated by a variant BAFF protein as compared to wild-type protein.

A change in binding affinity is evidenced by at least a 5% or greater increase or decrease in binding affinity of BAFF variants to wild-type BAFF receptor proteins or to wild-type BAFF.

In a preferred embodiment, the antigenic profile in the host animal of the variant BAFF protein is similar, and preferably identical, to the antigenic profile of the host BAFF; that is, the variant BAFF protein does not significantly stimulate the host organism (e.g. the patient) to an immune response; that is, any immune response is not clinically relevant and there is no allergic response or neutralization of the protein by an antibody. That is, in a preferred embodiment, the variant BAFF protein does not contain additional or different epitopes from the wild type or naturally occurring BAFF. By "epitope" or "determinant" herein is meant a portion of a protein that will generate and/or bind an antibody. Thus, in most instances, no significant amounts of antibodies are generated to a variant BAFF protein. In general, this is accomplished by not significantly altering surface residues, as outlined below nor by adding any amino acid residues on the surface which can become glycosylated, as novel glycosylation can result in an immune response, nor by the introduction of new MHC binding epitopes.

The variant BAFF proteins of the present invention may be shorter or longer than the amino acid sequences (SEQ ID NOS:1-17) shown in FIG. 3. As used in this invention, "wild-type BAFF" is a native mammalian protein (preferably human). BAFF may be polymorphic. Thus, in a preferred embodiment, included within the definition of variant BAFF proteins are portions or fragments of the sequences depicted herein. Fragments of variant BAFF proteins are considered variant BAFF proteins if a) they share at least one antigenic epitope; b) have at least the indicated homology; c) and preferably have variant BAFF biological activity as defined herein.

In a preferred embodiment, as is more fully outlined below, the variant BAFF proteins include further amino acid variations, as compared to a wild-type BAFF, than those outlined herein. Examples include, but are not limited to, amino acid substitutions introduced to enable soluble expression in *E. coli,* amino acid substitutions introduced to optimize solution behavior, and amino acid substitutions introduced to modulate immunogenicity. In addition, as outlined herein, any of the variations depicted herein may be combined in any way to form additional novel variant BAFF proteins.

In addition, variant BAFF proteins may be made that are longer than those depicted in the figures, for example, by the addition of epitope or purification tags, as outlined herein, the addition of other fusion sequences, etc. For example, the variant BAFF proteins of the invention may be fused to other therapeutic proteins or to other proteins such as Fc or serum albumin for pharmacokinetic purposes. See for example U.S. Pat. No. 5,766,883 and 5,876,969, both of which are expressly incorporated by reference.

Variant BAFF proteins may also be identified as being encoded by variant BAFF nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, a variant BAFF nucleic acid encodes a variant BAFF protein. As will be appreciated by those in the art, due to the degeneracy of the genetic code, an extremely large number of nucleic acids may be made, all of which encode the variant BAFF proteins of the present invention. Thus, having identified a particular amino acid sequence, those skilled in the art could make any number of different nucleic acids, by simply modifying the sequence of one or more codons in a way that does not change the amino acid sequence of the variant BAFF.

The variant BAFF proteins and nucleic acids of the present invention are recombinant. As used herein, "nucleic acid" may refer to either DNA or RNA, or molecules that contain both deoxy-and ribonucleotides. The nucleic acids include genomic DNA, cDNA and oligonucleotides including sense and anti-sense nucleic acids. Such nucleic acids may also contain modifications in the ribose-phosphate backbone to increase stability and half-life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated variant BAFF nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild-type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a variant BAFF protein from one organism in a different organism or host cell. Alternatively, the protein may be made at a significantly higher concentration than is normally seen, through the use of an inducible promoter or high expression promoter, such that the protein is made at increased concentration levels. Furthermore, all of the variant BAFF proteins outlined herein are in a form not normally found in nature, as they contain amino acid substitutions, insertions and deletions, with substitutions being preferred.

Also included within the definition of variant BAFF proteins of the present invention are amino acid sequence variants of the variant BAFF sequences outlined herein and shown in the Figures. That is, the variant BAFF proteins may contain additional variable positions as compared to human BAFF. These variants fall into one or more of three classes: substitutional, insertional or deletional variants. These variants ordinarily are prepared by site-specific mutagenesis of nucleotides in the DNA encoding a variant BAFF protein, using cassette or PCR mutagenesis or other techniques well known in the art, to produce DNA encoding the variant, and thereafter expressing the DNA in recombinant cell culture as outlined above. However, variant BAFF protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the variant BAFF protein amino acid sequence. The variants typically exhibit the same qualitative biological activity as the naturally occurring analogue; although variants can also be selected which have modified characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed variant BAFF proteins screened for the optimal combination of desired activity. Techniques for making substitution mutations at predetermined sites in DNA having a known sequence are well known, for example, M13 primer mutagenesis and PCR mutagenesis. Screening of the mutants is done using assays of variant BAFF protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final molecule. Generally these changes are done on a few amino acids to minimize the alteration of the molecule. However, larger changes may be tolerated in certain circumstances.

The variants typically exhibit the same qualitative biological activity and will elicit the same immune response as the original variant BAFF protein, although variants also are selected to modify the characteristics of the variant BAFF proteins as needed. Alternatively, the variant may be designed such that the biological activity of the variant BAFF protein is altered. For example, glycosylation or phosphorylation sites may be altered or removed. Similarly, the biological function may be altered; for example, in some instances it may be desirable to have more or less potent BAFF activity.

The variant BAFF proteins and nucleic acids of the invention can be made in a number of ways. Individual nucleic acids and proteins can be made as known in the art and outlined below. Alternatively, libraries of variant BAFF proteins can be made for testing. In a preferred embodiment, sets or libraries of variant BAFF proteins may be generated in many ways known to those skilled in the art.

In a preferred embodiment, the different protein members of the variant BAFF library may be chemically synthesized. This is particularly useful when the designed proteins are short, preferably less than 150 amino acids in length, with less than 100 amino acids being preferred, and less than 50 amino acids being particularly preferred, although as is known in the art, longer proteins may be made chemically or enzymatically. See for example Wilken et al, Curr. Opin. Biotechnol. 9:412-26 (1998), hereby expressly incorporated by reference.

In a preferred embodiment, particularly for longer proteins or proteins for which large samples are desired, the library sequences are used to create nucleic acids such as DNA which encode the member sequences and which may then be cloned into host cells, expressed and assayed, if desired. Thus, nucleic acids, and particularly DNA, may be made which encodes each member protein sequence. This is done using well-known procedures. The choice of codons, suitable expression vectors and suitable host cells will vary depending on a number of factors, and may be easily optimized as needed.

In a preferred embodiment, multiple PCR reactions with pooled oligonucleotides are done. In this embodiment, overlapping oligonucleotides are synthesized which correspond to the full-length gene. Again, these oligonucleotides may represent all of the different amino acids at each variant position or subsets. In a preferred embodiment, these oligonucleotides are pooled in equal proportions and multiple PCR reactions are performed to create full-length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full-length sequences with the desired combinations of mutations in the desired proportions.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo may contain the codon for a single position being mutated, or for more than one position being mutated. The multiple positions being mutated must be close in sequence to prevent the oligo length from being impractical. For multiple mutating positions on an oligonucleotide, particular combinations of mutations may be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters may be carried out by a number of ways, e.g. by using known pattern recognition methods, comparisons of frequencies of occurrence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. Introduction to mathematical techniques in pattern recognition; N.Y., Wiley-Interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++/Abhijit S. Pandya, Robert B. Macy. Boca Raton, Fla.: CRC Press, 1996; Handbook of pattern recognition & computer vision/edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

Oligonucleotides with insertions or deletions of codons may be used to create a library expressing different length proteins. In particular computational sequence screening for insertions or deletions may result in secondary libraries defining different length proteins, which can be expressed by a library of pooled oligonucleotide of different lengths.

In another preferred embodiment, variant BAFF proteins of the invention are created by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences may also be an artificial set; for example, from a probability table (for example generated using SCMF) or a Monte Carlo set. Similarly, the "family" can be the top 10 and the bottom 10 sequences, the top 100 sequences, etc. This may also be done using error-prone PCR.

Thus, in a preferred embodiment, in silico shuffling is done using the computational methods described herein. That is, starting with two libraries or two sequences, random recombinations of the sequences may be generated and evaluated.

In a preferred embodiment variant BAFF proteins are chimeras formed from two or more naturally occurring BAFF proteins. In a particularly preferred embodiment, the chimeras are formed by joining one or more receptor contact region from one or more naturally occurring BAFF proteins with the amino acid sequence of another naturally occurring BAFF protein.

In a preferred embodiment, error-prone PCR is done to generate a library of variant BAFF proteins. See U.S. Pat. Nos. 5,605,793, 5,811,238, and 5,830,721, all of which are hereby incorporated by reference. This may be done on the optimal sequence or on top members of the library, or some other artificial set or family. In this embodiment, the gene for the optimal sequence found in the computational screen of the primary library may be synthesized. Error-prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error-prone PCR can be performed on the gene for the optimal sequence, in the presence of bias oligonucleotides, to create a DNA sequence library that reflects the proportion of the mutations found in the variant BAFF library. The choice of the bias oligonucleotides can be done in a variety of ways; they can chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions may be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild-type gene or other gene may be used, as is schematically depicted in the Figures. In this embodiment, a starting gene is used; generally, although this is not required, the gene is usually the wild-type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits. First, this generally requires fewer oligonucleotides and may result in fewer errors. Second, it has experimental advantages in that if the wild-type gene is used, it need not be synthesized.

Using the nucleic acids of the present invention, which encode a variant BAFF protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the variant BAFF protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the variant BAFF protein, a replacement of the naturally occurring secretory leader sequence is desired. In this embodiment, an unrelated secretory leader sequence is operably linked to a variant BAFF encoding nucleic acid leading to increased protein secretion. Thus, any secretory leader sequence resulting in enhanced secretion of the variant BAFF protein, when compared to the secretion of BAFF and its secretory sequence, is desired. Suitable secretory leader sequences that lead to the secretion of a protein are known in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from *Bacillus* are preferably used to express the fusion protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding a variant BAFF protein. As will be appreciated by those in the art, all combinations are possible and accordingly, as used herein, the combination of components, comprised by one or more vectors, which may be retroviral or not, is referred to herein as a "vector composition".

The variant BAFF nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®), electroporation, viral infection, etc. The variant BAFF nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The variant BAFF proteins of the present invention are produced by culturing a host cell transformed with an expression vector containing nucleic acid encoding a variant BAFF protein, under the appropriate conditions to induce or cause expression of the variant BAFF protein. The conditions appropriate for variant BAFF protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, *Neurospora*, BHK, CHO, COS, *Pichia pastoris*, etc.

In a preferred embodiment, the variant BAFF proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Alternatively, Kozak sequences, signal sequences and selectable markers may be used to modulate the expression properties.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, lymphoma, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogenous nucleic acid other than the variant BAFF nucleic acid.

The generation of variant BAFF proteins may also be generated in stable cell lines, as is well known in the art.

In a preferred embodiment, the variant BAFF proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the variant BAFF protein into mRNA. A bacterial promoter has a transcription initiation region that is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter may include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the variant BAFF protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a variant BAFF encoding nucleic acid, are preferred. The bacterial expression vector may also include a selectable marker gene to allow for the selection of bacterial strains that have been transformed. Suitable selection genes include genes that render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

In one embodiment, variant BAFF proteins are produced in insect cells. Expression vectors for the transformation of insect cells, and in particular, baculovirus-based expression vectors, are well known in the art.

In another preferred embodiment, variant BAFF protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, modified BAFF variants are covalently coupled to at least one additional BAFF variant via a linker to improve the dominant negative action of the modified domains. A number of strategies may be used to covalently link modified receptor domains together. These include, but are not limited to, linkers, such as polypeptide linkages between N— and C-termini of two domains, linkage via a disulfide bond between monomers, and linkage via chemical cross-linking reagents. Alternatively, the N— and C-termini may be covalently joined by deletion of portions of the N— and/or C-termini and linking the remaining fragments via a linker or linking the fragments directly.

By“linker”, “linker sequence”,“spacer”, “tethering sequence ” or grammatical equivalents thereof, herein is meant a molecule or group of molecules (such as a monomer or polymer) that connects two molecules and often serves to place the two molecules in a preferred configuration. In one aspect of this embodiment, the linker is a peptide bond. Choosing a suitable linker for a specific case where two polypeptide chains are to be connected depends on various parameters, e.g., the nature of the two polypeptide chains, e.g., whether they naturally oligomerize (e.g., form a dimer or not), the distance between the N— and the C-termini to be connected if known from three-dimensional structure determination, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. These linked BAFF proteins have constrained hydrodynamic properties, that is, they form constitutive dimmers, and thus efficiently interact with other naturally occurring BAFF proteins to form a dominant negative heterotrimer or a competitive inhibitor or an agonist.

The linker peptide should have a length that is adequate to link two BAFF variant monomers in such a way that they assume the correct conformation relative to one another so that they retain the desired activity as antagonists of the native BAFF protein. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred. See also WO 01/25277, incorporated herein by reference in its entirety.

In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains.

Useful linkers include glycine-serine polymers (including, for example, (GS)n, (GSGGS)n (SEQ ID NO:21), (GGGGS)n (SEQ ID NO:22), and (GGGS)n (SEQ ID NO:23), where n is an integer of at least one); glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, seine is hydrophilic and therefore able to solubilize what could be a globular glycine chain. Third, similar chains have been shown to be effective in joining subunits of recombinant proteins such as single chain antibodies.

Suitable linkers may also be identified by screening databases of known three-dimensional structures for naturally occurring motifs that can bridge the gap between two polypeptide chains. Another way of obtaining a suitable linker is by optimizing a simple linker, e.g., (Gly4Ser)n (SEQ ID NO:22), through random mutagenesis. Alternatively, once a suitable polypeptide linker is defined, additional linker polypeptides can be created by application of PDA® technology to select amino acids that more optimally interact with the domains being linked. Other types of linkers that may be used in the present invention include artificial polypeptide linkers and inteins. In another preferred embodiment, disulfide bonds are designed to link the two BAFF monomers at inter-monomer contact sites. In one aspect of this embodiment the two monomers are linked at distances <5 Angstroms. In addition, the variant BAFF polypeptides of the invention may be further fused to other proteins, if desired, for example to increase expression or stabilize the protein.

In one embodiment, the variant BAFF nucleic acids, proteins and antibodies of the invention are labeled. By “labeled” herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In an alternative embodiment, BAFF variants are designed using the computational techniques described above. In this alternative embodiment, non-naturally occurring BAFF monomer or dimer variants are generated to bind to the receptor. More preferably, these variants preferably bind to the receptor and receptor antagonize (or competitively inhibit) naturally occurring TNFSF molecules to bind to the receptor.

The dimer variants are more preferred as they substantially bind to the receptor interface. Preferred examples of these variants are modified at BAFF positions 143, 144, 146, 148, 172, 174, 192, 194, 196, 198, 200, 206, 207, 228, 230-237, 240-250, 271, 273, 275, 276, 278, 282, 284 and 285.

Once made, the variant BAFF proteins may be modified. Covalent and non-covalent modifications of the protein are included within the scope of the present invention. Such modifications may be introduced into a variant BAFF polypeptide by reacting targeted amino acid residues of the polypeptide with an organic derivatizing agent that is capable of reacting with selected side chains or terminal residues.

One type of covalent modification includes reacting targeted amino acid residues of a variant BAFF polypeptide with an organic derivatizing agent that is capable of reacting with selected side chains or the N— or C-terminal residues of a variant BAFF polypeptide. Derivatization with bifunctional agents is useful, for instance, for cross linking a variant BAFF protein to a water-insoluble support matrix or surface for use in the method for purifying anti-variant BAFF antibodies or screening assays, as is more fully described below. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W. H. Freeman & Co., San Francisco, pp. 79-86 (1983)], acetylation of the N-terminal amine, and amidation of any C-terminal carboxyl group.

Another type of covalent modification of the variant BAFF polypeptide included within the scope of this invention comprises altering the native glycosylation pattern of the polypeptide. "Altering the native glycosylation pattern" is intended for purposes herein to mean deleting one or more carbohydrate moieties found in native sequence variant BAFF polypeptide, and/or adding one or more glycosylation sites that are not present in the native sequence variant BAFF polypeptide.

Addition of glycosylation or phosphorylation sites to variant BAFF polypeptides may be accomplished by altering the amino acid sequence thereof. The alteration may be made, for example, by the addition of, or substitution by, one or more serine or threonine residues to the native sequence or variant BAFF polypeptide (for O-linked glycosylation sites). The variant BAFF amino acid sequence may optionally be altered through changes at the DNA level, particularly by mutating the DNA encoding the variant BAFF polypeptide at preselected bases such that codons are generated that will translate into the desired amino acids.

Addition of N-linked glycosylation sites to variant BAFF polypeptides may be accomplished by altering the amino acid sequence thereof. The alteration may be made, for example, by the addition of, or substitution by, one or more asparagine residues to the native sequence or variant BAFF polypeptide. The modification may be made for example by the incorporation of a canonical N-linked glycosylation site, including but not limited to, N—X—Y, where X is any amino acid except for proline and Y is preferably threonine, serine or cysteine. Another means of increasing the number of carbohydrate moieties on the variant BAFF polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the variant BAFF polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, and permeability across the blood brain barrier biological half-life, and the like. Such moieties or modifications of variant BAFF polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of variant BAFF comprises linking the variant BAFF polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192; 4,179,337; 5,183,550. These nonproteinaceous polymers may also be used to enhance the variant BAFF's ability to disrupt receptor binding, and/or in vivo stability.

In another preferred embodiment, cysteines are designed into variant or wild type BAFF in order to incorporate (a) labeling sites for characterization and (b) incorporate PEGylation sites. In a preferred embodiment, BAFF is chemically modified at a position selected from the following: 156, 159, 162, 176, 182, 190, 204, 222, 225, 267 and 269. Rational PEGylation may be used to determine optimal positions, size of polymer, type of modification of the protein to attach the PEG molecule. This approach is described in U.S. Ser. No. 60/459,094 filed Mar. 31, 2003 and U.S. Ser. No. 10/820,468, filed Mar. 31, 2004, entitled METHODS FOR RATIONAL PEGYLATION OF PROTEINS, both hereby incorporated by reference in their entirety.

For example, labels that may be used are well known in the art and include but are not limited to biotin, tag and fluorescent labels (e.g. fluorescein). These labels may be used in various assays as are also well known in the art to achieve characterization.

A variety of coupling chemistries may be used to achieve PEGylation, as is well known in the art. Examples include but are not limited to, the technologies of Shearwater and Enzon, which allow modification at primary amines, including but not limited to, lysine groups and the N-terminus. See, Kinstler et al, Advanced Drug Deliveries Reviews, 54, 477-485 (2002) and M J Roberts et al, Advanced Drug Delivery Reviews, 54, 459-476 (2002), both hereby incorporated by reference. Other techniques include coupling to cysteine residues via maleiimide functional moiety, either at native or engineered cysteines.

Other modifications may be made to the variant BAFF proteins of the present invention, including modifications to the protein that enhance stability, dosage administration (e.g., amphiphilic polymers, see WO 0141812A2, commercially available from Nobex Corporation), clearance (e.g., PEG, aliphatic moieties that effect binding to HSA), and the like.

Optimal sites for modification can be chosen using a variety of criteria, including but not limited to, visual inspection, structural analysis, sequence analysis and molecular simulation. Individual residues may be analyzed to identify mutational sites that will not disrupt the monomer structure. Then the distance from each side chain of a monomer to another subunit may be calculated to ensure that chemical modification will not disrupt oligomerization. It is possible that receptor binding disruption may occur and may be beneficial to the activity of the BAFF variants of this invention.

In another preferred embodiment, portions of either the N— or C-termini of the wild-type BAFF monomer are deleted while still allowing the BAFF molecule to fold properly. In addition, these modified BAFF proteins would substantially lack receptor binding and/or activation, and could optionally interact with other wild-type BAFF molecules or modified BAFF proteins to form trimers (or other oligomers) as described above.

More specifically, removal or deletion of from about 1 to about 55 amino acids from either the N or C termini of the extracellular domain of BAFF, or both, are preferred. A more preferred embodiment includes deletions of N-termini beyond residue 10 and more preferably, deletion of the first 47 N-terminal amino acids. The deletion of C-terminal leucine is an alternative embodiment.

In another preferred embodiment, the wild type BAFF or variants generated by the invention may be circularly permuted. All natural proteins have an amino acid sequence beginning with an N-terminus and ending with a C-terminus. The N— and C-termini may be joined to create a cyclized or circularly permutated BAFF proteins while retaining or improving biological properties (e.g., such as enhanced stability and activity) as compared to the wild-type protein. In the case of a BAFF protein, a novel set of N— and C-termini are created at amino acid positions normally internal to the protein's primary structure, and the original N— and C-termini are joined via a peptide linker consisting of from 0 to 30 amino acids in length (in some cases, some of the amino acids located near the original termini are removed to accommodate the linker design). In a preferred embodiment, the novel N— and C-termini are located in a non-regular secondary structural element, such as a loop or turn, such that the stability and activity of the novel protein are similar or enhanced relative to those of the original protein. The circularly permuted BAFF protein may be further PEGylated or glycosylated. In a further preferred embodiment PDA® technology may be used to further optimize the BAFF variant, particularly in the regions created by circular permutation. These include the novel N— and C-termini, as well as the original termini and linker peptide.

Various techniques may be used to permutate proteins. See U.S. Pat. No. 5,981,200; Maki K, Iwakura M., Seikagaku. January 2001; 73(1): 42-6; Pan T., Methods Enzymol. 2000; 317:313-30; Heinemann U, Hahn M., Prog Biophys Mol Biol. 1995; 64(2-3): 121-43; Harris M E, Pace N R, Mol Biol Rep. 1995-96; 22(2-3):115-23; Pan T, Uhlenbeck O C., 1993 Mar. 30; 125(2): 111-4; Nardulli A M, Shapiro D J. 1993 Winter; 3(4):247-55, EP 1098257 A2; WO 02/22149; WO 01/51629; WO 99/51632; Hennecke, et al., 1999, J. Mol. Biol., 286, 1197-1215; Goldenberg et al J. Mol. Biol 165, 407-413 (1983); Luger et al, Science, 243, 206-210 (1989); and Zhang et al., Protein Sci 5, 1290-1300 (1996); all hereby incorporated by reference.

In addition, a completely cyclic BAFF may be generated, wherein the protein contains no termini. This is accomplished utilizing intein technology. Thus, peptides can be cyclized and in particular inteins may be utilized to accomplish the cyclization.

Cyclization and circular permutation may be used to generate the dominant-negative activity, the competitive inhibition or the agonist activity of the BAFF proteins of the present invention.

Variant BAFF polypeptides of the present invention may also be modified in a way to form chimeric molecules comprising a variant BAFF polypeptide fused to another, heterologous polypeptide or amino acid sequence. In one embodiment, such a chimeric molecule comprises a fusion of a variant BAFF polypeptide with a tag polypeptide that provides an epitope to which an anti-tag antibody can selectively bind. The epitope tag is generally placed at the amino-or carboxyl-terminus of the variant BAFF polypeptide. The presence of such epitope-tagged forms of a variant BAFF polypeptide can be detected using an antibody against the tag polypeptide. Also, provision of the epitope tag enables the variant BAFF polypeptide to be readily purified by affinity purification using an anti-tag antibody or another type of affinity matrix that binds to the epitope tag. In an alternative embodiment, the chimeric molecule may comprise a fusion of a variant BAFF polypeptide with an immunoglobulin or a particular region of an immunoglobulin. For a bivalent form of the chimeric molecule, such a fusion could be to the Fc or Fab region of an IgG molecule. Other fusion entities include human serum albumin (HSA), hydrophilic peptides, fatty acid molecules, etc.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol. 8:2159-2165 (1988)]; the c-myc tag and the 8F9, 3 C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6): 547-553 (1990)]. Other tag polypeptides include the Flag-peptide [Hopp et al., BioTechnology 6:1204-1210 (1988)]; the KT3 epitope peptide [Martin et al., Science 255:192-194 (1992)]; tubulin epitope peptide [Skinner et al., J. Biol. Chem. 266: 15163-15166 (1991)]; and the T7 gene 10 protein peptide tag [Lutz-Freyermuth et al., Proc. Natl. Acad. Sci. U.S.A. 87:6393-6397 (1990)].

In a preferred embodiment, the variant BAFF protein is purified or isolated after expression. Variant BAFF proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the variant BAFF protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the variant BAFF protein. In some instances no purification will be necessary.

Once made, the variant BAFF proteins and nucleic acids of the invention find use in a number of applications. In a preferred embodiment, the variant BAFF proteins are administered to a patient to treat a BAFF related disorder.

By "BAFF related disorder" or "BAFF responsive disorder" or "condition" herein is meant a disorder that may be ameliorated by the administration of a pharmaceutical composition comprising a variant BAFF protein, including, but not limited to, autoimmune, inflammatory, immunological and oncological disorders. The variant BAFF proteins are major effectors in the pathogenesis of immune-regulated diseases.

In a preferred embodiment, the variant BAFF protein is used to treat for example, congestive heart failure (CHF), vasculitis, rosecea, acne, excema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; multiple myeloma; osteolytic bone cancers, breast cancer, lung cancer, kidney cancer and rectal cancer; bone metastasis, bone pain management, and humoral malignant hypercalcemia, ankylosing spondylitisa and other spondyloarthropathies; transplantation rejection, viral infections, hematologic neoplasisas and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemagiopericytoma), osteoporosis, hepatitis, HIV, AIDS, spondyloarthritis, rheumatoid arthritis, inflammatory bowel diseases (IBD), sepsis and septic shock, Crohn's Disease, psoriasis, schleraderma, graft versus host disease (GVHD), allogenic islet graft rejection, hematologic malignancies, such as multiple myeloma (MM), myelodysplastic syndrome (MDS) and acute myelogenous leukemia (AML), cancer and the inflammation associated with tumors, peripheral nerve injury or demyelinating diseases.

By "therapeutically effective dose" herein is meant a dose that produces the effects for which it is administered. The exact dose will depend on the purpose of the treatment, and will be ascertainable by one skilled in the art using known techniques. In a preferred embodiment, dosages of about 0.01 to about 50 µg/kg are used, administered either intravenously, subcutaneously, intratracheally or orally. As is known in the art, adjustments for variant BAFF protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, successful administration of a variant BAFF protein prior to onset of the disease results in "treatment" of the disease. As another example, successful administration of a variant BAFF protein after clinical manifestation of the disease to combat the symptoms of the disease comprises "treatment" of the disease. "Treatment" also encompasses administration of a variant BAFF protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

In another embodiment, a therapeutically effective dose of a variant BAFF protein, a variant BAFF gene, or a variant BAFF antibody is administered to a patient having a disease involving inappropriate expression of a BAFF protein. A "disease involving inappropriate expression of a BAFF protein" within the scope of the present invention is meant to include diseases or disorders characterized by aberrant BAFF proteins, either by alterations in the amount of BAFF protein present or due to the presence of mutant BAFF protein. An overabundance may be due to any cause, including, but not limited to, overexpression at the molecular level, prolonged or accumulated appearance at the site of action, or increased activity of BAFF protein relative to normal. Included within this definition are diseases or disorders characterized by a reduction of BAFF protein. This reduction may be due to any cause, including, but not limited to, reduced expression at the molecular level, shortened or reduced appearance at the site of action, mutant forms of BAFF protein, or decreased activity of BAFF protein relative to normal. Such an overabundance or reduction of BAFF protein can be measured relative to normal expression, appearance, or activity of BAFF protein according to, but not limited to, the assays described and referenced herein.

The administration of the variant BAFF proteins of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm or Inhance™ pulmonary delivery system commercially available from Inhale Therapeutics), vaginally, rectally, or intraocularly. In some instances, for example, in the treatment of wounds, inflammation, etc., the variant BAFF protein may be directly applied as a solution or spray. Depending upon the manner of introduction, the pharmaceutical composition may be formulated in a variety of ways.

Also, sustained release or controlled release formulations may be used for the compositions of the present invention. For example, ProLease® (commercially available from Alkermes) a microsphere-based delivery system composed of the desired bioactive molecule incorporated into a matrix of poly-DL-lactide-co-glycolide (PLG) and other pharmaceutically compatible polymeric matrices may be used to create sustained release formulations.

The concentration of the therapeutically active variant BAFF protein in the formulation may vary from about 0.1 to 100 weight %. In another preferred embodiment, the concentration of the variant BAFF protein is in the range of 0.003 to 1.0 molar, with dosages from 0.03,0.05, 0.1, 0.2, and 0.3 millimoles per kilogram of body weight being preferred.

The pharmaceutical compositions of the present invention comprise a variant BAFF protein in a form suitable for administration to a patient. In the preferred embodiment, the pharmaceutical compositions are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the variant BAFF proteins are added in a micellular formulation; see U.S. Pat. No. 5,833, 948, hereby expressly incorporated by reference in its entirety.

Combinations of pharmaceutical compositions may be administered. Moreover, the compositions may be administered in combination with other therapeutics.

In one embodiment provided herein, antibodies, including but not limited to monoclonal and polyclonal antibodies, are raised against variant BAFF proteins using methods known in the art. In a preferred embodiment, these anti-variant BAFF antibodies are used for immunotherapy. Thus, methods of immunotherapy are provided. By "immunotherapy" is meant treatment of a BAFF related disorders with an antibody raised against a variant BAFF protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with a variant BAFF protein antigen to which antibodies are raised. As appreciated by one of ordinary skill in the art, the variant BAFF protein antigen may be provided by injecting a variant BAFF polypeptide against which antibodies are desired to be raised into a recipient, or contacting the recipient with a variant BAFF protein encoding nucleic acid, capable of expressing the variant BAFF protein antigen, under conditions for expression of the variant BAFF protein antigen.

In another preferred embodiment, a therapeutic compound is conjugated to an antibody, preferably an anti-variant BAFF protein antibody. The therapeutic compound may be a cytotoxic agent. In this method, targeting the cytotoxic agent to tumor tissue or cells, results in a reduction in the number of afflicted cells, thereby reducing symptoms associated with cancer, and variant BAFF protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, variant BAFF proteins are administered as therapeutic agents, and can be formulated as outlined above. Similarly, variant BAFF genes (including both the full-length sequence, partial sequences, or regulatory sequences of the variant BAFF coding regions) may be administered in gene therapy applications, as is known in the art. These variant BAFF genes can include antisense applications, either as gene therapy (i.e. for incorporation into the genome) or as antisense compositions, as will be appreciated by those in the art.

In a preferred embodiment, the nucleic acid encoding the variant BAFF proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy, where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143-4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection [Dzau et al., Trends in Biotechnology 11:205-210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990). For review of gene marking and gene therapy protocols see Anderson et al., Science 256:808-813 (1992).

In another embodiment, variant BAFF genes are administered as DNA vaccines, either single genes or combinations of variant BAFF genes. Naked DNA vaccines are generally known in the art. Brower, Nature Biotechnology, 16:1304-1305 (1998). Methods for the use of genes as DNA vaccines are well known to one of ordinary skill in the art, and include placing a variant BAFF gene or portion of a variant BAFF gene under the control of a promoter for expression in a patient in need of treatment.

The variant BAFF gene used for DNA vaccines can encode full-length variant BAFF proteins, but more preferably encodes portions of the variant BAFF proteins including peptides derived from the variant BAFF protein. In a preferred embodiment a patient is immunized with a DNA vaccine comprising a plurality of nucleotide sequences derived from a variant BAFF gene. Similarly, it is possible to immunize a patient with a plurality of variant BAFF genes or portions thereof as defined herein. Without being bound by theory, expression of the polypeptide encoded by the DNA vaccine, cytotoxic T-cells, helper T-cells and antibodies are induced which recognize and destroy or eliminate cells expressing BAFF proteins.

In a preferred embodiment, the DNA vaccines include a gene encoding an adjuvant molecule with the DNA vaccine. Such adjuvant molecules include cytokines that increase the immunogenic response to the variant BAFF polypeptide encoded by the DNA vaccine. Additional or alternative adjuvants are known to those of ordinary skill in the art and find use in the invention.

All references cited herein, including patents, patent applications (provisional, utility and PCT), and publications are incorporated by reference in their entirety.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

BAFF Library Expression, Purification, and Activity Assays for BAFF Variants

Overnight culture preparation: Competent Tuner(DE3) pLysS cells in 96 well-PCR plates were transformed with 1 ul of BAFF library DNAs and spread on LB agar plates with 34 mg/ml chloramphenicol and 100 mg/ml ampicillin. After an overnight growth at 37 degrees C., a colony was picked from each plate in and inoculated into 15 ml 1.5 ml of CG media supplemented with 34 mg/ml chloramphenicol and 100 mg/ml ampicillin or carbenicillin kept in 96 deep well block. The block culture was shaken at 250 rpm at 37 degrees C. overnight.

Expression: The next day, the overnight cultures were diluted 1:50 into 2000 mL shake flasks containing 500 ml CG media supplemented with 100 mg/ml ampicillin or carbenicillin. Cells were grown at 30 C at 250 rpm until OD600=0.6-0.7 was reached at which time IPTG is added to final concentration of 1 mM. Subsequently the cultures are grown at 16 C for 12 hours or overnight.

Lysis: Cells were harvested by centrifugation in the centrifuge 0.5 L bottles at 10,000 g for 30'. The 24-well block was centrifuged at 3000 rpm for 10 minutes. The pellets were resuspended in lysis buffer (22.5 ml PBS pH 7.2, 2.5 ml 10X BugBuster, 8 ul Benzonase) and mixed gently andwas let stand for 10 min. at RT. The suspension was spun down at 30,000 g for 30 min. The supernatant was clarified using a 0.45 um syringe filter and kept on ice or at 4 C until ready for purification.

Batch binding and purification employing Anti-Flag M2 antibody resin: 5 ml of slurry of Anti-FLAG M2 antibody affinity resin (Sigma, #A220) was added to a BioRad Econo Pak column (20 ml) and washed with 25 ml of PBS pH=7.2. Then the resin was washed with 15 ml of 0.1 M glycine-HCl pH 3.0 and equilibrated with 25 CV PBS pH=7.2. After removal of PBS lysed supernatant was added to the resin, the Econo Pak was capped and incubated at room temperature for 1 hr with gentle agitation. Then the Econo Pak wasplaced vertically and the supernatant was drained by gravity. The resin was washed with 25 ml of PBS. Theremaining beads were rinsed off with 0.5 ml column buffer and transferred into a column. Protein from the resin was eluted with 10 ml of elution buffer (100 ug/ml FLAG peptide (Sigma, #F3290) diluted in PBS pH=7.2). The resin was washed with 5 CV 100 mM glycine pH 3.0.

Purification of His-BAFF variants employing Ni NTA column resin: The pellets were resuspended in 70 ml of lysis buffer (50 mM NaH2PO4, 300 mM NaCl, 10 mM imidazole). After freezing at −80 degrees C. for 20 minutes and thawing at 37 C twice, MgCl$_2$ was added to 10 mM, and DNase I to 75 mg/ml. The mixture is incubated at 37 C for 30 minutes. Purification was carried out following the Qiagen Ni NTA spin column purification protocol for native condition. The purified protein was dialyzed against 1×PBS for 1 hour at 4 degrees C. four times. Dialyzed protein was filter sterilized, using Millipore multiscreenGV filter plate to allow the addition of protein to the sterile mammalian cell culture assay later on.

BAFF purification of untagged and mvc-tagged proteins Cells were lysed in lysis buffer with sonication (25 mM Tris pH 7.5, 25 mM MgCl2, 10% glycerol) and spun at 30,000 g for 15 min at 4 C. The supernatant was filtered through 0.45 um filter, passed over a QHP column (Amersham Bioscience), and eluted with a linear gradient of NaCl 0-500 mM in 20 Column Volumes of elution buffer (25 mM Tris pH 7.5, 25 mM MgCl2, 10% glycerol). The fractions were analyzed by SDS-PAGE and the most concentrated fractions were pooled. The pH was lowered and diluted with the following procedure: 1. Added equal volume of 10% glycerol in milliQ water to pooled fractions; 2. Added $MgCl_2$ to 25 mM final concentration; 3. Decreased conductivity to <7 mS/cm with additional 10% glycerol in milliQ water; 4. Added 0.1 volume of 10×Citrate Buffer (250 mM sodium citrate at pH4.0) and 5. Filtered solution. The filtered solution was passed over a Resource S column (Amersham Bioscience), eluted with a linear gradient of NaCl 0-500 mM in 20 Column Volumes of elution buffer (25 mM sodium citrate pH 4.0, 25 mM MgCl2, 10% glycerol), and fractions were analyzed by SDS-PAGE. The cleanest fractions were pooled and concentrated. Then they were dialyzed into aformulation buffer (2 m mM sodium citrate, 25 mM MgCl2, 100 mM NaCl, 10% glycerol, pH=7.0).

Quantification: Purified proteins were quantified by BCA protein assay (Pierce Biotechnology, #23227) according to the manufacturer's protocol. All measurements were performed in triplicate.

Example 2

In vitro BAFF Bioassay

B cell Durification: The human peripheral blood mononuclear cells were obtained from leukophoresis pack of consenting donors by running through the standard ficoll gradient. The B cells were obtained from PBMC fraction by negative depletion of non-B cells from PBMC using the magnetic labeling-purification system (MACS™ technology from Miltenyi Biotec, Germany). The resulting B-cells are ready for use in either B cell proliferation/viability assay.

B cell proliferation/viability (agonist) assay using Titer-Glo Luminescent Cell Viability Assay kit (Promega, Inc., Wis., U.S.A.): Cross-linking with an anti-Flag M2 mAb improves the dynamic range of the assay and results in similar or increased activity of Flag-BAFFs relative to that of untagged BAFF(wt). The signal remained the same in the range of 0.75-3 mg/ml of anti-Flag M2 antibody. 5,500-7,500 purified B cells in RPMI1649 (supplemented with 10% FBS) were added in 25 ul aliquots into well of 384 micro-titer plates with. Various amounts of BAFF (in the range of 100 ng/ml -0.005 ng/ml) were added to cells; 2 mg/ml of anti-m antibody was added as a co-stimulator. If BAFF preparations had Flag-tag, the M2 anti-Flag antibody was added to the constant concentration of 2 mg/ml. The plate is then incubated at 37° C. with 5% CO2 for 4 days. After 4 days of incubation, 25 ml of luminescence substrate/buffer solution of Cell Titer-Glo kit was added and the resulting luminescence was detected using a standard luminometer. The data was plotted using Prizm.

Assay specificity was confirmed by using BAFF-specific soluble commercial BAFF receptor-Fc fusions as antagonists and FlagBAFF(wt), FlagBAFF(F220S), FlagBAFF(F220S/E223K). The antagonistic activities of both BAFF-R/Fc and BCMA/Fc were similar and 2 to 3 logs lower than that of TACI/Fc. Converse experiment was performed using Flag-BAFF(F220S): soluble BAFF receptors were held at constant 10 mg/ml and varying amounts of Flag-BAFF(F220S) were added. Similar results were obtained: TACI/Fc inhibited BAFF activity completely up to 500 ng/ml of BAFF whereas BAFF-R/Fc and BCMA/Fc displayed 2 to 3 log lower potency than that of TACI/Fc.

Donor-to-donor reproducibility was assessed by using PBMCs isolated from two different donors. Proliferation response to Flag-F220S-BAFF or Flag-F220S/E223K-BAFF was similar in PBMC preparations obtained from either donor indicating that the assay is stable and reproducible.

Antagonist assay using Titer-Glo Various proteins including the Fc fusions of BAFF receptors (BAFF-R, BCMA, and/or TACI) and BAFF variants were used to antagonize the BAFF induced cell proliferation using the above-described B cell proliferation/viability assay. The purified B cells were incubated with a fixed amount of agonist such as wild type BAFF in the presence of variable amount of the antagonist for 4 days at 37° C. incubator with 5% CO2.

B cell proliferation (agonist) assay using Cell Proliferation ELISA, BrdU (chemiluminescence) kit, Roche Diagnostics, #1 669 915): B-cells were incubated in the presence of various concentrations (10-0.00001 ug/ml) of BAFF wt or BAFF variants in a white 96-well MTP (tissue culture grade; flat, clear bottom) at a final volume of 100 ul/well in a humidified atmosphere at 37° C. The incubation period of the microcultures depends on the particular experimental approach and on the cell type used for the assay. For most experimental setups, an incubation period of 24 to 120 h is appropriate.

Labeling the cells with BrdU: 10 ul/well BrdU labeling solution was added if the cells were cultured in 100 ul/well (final concentration: 10 uM BrdU) and the cells were incubated for an additional 2 to 24 h at 37° C. (if the cells were cultured in 200 ul/well, add 20 ul/well BrdU labeling solution).

Removal of labeling medium: The MTP was centrifuged at 300×g for 10 min and the labeling medium was removed by flicking off or suction using a canulla. Cells were dried using a hair-dryer for about 15 min or, alternatively, at 60° C. for 1 h.

Cell fixation and DNA denaturation: 200 ul/well FixDenat was added to the cells and they wre incubated for 30 min at 15 25° C.

Incubation with anti- BrdU-POD: FixDenat solution was removed thoroughly by flicking off and tapping. 100 ul/well anti-BrdU-POD working solution was added and the solution was incubated for approx. 90 min at 15-25° C. Alternatively, this incubation period can be varied between 30-120 min, depending on individual requirements.

Washing: The antibody conjugate was removed by flicking off and the wells were rinsed three times with 200-300 ul/well washing solution.

Substrate reaction: The washing solution was removed by tapping, theclear bottom was sealed with black adhesive foil and 100 ul/well substrate solution was added to each well with a multi-channel pipette. Then the contents were incubated at 15-25° C. for at least 3 min on a shaker.

Measurement: The light emission of the samples was measured in a microplate luminometer with photomultiplier technology.

Using the above-described assay it was demonstrated that the activity of all Flag-BAFFs (wt, F220S, E223K, and F220S/E223K) and especially Myc-BAFF(wt) was consistently lower than that of the untagged proteins. However, removing Flag-tag from BAFF proteins resulted in restoration of full activity seen with commercial preparations of untagged BAFF.

Example 3

Binding Assay (Plate Format)

Biotinylation of BAFF wasperformed by adding 20 molar excess Sulfo-NHS-LC-biotin to the protein sample and incubating the sample on ice for 2 hours. Excess biotin was removed from the sample by dialysis. Coupling ratios ranged between about 1 to about 4. The protein concentration of biotinylated BAFF was determined by BCA protein assay (Pierce). Wells of a microtiter plate were coated with anti-FLAG antibody at a concentration of 2.5 mg/ml and blocked with 3% BSA overnight at 4° C. The FLAG-tagged protein BAFFR, or TACI, or BCMA receptors were added at a concentration of 10 ng/ml in PBS +1% BSA to wells of the anti-FLAG-coated microtiter plate, and the plate was incubated for 2 hours at room temperature. Biotinylated BAFF proteins ranging in concentrations from 0-1 mg/mL were added in quadruplicate to anti-FLAG- BAFFR, or TACI, or BCMA receptors coated wells to represent total binding. Non-specific binding was measured by adding biotinylated BAFF proteins ranging in concentrations from about 0-1 µg/ml in quadruplicate to wells coated only with anti-FLAG antibody. Binding was allowed to occur overnight at +4° C. to ensure equilibrium. Alkaline phosphatase conjugated neutravidin (Pierce) was added to the wells at 1:10,000 dilution in PBS+1% BSA and incubated for 30 min at room temperature. Luminescence was detected upon the addition of the CSPD star substrate (Applied Biosystems, Foster City, Calif.) and was measured (Wallac VICTOR, Perkin Elmer Life Sciences, Boston, Mass.). The specific binding of BAFF was calculated by subtracting non-specific binding from total binding. Data is fit to the binding equation $y=(BLmax*x)/(Kd+x)$.

Binding Assay (Alpha Screen format): Biotinylation of BAFF was performed by adding 20-fold molar excess Sulfo-NHS-biotin to protein sample and incubating 30 minutes at room temperature. Excess biotin was removed from the sample by dialysis. Coupling ratios ranged between about 1 and about 4. The protein concentration of biotinylated BAFF was determined by BCA Protein assay (Pierce). BAFF variant proteins ranging in concentrations from 1 pM to 100 nM, biotinylated BAFF at 0.5 nM, either BAFF-R/Fc, TACI/Fc, or BCMA/Fc chimera (R&D Systems) at 0.5 nM, and AlphaScreen protein A acceptor beads (Perkin Elmer LAS) at 20 ug/mL, all in assay buffer [100 mM Tris (pH 8.0), 0.01% Tween-20, 0.1% BSA], were added together in a 96 well reaction plate and incubated for one hour at room temperature. AlphaScreen streptavidin donor beads (Perkin Elmer LAS) at 20 ug/mL in assay buffer was added to the reactions and incubated for two hours at room temperature, then transferred to a white, 384-well plate and read in a Packard Fusion multiplatform platereader (Perkin Elmer LAS).

The competition of BAFF variants in the binding assay was plotted in GraphPad Prism and fit to a nonlinear regression for one site competition to determine EC50 Binding properties of in house produced Flag-BAFF and 10×His-BAFF (which is represented by 60-mer species) were identical to BAFF purchased from Biosource and Peprotech (FIG. 5). BAFF specifically binds to BAFF-R. APRIL, TNFa, and the reaction buffer show no apparent binding in the alpha screen assay.

Competition experiments between tested cytokine (His-BAFF, Flag-BAFF) and a soluble receptor (TACI and BCMA) showed that the binding curves by BAFF-biotin and TACI are superimposable. BCMA did not show any binding/competition.

Flag-tagged BAFF proteins bind to BCMA with lower affinity compared to His-tagged BAFFs. However, all BAFFs bind equally well to both BAFFR and TACI. DE-loop variants had similar binding to BAFF-R and TACI but displayed reduced binding to BCMA. His-BAFFs bound BCMA 10-fold tighter than Flag-BAFFs. Interestingly, differences in binding to BAFF-R and TACI are not affected by oligomerization state (60-mer vs. 3-mer) since 10×HisBAFF (60-mer) has an identical profile as 10×His-Long-BAFF (3-mer).

Example 4

Effects of N-Terminal Tags on Oligomerization Properties BAFF

Previous reports have shown that fusion tags may affect oligomerization state. Two N-terminally tagged BAFF proteins (a Flag- and a His-tag) were analyzed by SEC. Our findings indicate that BAFF weretrimeric under physiological conditions, and that an N-terminal His-tag promotes formation of the observed higher order oligomers.

We determined the oligomeric state of three distinct versions of the BAFF extracellular domain (ECD): a soluble TNF homology domain of BAFF (THD, residues 134-285), and two N-terminally tagged THD of BAFF: His-BAFF and Flag-BAFF. The His-tagged and Flag-tagged BAFF constructs were engineered with a Factor Xa protease site between the tag and THD of BAFF. Additionally, the untagged BAFF construct was made.

Proteins were expressed in E.coli (BL21), purified using affinity chromatography, and assayed by SEC in 25 mMTris, 100 mM NaCl, 10% glycerol pH=8.0. This pH was chosen in order to assay BAFF oligomerization in a buffer that would favor formation of higher order oligomers. SEC was performed in 25 mM Tris pH 8.0, 25 mM $MgCl_2$, 100 mM NaCl, 10% glycerol. The SEC traces confirmed that the His-tagged protein formed well-defined oligomers with a size of >1000 kDa (MW[60-mer His-BAFF]=1180 kDa), similar to the previous reports. However Flag-BAFF was found to be a trimeric protein with an apparent MW of approximately 62 kDa (MW [trimer Flag-BAFF]=58 kDa). To further understand the modes of oligomerization of BAFF proteins with different N-terminal affinity tags, we sought to determine whether the Flag-tag was preventing formation of higher order oligomers of naturally oligomeric BAFF, or conversely if the His-tag was causing the protein to form 60-mers. Using Factor Xa, we proteolytically cleaved the tags and analyzed the digested samples by SEC.

Flag-tag had no effect on the oligomerization state of BAFF. In contrast, removal of the His-tag resulted in the formation of a trimeric BAFF species, suggesting that this tag promotes formation of higher order oligomers. The pH dependence of the trimer/oligomer transition observed previously tracks ionization properties of the indole ring of His residue (pKa[His] ~6.0-7.0). Thus, an uncharged N-terminal tag (His-tag above pKa[His]) may facilitate oligomerization, whereas a positively charged His-tag (His-tag above pKa [His]) or a negatively charged Flag-tag do not perturb the oligomerization properties of BAFF. Gel filtration standards (thyroglobulin [670 kDa], gamma globulin [158 kDa], ovalbumin [44 kDa], myoglobin [17 kDa] were used to plot a standard curve to estimate apparent molecular weights of BAFF proteins.

Our results indicate that BAFF was trimeric under physiological conditions similar to the other members of the TNFSF of ligands. Additionally, the presence of an N-terminal tag greatly influenced the oligomerization state of BAFF, and that the buffer pH was inconsequential to a trimer/oligomer transition, in contrast to what has been reported previously. The removal of the His-tag results in the disappearance of the 60-meric cage species with the concomitant appearance of trimeric BAFF. This illustrates the need to carefully select and test fusion tags for each protein system to ensure that the tags do not perturb the physical chemical properties of the host protein.

Depending on the sequence at the N-terminus of BAFF (untagged or tagged) and the formulation buffers for BAFF protein preparations BAFF has a propensity to aggregate or to form structured higher order oligomers. On the other hand, DE-loop has been implicated (Liu et all, Cell, 2002) to be crucial for formation of higher oligomers. They suggested that Δ217-224 BAFF variant had wt binding to BCMA and that this deletion eliminated the propensity to form 60-mers so that it formed only a mixture of trimers and monomers. All crystal structures of BAFF complexes with its receptors (Liu et al, Kim et al) show no receptor interactions with the DE-loop. Therefore, we made several DE-loop point mutations to identify variants that will not oligomerize as readily as the wt. This was important for (i) screening of a potential DN antagonist library made in the scaffold of a variant with better monomer exchanging properties. These variants should have much increased Kd (trimerization) and thus are more likely to readily exchange. Since DE-loop variants have wt receptor binding they are likely to have similar bioactivity and (ii) solving the problem with the aggregation of BAFF and thus assisting with the practical aspects of library purification and screening.

Disruption of DE loop "handshake": Substitutions F220S, E223K, and F220S/E223Qwere expressed and purified. However, His-tagged E223K was expressed approximately 3-4 fold and F220S and F220S/E223K were expressed approximately 10-fold better than His-BAFF. Similar increase in expression of Flag-BAFF variants was observed also.

All proteins were assayed using SEC. All Flag-BAFF variants (Flag(F220S), Flag(E223K), and Flag(F220S/E223K)) had spectra similar to Flag(wt). All these proteins produced a single band on native gels. There was almost no observable aggregates present in any of the Flag(DE loop) variants. His (F220S), His (E223K), and His(F220S/E223K) were mostly represented by the oligomer and a small amount of trimer.

Effect of Untagged BAFF: SEC analysis confirmed that untagged BAFF purified by us and the commercially available protein (Biocarta) were also trimeric with an apparent MW of 45 kDa.

Example 5

BAFF Exchange—Native Gels

Two types of exchange reactions were tested: 1) two DE-loop variants were used in an exchange reaction, HisBAFF (F220S/E223K) and FlagBAFF(F220S), or 2) FlagBAFF (F220S) and untagged BAFF(wt). The reaction was monitored at 24, 72 and 168 hrs time points. The buffer in the exchange reaction was: 25 mM NaCitrate, pH7+25 mM MgCl+100 mM NaCl+10% glycerol. Western blot with the anti-Flag and anti His antibodies confirmed that all new bands were heterotrimers. The exchange bands were visible after 24 hrs incubation. After 168 hrs (7 days) the reaction reached equilibrium.

Since efficient exchange between the DE-loop variant, FlagBAFF- (F220S), and Untagged BAFF(wt) was observed, this showed that the wild type also can exchange as the DE-loop variants with His(F220S/E223K). This suggests that mechanisms alternative to the dissociation/re-association type of exchange should be considered.

BAFF exchange—anisotroDv assay: In order to measure the kinetics of exchange between BAFF trimers in solution a novel spectroscopic assay was developed. This technique utilizes the polarization anisotropy differences between homotrimers of fluorescently modified BAFF and heterotrimers formed between fluorescent and unlabeled BAFF molecules. Since this assay is carried out in a real-time sampling device, we could measure the formation of BAFF heterotrimers as a function of time. Furthermore, this assay is sensitive to a variety of buffers and/or excipients thereby enabling a detailed kinetic analysis of BAFF exchange in solution.

This assay necessitates a fluorescently labeled BAFF trimer that at limiting concentrations could be used as a tracer to monitor exchange. We generate a BAFF variant specifically labeled it with Alexa568 maleimide. Polarization anisotropy measures heterotrimer formation at steady state. We mix 1 ug/mL Alexa568 BAFF either alone or with increasing concentrations of RANK-L, or BAFF variants in 25 mM NaCitrate, pH7+25 mM MgCl+100 mM NaCl+10% glycerol for 3 days at 37 C. These reactions are placed into the spectroscopic instrument and the steady-state anisotropy is measured. This experiment demonstrates the specificity (no observed exchange between Alexa568 BAFF and RANK-L) and utility of this assay (pre and post steady-state). We mixed together 1 ug/mL Alexa568 BAFF alone or with 100 ug/mL BAFF variants in a 96-well assay format and begin anisotropy measurements.

Next, we characterized the spectral properties of this modified BAFF and finally demonstrated that we could use it to measure exchange between Alexa568 and unlabeled BAFFs. Polarization anisotropy demonstrates heterotrimer formation between BAFF homotrimers. We mix 1 ug/mL Alexa568 BAFF alone or with 0.1 ug/mL, 1 ug/mL, 3 ug/mL, 5 ug/mL, 7 ug/mL, 10 ug/mL, or 50 ug/mL BAFF variant in 96-well assay format. The plate is placed into the instrument to begin anisotropy measurements. Once the time-course is completed the end-point samples are analyzed using native PAGE to determine the extent of Alexa568 BAFF sequestration into heterotrimers. Native PAGE analysis demonstrates that the anisotropy changes correlate perfectly with the decreased mobility of BAFF heterotrimers on these gels.

Furthermore, this assay has further utility because it is compatible with both modified (i.e. PEGylated) and unmodified cold BAFFs, and it is highly specific for exchange between BAFFs (i.e. BAFF fails to exchange with RANKL). Finally, other methods require either solid-phase (i.e. sandwich ELISA or RIA), or acrylamide gels (i.e. native PAGE analysis or IEF) to resolve the end products of heterotrimer formation. This assay is superior to currently utilized methods because it allows kinetic analysis in solution. The assay provides unexpected results in that we can measure a change in polarization anisotropy without any apparent change in molecular weight (i.e. exchange between Alexa568 BAFF and cold variant BAFF). Our experimental analysis suggests that there is an appreciable amount of fluorescent enhancement observed upon heterotrimer formation. We exploit this change with the aid of polarizing filters to increase sensitivity and generate the anisotropy differences shown in the above examples.

The following references are incorporated by references in their entirety:

Yu, G., et al Nature Immunology 2000, 1: 252-256

Mackay, F. and Kalled, S. Current Opinion in Immunology 2002, 14:783-790

Mackay, F. and Mackay, C. TRENDS in Immunology 2002, 23:113-115

Vaux, D. J. Clin. Investigation 2002, 109:17-18

Kayagaki, N., et al. Immunity 2002, 10, 515-524

Gross, J., et al. NATURE 2000, 404:995-999

Seshasayee, D., et al. Immunity 2003, 18: 279-288

Yan, M., et al Nature Immunology 2000, 1:37-41

Zhang, J., et al. The Journal of Immunology 2001, 166:6-10

Oren, D., et al. Nature Structural Biology 2002, 9:288-292

Moore, P., et al. Science 1999, 285:260-263

Roschke, V., et al. The Journal of Immunology 2002, 169: 4314-4321

Do, R., and Chen-Kiang, C. Cytokine & Growth Factor Reviews 2002, 13:19-25

Schneider, P., et al. The Journal of Experimental Medicine 1999, 189:1747-1756

Groom, J., et al The Journal of Clinical Investigation 2002, 109:59-68

Khare, S. and Hsu, H. TRENDS in Immunology 2001, 22:61

Mackay, F. and Browning, J. Nature Reviews Immunology 2002, 2:465-475

Kanakaraj, P. et al. *Cytokine,* 12, 25-31 (2001)

Karpusas, M. et al. *J. Mol. Biol.,* 315, 1145-1154 (2002)

Oren, D. A. et al. *Nature Struct. Biol.,* 9, 288-292 (2002)

Liu, Y, et al. *Nature,* 423, 49-56, (2003)

Kim, H. M. et al. *Nature Struct. Biol.,* 10, 342-348 (2003)

Liu, Y. et al. *Cell,* 108, 383-394 (2002)

Wu, J. and Filutowicz, M. *Acta Biochim Pol.* 46, 591-599 (1999)

All references cited herein are incorporated by reference in their entirety.

Whereas particular embodiments of the invention have been described above for purposes of illustration, it will be appreciated by those skilled in the art that numerous variations of the details may be made without departing from the invention as described in the appended claims. All references cited herein are expressly incorporated by reference.

---

We claim:

1. An isolated B cell Activation Factor (BAFF) protein wherein the BAFF variant differs from residues 144-284 of wild type human BAFF corresponding to residues 1-141 set forth in SEQ ID NO: 8 by two or three amino acid substitutions, wherein one of the substitutions is F220S, and wherein the BAFF variant has reduced BAFF receptor binding relative to wild-type human BAFF comprising SEQ ID NO: 8 and the BAFF receptor is selected form the group consisting of BAFFR, TACI and BCMA.

2. The variant BAFF protein according to claim 1, wherein the second or third amino acid substitution is selected from the group consisting of: Q159D, Q159E, Q159K, Q159R, S162D, S162L, S162N, Y163A, Y163D, Y163E, Y163F, Y163H, Y163I, Y163K, Y163L, Y163R, Y163T, D203E, D203G, D203K, D203N, D203S, K204E, K204Q, T205A, T205D, T205I, T205K, T205L, T205N, T205S, Y206A, Y206E, Y206F, Y206I, Y206K, Y206Q, Y206S, A207S, A207T, L211D, L211E, L211K, L211V, T228N, T228V, R231 K, I233A, I233E, I233L, I233Q, I233T, I233V, I233Y, E238K, E238Q, L240A, L240F, L240K, L240N, L240R, L240Y, N242A, N242S, N242Y, P264A, P264D, P264N, R265A, R265H, R265K, R265L, E266A, E266D, E266I, E266K, E266L, E266Q, E266R, E266T, N267R, N267S, Q269E, Q269H, Q269K, S271E, S271R, D273A, D273E, D273H, D273N, D273R, D275A, D275E, D275H, D275K, D275N, D275R, and D275V.

3. The variant BAFF protein according to claim 1, wherein the second or third amino acid substitution is selected from the group consisting of: Q159E, Q159D, Y163E, Y163K, Y163R, D203S, D203N, D203E, K204E, K204Q, T205A, T205K, T205N, T205S, T205D, T205L, Y206A, Y206E, Y206K, Y206Q, Y206S, Y206I, A207S, L211K, L211D, T228N, T228V, R231K, I233A, I233E, I233T, I233Q, I233Y, 264N, 264D, 264A, R265A, R265K, R265L, R265H, E266Q, E266D, N267S, S271R, D275A, D275V, D275K, D275R, D275H, and D275N.

4. The variant BAFF protein according to claim 1, wherein the second or third amino acid substitution is selected from the group consisting of: T205D, Y206K, I233E, I233Y, R265K, D275A, and D275R.

5. The variant BAFF protein according to claim 1, wherein the second or third amino acid substitution is T205D.

6. The variant BAFF protein according to claim 1, wherein the second or third amino acid substitution is Y206K.

7. The variant BAFF protein according to claim 1, wherein the second or third amino acid substitution is I233E.

8. The variant BAFF protein according to claim 1, wherein the second or third amino acid substitution is I233Y.

9. The variant BAFF protein according to claim 1, wherein the second or third amino acid substitution is R265K.

10. The variant BAFF protein according to claim 1, wherein the second or third amino acid substitution is D275A.

11. The variant BAFF protein according to claim 1, wherein the second or third amino acid substitution is D275R.

* * * * *

UNITED STATES PATENT AND TRADEMARK OFFICE
CERTIFICATE OF CORRECTION

PATENT NO.       : 7,553,930 B2
APPLICATION NO.  : 10/794751
DATED            : June 30, 2009
INVENTOR(S)      : John Desjarlais, Adam Read Thomason and Eugene Alexander Zhukovsky It is certified that error appears in the above-identified patent and that said Letters Patent is hereby corrected as shown below:

Column 67, Claim 1, line no. 19 should read:

BAFF receptor is selected [form] --from-- the group consisting of

Column 67, Claim 2, line no. 31 should read:

[R231 K]--R231K--n, 1233A, 1233E, 1233L, 1233Q, 1233T, 1233V, 1233Y

Signed and Sealed this

First Day of June, 2010

David J. Kappos
*Director of the United States Patent and Trademark Office*

SEQUENCE LISTING

```
<160> NUMBER OF SEQ ID NOS: 23

<210> SEQ ID NO 1
<211> LENGTH: 147
<212> TYPE: PRT
<213> ORGANISM: Homo sapiens

<400> SEQUENCE: 1

Lys Pro Val Ala His Val Val Ala Asn Pro Gln Ala Glu Gly Gln Leu
1               5                   10                  15

Gln Trp Leu Asn Arg Arg Ala Asn Ala Leu Leu Ala Asn Gly Val Glu
            20                  25                  30

Leu Arg Asp Asn Gln Leu Val Val Pro Ser Glu Gly Leu Tyr Leu Ile
        35                  40                  45

Tyr Ser Gln Val Leu Phe Lys Gly Gln Gly Cys Pro Ser Thr His Val
    50                  55                  60

Leu Leu Thr His Thr Ile Ser Arg Ile Ala Val Ser Tyr Gln Thr Lys
65                  70                  75                  80

Val Asn Leu Leu Ser Ala Ile Lys Ser Pro Cys Gln Arg Glu Thr Pro
                85                  90                  95

Glu Gly Ala Glu Ala Lys Pro Trp Tyr Glu Pro Ile Tyr Leu Gly Gly
            100                 105                 110

Val Phe Gln Leu Glu Lys Gly Asp Arg Leu Ser Ala Glu Ile Asn Arg
        115                 120                 125

Pro Asp Tyr Leu Asp Phe Ala Glu Ser Gly Gln Val Tyr Phe Gly Ile
    130                 135                 140

Ile Ala Leu
145

<210> SEQ ID NO 2
<211> LENGTH: 144
<212> TYPE: PRT
<213> ORGANISM: Homo sapiens
```

```
<400> SEQUENCE: 2

Lys Pro Ala Ala His Leu Ile Gly Asp Pro Ser Lys Gln Asn Ser Leu
1               5                   10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
    50                  55                  60

Ser Ser Pro Leu Tyr Leu Ala His Glu Val Gln Leu Phe Ser Ser Gln
65                  70                  75                  80

Tyr Pro Phe His Val Pro Leu Leu Ser Ser Gln Lys Met Val Tyr Pro
                85                  90                  95

Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140

<210> SEQ ID NO 3
<211> LENGTH: 138
<212> TYPE: PRT
<213> ORGANISM: Homo sapiens

<400> SEQUENCE: 3

Arg Lys Val Ala His Leu Thr Gly Lys Ser Asn Ser Arg Ser Met Pro
1               5                   10                  15

Leu Glu Trp Glu Asp Thr Tyr Gly Ile Val Leu Leu Ser Gly Val Lys
            20                  25                  30

Tyr Lys Lys Gly Gly Leu Val Ile Asn Glu Thr Gly Leu Tyr Phe Val
        35                  40                  45

Tyr Ser Lys Val Tyr Phe Arg Gly Gln Ser Cys Asn Asn Leu Pro Leu
    50                  55                  60

Ser His Lys Val Tyr Met Arg Asn Ser Lys Tyr Pro Gln Asp Leu Val
65                  70                  75                  80

Met Met Glu Gly Lys Met Met Ser Tyr Cys Thr Thr Gly Gln Met Trp
                85                  90                  95

Ala Arg Ser Ser Tyr Leu Gly Ala Val Phe Asn Leu Thr Ser Ala Asp
            100                 105                 110

His Leu Tyr Val Asn Val Ser Glu Leu Ser Leu Val Asn Phe Glu Glu
        115                 120                 125

Ser Gln Thr Phe Phe Gly Leu Tyr Lys Leu
        130                 135

<210> SEQ ID NO 4
<211> LENGTH: 148
<212> TYPE: PRT
<213> ORGANISM: Homo sapiens

<400> SEQUENCE: 4

Asn Pro Ala Ala His Leu Thr Gly Ala Asn Ser Ser Leu Thr Gly Ser
1               5                   10                  15

Gly Gly Pro Leu Leu Trp Glu Thr Gln Leu Gly Leu Ala Phe Leu Arg
            20                  25                  30

Gly Leu Ser Tyr His Asp Gly Ala Leu Val Val Thr Lys Ala Gly Tyr
```

-continued

```
                35                  40                  45
Tyr Tyr Ile Tyr Ser Lys Val Gln Leu Gly Gly Val Gly Cys Pro Leu
 50                  55                  60

Gly Leu Ala Ser Thr Ile Thr His Gly Leu Tyr Lys Arg Thr Pro Arg
 65                  70                  75                  80

Tyr Pro Glu Glu Leu Glu Leu Val Ser Gln Gln Ser Pro Cys Gly
                 85                  90                  95

Arg Ala Thr Ser Ser Ser Arg Val Trp Trp Asp Ser Ser Phe Leu Gly
                100                 105                 110

Gly Val Val His Leu Glu Ala Gly Glu Val Val Arg Val Leu
                115                 120                 125

Asp Glu Arg Leu Val Arg Leu Arg Asp Gly Thr Arg Ser Tyr Phe Gly
            130                 135                 140

Ala Phe Met Val
145

<210> SEQ ID NO 5
<211> LENGTH: 140
<212> TYPE: PRT
<213> ORGANISM: Homo sapiens

<400> SEQUENCE: 5

Asn Gln Phe Pro Ala Leu His Trp Glu His Glu Leu Gly Leu Ala Phe
  1               5                  10                  15

Thr Lys Asn Arg Met Asn Tyr Thr Asn Lys Phe Leu Leu Ile Pro Glu
                 20                  25                  30

Ser Gly Asp Tyr Phe Ile Tyr Ser Gln Val Thr Phe Arg Gly Met Thr
             35                  40                  45

Ser Glu Cys Ser Glu Ile Arg Gln Ala Gly Arg Pro Asn Lys Pro Asp
 50                  55                  60

Ser Ile Thr Val Val Ile Thr Lys Val Thr Asp Ser Tyr Pro Glu Pro
 65                  70                  75                  80

Thr Gln Leu Leu Met Gly Thr Lys Ser Val Cys Glu Val Gly Ser Asn
                 85                  90                  95

Trp Phe Gln Pro Ile Tyr Leu Gly Ala Met Phe Ser Leu Gln Glu Gly
                100                 105                 110

Asp Lys Leu Met Val Asn Val Ser Asp Ile Ser Leu Val Asp Tyr Thr
            115                 120                 125

Lys Glu Asp Lys Thr Phe Phe Gly Ala Phe Leu Leu
            130                 135                 140

<210> SEQ ID NO 6
<211> LENGTH: 157
<212> TYPE: PRT
<213> ORGANISM: Homo sapiens

<400> SEQUENCE: 6

Leu Pro Ala Ala His Leu Ile Gly Ala Pro Leu Lys Gly Gln Gly Leu
  1               5                  10                  15

Gly Trp Glu Thr Thr Lys Glu Gln Ala Phe Leu Thr Ser Gly Thr Gln
                 20                  25                  30

Phe Ser Asp Ala Glu Gly Leu Ala Leu Pro Gln Asp Gly Leu Tyr Tyr
             35                  40                  45

Leu Tyr Cys Leu Val Gly Tyr Arg Gly Arg Ala Pro Pro Gly Gly Gly
 50                  55                  60

Asp Pro Gln Gly Arg Ser Val Thr Leu Arg Ser Ser Leu Tyr Arg Ala
```

```
                    65                  70                  75                  80
Gly Gly Ala Tyr Gly Pro Gly Thr Pro Glu Leu Leu Glu Gly Ala
                85                  90                  95

Glu Thr Val Thr Pro Val Leu Asp Pro Ala Arg Arg Gln Gly Tyr Gly
            100                 105                 110

Pro Leu Trp Tyr Thr Ser Val Gly Phe Gly Gly Leu Val Gln Leu Arg
            115                 120                 125

Arg Gly Glu Arg Val Tyr Val Asn Ile Ser His Pro Asp Met Val Asp
    130                 135                 140

Phe Ala Arg Gly Lys Thr Phe Phe Gly Ala Val Met Val
145                 150                 155

<210> SEQ ID NO 7
<211> LENGTH: 136
<212> TYPE: PRT
<213> ORGANISM: Homo sapiens

<400> SEQUENCE: 7

His Ser Val Leu His Leu Val Pro Ile Asn Ala Thr Ser Lys Asp Asp
1               5                  10                  15

Ser Asp Val Thr Glu Val Met Trp Gln Pro Ala Leu Arg Arg Gly Arg
                20                  25                  30

Gly Leu Gln Ala Gln Gly Tyr Gly Val Arg Ile Gln Asp Ala Gly Val
            35                  40                  45

Tyr Leu Leu Tyr Ser Gln Val Leu Phe Gln Asp Val Thr Phe Thr Met
        50                  55                  60

Gly Gln Val Val Ser Arg Glu Gly Gln Gly Arg Gln Glu Thr Leu Phe
65                  70                  75                  80

Arg Cys Ile Arg Ser Met Pro Ser His Pro Asp Arg Ala Tyr Asn Ser
                85                  90                  95

Cys Tyr Ser Ala Gly Val Phe His Leu His Gln Gly Asp Ile Leu Ser
            100                 105                 110

Val Ile Ile Pro Arg Ala Arg Ala Lys Leu Asn Leu Ser Pro His Gly
        115                 120                 125

Thr Phe Leu Gly Phe Val Lys Leu
    130                 135

<210> SEQ ID NO 8
<211> LENGTH: 141
<212> TYPE: PRT
<213> ORGANISM: Homo sapiens

<400> SEQUENCE: 8

Gln Asp Cys Leu Gln Leu Ile Ala Asp Ser Glu Thr Pro Thr Ile Gln
1               5                  10                  15

Lys Gly Ser Tyr Thr Phe Val Pro Trp Leu Leu Ser Phe Lys Arg Gly
                20                  25                  30

Ser Ala Leu Glu Glu Lys Glu Asn Lys Ile Leu Val Lys Glu Thr Gly
            35                  40                  45

Tyr Phe Phe Ile Tyr Gly Gln Val Leu Tyr Thr Asp Lys Thr Tyr Ala
        50                  55                  60

Met Gly His Leu Ile Gln Arg Lys Lys Val His Val Phe Gly Asp Glu
65                  70                  75                  80

Leu Ser Leu Val Thr Leu Phe Arg Cys Ile Gln Asn Met Pro Glu Thr
                85                  90                  95

Leu Pro Asn Asn Ser Cys Tyr Ser Ala Gly Ile Ala Lys Leu Glu Glu
```

```
                    100                 105                 110
Gly Asp Glu Leu Gln Leu Ala Ile Pro Arg Glu Asn Ala Gln Ile Ser
        115                 120                 125

Leu Asp Gly Asp Val Thr Phe Phe Gly Ala Leu Lys Leu
    130                 135                 140

<210> SEQ ID NO 9
<211> LENGTH: 141
<212> TYPE: PRT
<213> ORGANISM: Homo sapiens

<400> SEQUENCE: 9

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Cys Leu Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu
    130                 135                 140

<210> SEQ ID NO 10
<211> LENGTH: 151
<212> TYPE: PRT
<213> ORGANISM: Homo sapiens

<400> SEQUENCE: 10

Gln Pro Phe Ala His Leu Thr Ile Asn Ala Thr Asp Ile Pro Ser Gly
1               5                   10                  15

Ser His Lys Val Ser Leu Ser Ser Trp Tyr His Asp Arg Gly Trp Ala
            20                  25                  30

Lys Ile Ser Asn Met Thr Phe Ser Asn Gly Lys Leu Ile Val Asn Gln
        35                  40                  45

Asp Gly Phe Tyr Tyr Leu Tyr Ala Asn Ile Cys Phe Arg His His Glu
    50                  55                  60

Thr Ser Gly Asp Leu Ala Thr Glu Tyr Leu Gln Leu Met Val Tyr Val
65                  70                  75                  80

Thr Lys Thr Ser Ile Lys Ile Pro Ser Ser His Thr Leu Met Lys Gly
                85                  90                  95

Gly Ser Thr Lys Tyr Trp Ser Gly Asn Ser Glu Phe His Phe Tyr Ser
            100                 105                 110

Ile Asn Val Gly Gly Phe Phe Lys Leu Arg Ser Gly Glu Glu Ile Ser
        115                 120                 125

Ile Glu Val Ser Asn Pro Ser Leu Leu Asp Pro Asp Gln Asp Ala Thr
    130                 135                 140

Tyr Phe Gly Ala Phe Lys Val
```

145          150

<210> SEQ ID NO 11
<211> LENGTH: 161
<212> TYPE: PRT
<213> ORGANISM: Homo sapiens

<400> SEQUENCE: 11

Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
            20                  25                  30

Asn Ser Trp Glu Ser Ser Arg Ser Gly His Ser Phe Leu Ser Asn Leu
        35                  40                  45

His Leu Arg Asn Gly Glu Leu Val Ile His Glu Lys Gly Phe Tyr Tyr
    50                  55                  60

Ile Tyr Ser Gln Thr Tyr Phe Arg Phe Gln Glu Glu Ile Lys Glu Asn
65                  70                  75                  80

Thr Lys Asn Asp Lys Gln Met Val Gln Tyr Ile Tyr Lys Tyr Thr Ser
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

His Leu Ile Asp Met Asp His Glu Ala Ser Phe Phe Gly Ala Phe Leu
145                 150                 155                 160

Val

<210> SEQ ID NO 12
<211> LENGTH: 126
<212> TYPE: PRT
<213> ORGANISM: Homo sapiens

<400> SEQUENCE: 12

Gly Pro Gln Gln Asp Pro Arg Leu Tyr Trp Gln Gly Gly Pro Ala Leu
1               5                   10                  15

Gly Arg Ser Phe Leu His Gly Pro Glu Leu Asp Lys Gly Gln Leu Arg
            20                  25                  30

Ile His Arg Asp Gly Ile Tyr Met Val His Ile Gln Val Thr Leu Ala
        35                  40                  45

Ile Cys Ser Ser Thr Thr Ala Ser Arg His His Pro Thr Thr Leu Ala
    50                  55                  60

Val Gly Ile Cys Ser Pro Ala Ser Arg Ser Ile Ser Leu Leu Arg Leu
65                  70                  75                  80

Ser Phe His Gln Gly Cys Thr Ile Val Ser Gln Arg Leu Thr Pro Leu
                85                  90                  95

Ala Arg Gly Asp Thr Leu Cys Thr Asn Leu Thr Gly Thr Leu Leu Pro
            100                 105                 110

Ser Arg Asn Thr Asp Glu Thr Phe Phe Gly Val Gln Trp Val
        115                 120                 125

<210> SEQ ID NO 13
<211> LENGTH: 153
<212> TYPE: PRT
<213> ORGANISM: Homo sapiens

<400> SEQUENCE: 13

```
Arg Gln Gly Met Phe Ala Gln Leu Val Ala Gln Asn Val Leu Leu Ile
1               5                   10                  15

Asp Gly Pro Leu Ser Trp Tyr Ser Asp Pro Gly Leu Ala Gly Val Ser
            20                  25                  30

Leu Thr Gly Gly Leu Ser Tyr Lys Glu Asp Thr Lys Glu Leu Val Val
        35                  40                  45

Ala Lys Ala Gly Val Tyr Tyr Val Phe Phe Gln Leu Glu Leu Arg Arg
    50                  55                  60

Val Val Ala Gly Glu Gly Ser Gly Ser Val Ser Leu Ala Leu His Leu
65                  70                  75                  80

Gln Pro Leu Arg Ser Ala Ala Gly Ala Ala Leu Ala Leu Thr Val
                85                  90                  95

Asp Leu Pro Pro Ala Ser Ser Glu Ala Arg Asn Ser Ala Phe Gly Phe
            100                 105                 110

Gln Gly Arg Leu Leu His Leu Ser Ala Gly Gln Arg Leu Gly Val His
        115                 120                 125

Leu His Thr Glu Ala Arg Ala Arg His Ala Trp Gln Leu Thr Gln Gly
    130                 135                 140

Ala Thr Val Leu Gly Leu Phe Arg Val
145                 150
```

<210> SEQ ID NO 14
<211> LENGTH: 98
<212> TYPE: PRT
<213> ORGANISM: Homo sapiens

<400> SEQUENCE: 14

```
Gly Glu Phe Ile Val Thr Arg Ala Gly Leu Tyr Tyr Leu Tyr Cys Gln
1               5                   10                  15

Val His Phe Asp Glu Gly Lys Ala Val Tyr Leu Lys Leu Asp Leu Leu
            20                  25                  30

Val Asp Gly Val Leu Ala Leu Arg Cys Leu Glu Glu Phe Ser Ala Thr
        35                  40                  45

Ala Ala Ser Ser Leu Gly Pro Gln Leu Arg Leu Cys Gln Val Ser Gly
    50                  55                  60

Leu Leu Ala Leu Arg Pro Gly Ser Ser Leu Arg Ile Arg Thr Leu Pro
65                  70                  75                  80

Trp Ala His Leu Lys Ala Ala Pro Phe Leu Thr Tyr Phe Gly Leu Phe
                85                  90                  95

Gln Val
```

<210> SEQ ID NO 15
<211> LENGTH: 138
<212> TYPE: PRT
<213> ORGANISM: Homo sapiens

<400> SEQUENCE: 15

```
Ala Pro Phe Lys Lys Ser Trp Ala Tyr Leu Gln Val Ala Lys His Leu
1               5                   10                  15

Asn Lys Thr Lys Leu Ser Trp Asn Lys Asp Gly Ile Leu His Gly Val
            20                  25                  30

Arg Tyr Gln Asp Gly Asn Leu Val Ile Gln Phe Pro Gly Leu Tyr Phe
        35                  40                  45

Ile Ile Cys Gln Leu Gln Phe Leu Val Gln Cys Pro Asn Asn Ser Val
```

```
                    50                  55                  60
Asp Leu Lys Leu Glu Leu Leu Ile Asn Lys His Ile Lys Lys Gln Ala
 65                  70                  75                  80

Leu Val Thr Val Cys Glu Ser Gly Met Gln Thr Lys His Val Tyr Gln
                     85                  90                  95

Asn Leu Ser Gln Phe Leu Leu Asp Tyr Leu Gln Val Asn Thr Thr Ile
                100                 105                 110

Ser Val Asn Val Asp Thr Phe Gln Tyr Ile Asp Thr Ser Thr Phe Pro
                115                 120                 125

Leu Glu Asn Val Leu Ser Ile Phe Leu Tyr
                130                 135

<210> SEQ ID NO 16
<211> LENGTH: 111
<212> TYPE: PRT
<213> ORGANISM: Homo sapiens

<400> SEQUENCE: 16

Lys Gly Phe Ile Leu Thr Ser Gln Lys Glu Asp Glu Ile Met Lys Val
  1               5                  10                  15

Gln Asn Asn Ser Val Ile Ile Asn Cys Asp Gly Phe Tyr Leu Ile Ser
                 20                  25                  30

Leu Lys Gly Tyr Phe Ser Gln Glu Val Asn Ile Ser Leu His Tyr Gln
             35                  40                  45

Lys Asp Glu Glu Pro Leu Phe Gln Leu Lys Lys Val Arg Ser Val Asn
         50                  55                  60

Ser Leu Met Val Ala Ser Leu Thr Tyr Lys Asp Lys Val Tyr Leu Asn
 65                  70                  75                  80

Val Thr Thr Asp Asn Thr Ser Leu Asp Asp Phe His Val Asn Gly Gly
                 85                  90                  95

Glu Leu Ile Leu Ile His Gln Asn Pro Gly Glu Phe Cys Val Leu
                100                 105                 110

<210> SEQ ID NO 17
<211> LENGTH: 113
<212> TYPE: PRT
<213> ORGANISM: Homo sapiens

<400> SEQUENCE: 17

Cys Met Ala Lys Phe Gly Pro Leu Pro Ser Lys Trp Gln Met Ala Ser
  1               5                  10                  15

Ser Glu Pro Pro Cys Val Asn Lys Val Ser Asp Trp Lys Leu Glu Ile
                 20                  25                  30

Leu Gln Asn Gly Leu Tyr Leu Ile Tyr Gly Gln Val Ala Pro Asn Ala
             35                  40                  45

Asn Tyr Asn Asp Val Ala Pro Phe Glu Val Arg Leu Tyr Lys Asn Lys
         50                  55                  60

Asp Met Ile Gln Thr Leu Thr Asn Lys Ser Lys Ile Gln Asn Val Gly
 65                  70                  75                  80

Gly Thr Tyr Glu Leu His Val Gly Asp Thr Ile Asp Leu Ile Phe Asn
                 85                  90                  95

Ser Glu His Gln Val Leu Lys Asn Asn Thr Tyr Trp Gly Ile Ile Leu
                100                 105                 110

Leu

<210> SEQ ID NO 18
```

```
<211> LENGTH: 33
<212> TYPE: PRT
<213> ORGANISM: Artificial sequence
<220> FEATURE:
<223> OTHER INFORMATION: coiled-coil motif

<400> SEQUENCE: 18

Arg Met Glu Lys Leu Glu Gln Lys Val Lys Glu Leu Leu Arg Lys Asn
1               5                   10                  15

Glu Arg Leu Glu Glu Val Glu Arg Leu Lys Gln Leu Val Gly Glu
            20                  25                  30

Arg

<210> SEQ ID NO 19
<211> LENGTH: 24
<212> TYPE: PRT
<213> ORGANISM: Artificial sequence
<220> FEATURE:
<223> OTHER INFORMATION: coiled-coil motif

<400> SEQUENCE: 19

Ala Ala Leu Glu Ser Glu Val Ser Ala Leu Glu Ser Glu Val Ala Ser
1               5                   10                  15

Leu Glu Ser Glu Val Ala Ala Leu
            20

<210> SEQ ID NO 20
<211> LENGTH: 24
<212> TYPE: PRT
<213> ORGANISM: Artificial sequence
<220> FEATURE:
<223> OTHER INFORMATION: coiled-coil motif

<400> SEQUENCE: 20

Leu Ala Ala Val Lys Ser Lys Leu Ser Ala Val Lys Ser Lys Leu Ala
1               5                   10                  15

Ser Val Lys Ser Lys Leu Ala Ala
            20

<210> SEQ ID NO 21
<211> LENGTH: 5
<212> TYPE: PRT
<213> ORGANISM: Artificial sequence
<220> FEATURE:
<223> OTHER INFORMATION: linker consensus sequence

<400> SEQUENCE: 21

Gly Ser Gly Gly Ser
1               5

<210> SEQ ID NO 22
<211> LENGTH: 5
<212> TYPE: PRT
<213> ORGANISM: Artificial sequence
<220> FEATURE:
<223> OTHER INFORMATION: linker consensus sequence

<400> SEQUENCE: 22

Gly Gly Gly Gly Ser
1               5

<210> SEQ ID NO 23
<211> LENGTH: 4
<212> TYPE: PRT
<213> ORGANISM: Artificial sequence
```

-continued

```
<220> FEATURE:
<223> OTHER INFORMATION: linker consensus sequence

<400> SEQUENCE: 23

Gly Gly Gly Ser
1
```